(12) United States Patent
Akil et al.

(10) Patent No.: US 7,687,235 B2
(45) Date of Patent: Mar. 30, 2010

(54) COMPOSITIONS AND METHODS FOR DIAGNOSING AND TREATING NEUROPSYCHIATRIC DISORDERS

(75) Inventors: Huda Akil, Ann Arbor, MI (US); Mary Atz, Tustin, CA (US); William E. Bunney, Jr., Laguna Hills, CA (US); William Byerley, San Francisco, CA (US); Kathleen Casey, Santa Ana, CA (US); Prabhakara V. Choudary, Davis, CA (US); Simon J. Evans, Milan, MI (US); Edward G. Jones, Winters, CA (US); Jun Li, Palo Alto, CA (US); Juan F. Lopez, Ann Arbor, MI (US); Richard M. Myers, Stanford, CA (US); Brandi Rollins, Laguna Hills, CA (US); Robert C. Thompson, Ann Abror, MI (US); Hiroaki Tomita, Irvine, CA (US); Marquis P. Vawter, Niguel, CA (US); Stanley J. Watson, Ann Arbor, MI (US)

(73) Assignee: The Board of Regents of the Leland Stanford Junior University, Palo Alto, CA (US)

( * ) Notice: Subject to any disclaimer, the term of this patent is extended or adjusted under 35 U.S.C. 154(b) by 411 days.

(21) Appl. No.: 11/396,050

(22) Filed: Mar. 31, 2006

(65) Prior Publication Data
US 2006/0257903 A1 Nov. 16, 2006

Related U.S. Application Data

(60) Provisional application No. 60/667,299, filed on Mar. 31, 2005, provisional application No. 60/776,103, filed on Feb. 22, 2006.

(51) Int. Cl.
C12Q 1/68 (2006.01)
C12P 19/34 (2006.01)
(52) U.S. Cl. .......................... 435/6; 435/91.2
(58) Field of Classification Search ...................... None
See application file for complete search history.

(56) References Cited

U.S. PATENT DOCUMENTS

2001/0051344 A1* 12/2001 Shalon et al. .................. 435/6
2004/0106142 A1* 6/2004 Ivey et al. ...................... 435/6
2006/0246495 A1* 11/2006 Garrett et al. .................. 435/6

FOREIGN PATENT DOCUMENTS

WO    WO 2006/105516       5/2006
WO    WO 2008/048639 A2 *  4/2008

OTHER PUBLICATIONS

Sliwerska E. et al. 'SNPs on Chips: The Hidden Genetic Code in Expression Arrays' Biol Psychiatry 2007;61:13-16.*
Hoshikawa Y. et al. 'Hypoxia induces different genes in the lungs of rats compared with mice' Physiol Genomics 12: 209-219, 2003.*
Tomita H. et al. 'Gene Expression Profiles in Postmortem Brains of Mood Disorder Patients'. Program No. 640.19. 2003 Abstract Viewer/Itinerary Planner. Washington, DC: Society for Neuroscience, 2003. Printed from sfn.scholarone.com, 1 page, Abstract only.*
Lopez J.F. et al. 'Gene Expression Profile in the Frontal Cortex of Rats Subjected to Chronic Unpredictable Stress and Antidepressant Administration: A Comparison With Human Postmortem Studies'. Program No. 756.12. 2003 Abstract Viewer/Itinerary Planner. Washington, DC: Society for Neuroscience, 2003. Printed from sfn.scholarone.com, 1 page.*
Li J. et al. 'Identification of Differentially Expressed Genes in Two Cortical Regions of Patients With Mood Disorders by Serial Analysis of Gene Expression (SAGE)'. Program No. 779.5. 2003 Abstract Viewer/Itinerary Planner. Washington, DC: Society for Neuroscience, 2003. Printed from sfn.scholarone.com, 1 page, Abstract only.*
Vawter. M.P. et al. 'Patterns of Differential Gene Expression in Schizophrenia Overlap in Cortical Regions'. Program No. 881.3. 2003 Abstract Viewer/Itinerary Planner. Washington, DC: Society for Neuroscience, 2003. Printed from sfn.scholarone.com, 1 page, Abstract only.*
Evans S.J. et al. 'Comparison of Gene Expression Profiles Between Bipolar Disorder, Major Depression and Schizophrenia in Cortical Brain Regions'. Program No. 312.15. 2003 Abstract Viewer/Itinerary Planner. Washington, DC: Society for Neuroscience, 2003. Printed from sfn.scholarone.com, 1 page, Abstract only.*
Choudary P.V. et al. 'Dorsal Lateral Prefrontal Cortex and Mediodorsal Thalamus in Schizophrenic Brains Show Concordant and Discordant Alterations in Gene Expression'. Program No. 312.14. 2003 Abstract Viewer/Itinerary Planner. Washington, DC: Society for Neuroscience, 2003. Printed from sfn.scholarone.com, 1 page, Abstract only.*
GenBank Locus NM_006558, Homo sapiens KH domain containing, RNA binding, signal transduction associated 3 (KHDRBS3), mRNA, No. 27, 2005, pp. 1-4.
Chan, E. Integrating Transcriptomics and Proteomics. Drug Discovery & Development: vol. 6, No. 3, Apr. 2006, pp. 20-26. printed pp. 1-6.
Cheung, Vivian, et al. "Natural variation in human gene expression assessed in 4 lymphoblastoid cells," Nature Genetics, 2003, vol. 33, No. 3, pp. 422-425.
Ernst, Carl, et al. "Confirmation of region-specific patterns of gene expression in the human brain," Neurogenetics, 2007, vol. 8, No. 3, pp. 219-224.

(Continued)

Primary Examiner—Stephen Kapushoc
(74) Attorney, Agent, or Firm—Townsend and Townsend and Crew LLP

(57) ABSTRACT

The present invention provides methods for diagnosing mental disorders (e.g., psychotic disorders such as schizophrenia and mood disorders such as major depression disorder and bipolar disorder). The invention also provides methods of identifying modulators of such mental disorders as well as methods of using these modulators to treat patients suffering from such mental disorders.

9 Claims, 73 Drawing Sheets

OTHER PUBLICATIONS

Burmeister, M. "Basic concepts in the study of Disease with Complex Genetics," Biol. Psychiatry, 1999, vol. 45, No. 5, pp. 522-532.

Choudary, et al., "Dorsal Lateral Prefrontal Cortex and Mediodorsal Thalamus in Schizophrenic Brains Show Concordant and Discordant Alterations in Gene Expression," 33$^{rd}$ Annual Meeting of the Society of Neuroscience, Nov. 8-12, 2003 (Washington, DC) 1 page.

Evans et al, "Comparison of Gene Expression Profiles Between Bipolar Disorder, Major Depression and Schizophrenia," 33$^{rd}$ Annual Meeting of the Society of Neuroscience, Nov. 8-12, 2003 (Washington, DC) 1 page.

Li et al., "Identification of differentially expressed genes in two cortical regions of patients with mood disorders by Serial Analysis of Gene Expression (SAGE)," 33$^{rd}$ Annual Meeting of the Society of Neuroscience, Nov. 8-12, 2003 (Washington, DC) 16 pages.

López et al., "Gene Expression Profile in the Frontal Cortex of Rats Subjected to Chronic Unpredictable Stress and Antidepressant Administration: A Comparison with Human Postmortem Studies," 33$^{rd}$ Annual Meeting of the Society of Neuroscience, Nov. 8-12, 2003 (Washington, DC) 9 pages.

Tomita et al., "Effect of Mood Disorders and Suicide on Gene Expression Profiles in Postmortem Brains," 33$^{rd}$ Annual Meeting of the Society of Neuroscience, Nov. 8-12, 2003 (Washington, DC) 9 pages.

Vawter et al., "Patterns of Differential Gene Expression in Schizophrenia Overlap in Cortical Regions," 33$^{rd}$ Annual Meeting of the Society of Neuroscience, Nov. 8-12, 2003 (Washington, DC) 1 page.

\* cited by examiner

| | Annotation | | | Direction of Change in SZ relative to Controls | | | | | | | Name |
|---|---|---|---|---|---|---|---|---|---|---|---|
| UniGene ID | Acc | Symbol | Chr. | AnCg | CB | DLPFC | Nacc | PC | STG | | |
| Hs.444558 | AA007604 | KHDRBS3 | 8 | | | up | | | | | KH domain containing, RNA binding, signal transduction associated 3 |
| Hs.101139 | AA017257 | | 19 | down | | | | | | | Transcribed locus |
| Hs.443049 | AA251773 | | 7 | | down | | | | | | Transcribed locus |
| Hs.192788 | AA314461 | LOC389677 | 8 | | | | | | up | | Similar to RIKEN cDNA 3000004N20 |
| Hs.485557 | AA418695 | GSTA4 | 6 | | | | | down | down | | Glutathione S-transferase A4 |
| Hs.535419 | AA447681 | | 18 | | | up | | | up | | Hypothetical LOC388459 |
| Hs.36958 | AA496799 | BCAR3 | 1 | | | | | | down | | Breast cancer anti-estrogen resistance 3 |
| Hs.4204 | AA700440 | | 1 | | | | | down | | | CDNA FLJ30779 fis, clone FEBRA2000815 |
| Hs.241548 | AA743526 | RASA2 | 3 | | up | | | | | | RAS p21 protein activator 2 |
| Hs.524367 | AA779991 | CBARA1 | 10 | down | | | | | | | Calcium binding atopy-related autoantigen 1 |
| Hs.532987 | AA827062 | C18orf22 | 18 | down | | | | | | | Chromosome 18 open reading frame 22 |
| Hs.136905 | AB002310 | UREB1 | | | | | | down | | | Upstream regulatory element binding protein 1 |
| Hs.114169 | AB007876 | LRRTM2 | 5 | | | | up | | | | Leucine rich repeat transmembrane neuronal 2 |
| Hs.435557 | AB011103 | KIF5C | 2 | | | | up | | | | Kinesin family member 5C |
| Hs.383564 | AB011146 | KIAA0574 | 15 | | | | up | | | | KIAA0574 protein |
| Hs.146007 | AB011154 | KIAA0582 | 2 | | | up | | | | | KIAA0582 |
| Hs.118140 | AB018259 | DOCK4 | 7 | | | | | | down | | Dedicator of cytokinesis 4 |
| Hs.153610 | AB018294 | RIMS2 | 8 | | | | up | | | | Regulating synaptic membrane exocytosis 2 |
| Hs.178471 | AB018341 | ZNF432 | 19 | | | | | down | | | Zinc finger protein 432 |
| Hs.466261 | AB021644 | ZNF14 | 19 | | down | | | | down | | Zinc finger protein 14 (KOX 6) |
| Hs.303454 | AB023136 | SEC15L2 | 2 | down | | | | | | | SEC15-like 2 (S. cerevisiae) |
| Hs.298658 | AB024523 | KLF3 | 4 | | up | | | | | | Kruppel-like factor 3 (basic) |
| Hs.476399 | AB029028 | RAP140 | 3 | | | | down | down | | | Retinoblastoma-associated protein 140 |
| Hs.132813 | AB029033 | IQSEC3 | 12 | | | down | | | | | IQ motif and Sec7 domain 3 |
| Hs.12264 | AB032989 | KIAA1163 | | down | | | | down | | | Amphoterin-induced gene |
| Hs.50823 | AB033060 | PDCD6 | 5 | down | | | | | | | Programmed cell death 6 |
| Hs.472285 | AB033098 | KIAA1272 | 20 | | | | | down | | | KIAA1272 protein |
| Hs.537101 | AB033338 | | | | | down | | | | | KRMP1 mRNA for mitotic kinesin-related protein, partial cds, alternative exon sequence. |
| Hs.140903 | AB037744 | MIB1 | 18 | | | up | | | | | Mindbomb homolog 1 (Drosophila) |
| Hs.3346 | AB037811 | FLJ11280 | 1 | | up | | | | | | Hypothetical protein FLJ11280 |
| Hs.377588 | AB040883 | KIAA1450 | 4 | up | | | | | | | KIAA1450 protein |
| Hs.287362 | AB046767 | TLE3 | 15 | | | | | | up | | Transducin-like enhancer of split 3 (E(sp1) homolog, |

| Annotation | | | | Direction of Change in SZ relative to Controls | | | | | | | Name |
|---|---|---|---|---|---|---|---|---|---|---|---|
| UniGene ID | Acc | Symbol | Chr. | AnCg | CB | DLPFC | Nacc | PC | STG | | |
| Hs.13305 | AB046788 | ROBO2 | 3 | | up | | | | | | Roundabout, axon guidance receptor, homolog 2 (Drosophila) |
| Hs.474914 | AB051446 | RUTBC3 | 22 | down | | | | | | | RUN and TBC1 domain containing 3 |
| Hs.510745 | AB097009 | HNLF | 7 | | | | | | down | | Putative NFkB activating protein HNLF |
| Hs.523789 | AF001893 | TncRNA | 11 | | | | | | down | | Trophoblast-derived noncoding RNA |
| Hs.352614 | AF007155 | LOC254531 | 15 | | | down | | | | | PLSC domain containing protein |
| Hs.147770 | AF012023 | ITGB1BP1 | 2 | up | | | | | | | Integrin beta 1 binding protein 1 |
| Hs.42400 | AF022789 | USP12 | 13 | up | | | | | | | Ubiquitin specific protease 12 |
| Hs.465784 | AF026030 | TIMM44 | 19 | | up | | | | | | Translocase of inner mitochondrial membrane 44 homolog (yeast) |
| Hs.12451 | AF035276 | EML1 | 14 | up | | | | | | | Echinoderm microtubule associated protein like 1 |
| Hs.12473 | AF052109 | | 1 | | | | up | | | | cDNA clone IMAGE:5260262, partial cds |
| Hs.13438 | AF052141 | | 4 | | | | up | | | | Clone 24626 mRNA sequence |
| Hs.368046 | AF054993 | SNAP91 | 6 | | | | up | | | | Synaptosomal-associated protein, 91kDa homolog (mouse) |
| Hs.129997 | AF070534 | | 13 | | | | up | | | | Clones 24632 and 24634 mRNA sequence |
| Hs.48372 | AF086092 | | 4 | | | | | down | | | Full length insert cDNA clone YZ87G11 |
| Hs.513509 | AF086220 | FLJ32130 | 16 | down | | | | | | | Hypothetical protein FLJ32130 |
| Hs.131133 | AF087875 | PRKAG2 | 7 | | up | | | | | | Protein kinase, AMP-activated, gamma 2 non-catalytic subunit |
| Hs.34560 | AF116668 | LMO2 | 11 | | | down | | down | | | LIM domain only 2 (rhombotin-like 1) |
| Hs.142245 | AF126163 | HHLA3 | 1 | up | | | | | | | HERV-H LTR-associating 3 |
| Hs.446240 | AF144233 | PRKCBP1 | 20 | down | down | | | | | | Protein kinase C binding protein 1 |
| Hs.47261 | AF260704 | SLCO1C1 | 12 | | | | down | | down | | Solute carrier organic anion transporter family, member 1C1 |
| Hs.371788 | AF318362 | DKFZP547 E1010 | 1 | up | | | | | | | DKFZP547E1010 protein |
| Hs.125747 | AF381172 | | 17 | | up | | | | | | AA02 pseudogene mRNA, partial sequence, mRNA sequence |
| Hs.187946 | AI240538 | | 2 | | | | | down | down | | Hypothetical gene supported by AK124342 |
| Hs.23187 | AI242476 | | 7 | | down | | | | | | Transcribed locus |
| Hs.328801 | AI308898 | | 8 | | | down | | | | | Transcribed locus |
| Hs.542164 | AI417157 | | 19 | up | | | | | | | cDNA FLJ41369 fis, clone BRCAN2006117 |
| Hs.421200 | AI480014 | | 5 | down | | up | | | | | Clone 24571 mRNA sequence |

| Annotation | | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.445066 | AI499801 | GRIN2B | 12 | | | | | down | | Glutamate receptor, ionotropic, N-methyl D-aspartate 2B |
| Hs.47995 | AI610676 | | 10 | | down | | | | | Full-length cDNA clone CS0DC007YK10 of Neuroblastoma Cot 25-normalized of Homo sapiens (human) |
| Hs.503584 | AI638679 | PANX1 | 11 | | | up | | | | Pannexin 1 |
| Hs.174746 | AI670992 | | 3 | | | | | down | | Transcribed locus |
| Hs.440729 | AI671849 | | 3 | | | down | | | | Transcribed locus |
| Hs.404218 | AI674644 | | 8 | | down | | | | | Transcribed locus |
| Hs.530218 | AI679805 | | 8 | | | | | | down | Transcribed locus |
| Hs.537738 | AI692882 | | 16 | | up | | | | | Full length insert cDNA clone ZD81C11 |
| Hs.513356 | AI694544 | | 16 | up | down | | | | | Transcribed locus, moderately similar to XP_498452.1 hypothetical gene supported by NM_173697 [Homo sapiens] |
| Hs.356084 | AI703476 | GPR27 | 3 | up | up | | | | up | G protein-coupled receptor 27 |
| Hs.201106 | AI758946 | | 1 | | | | | | | Transcribed locus |
| Hs.192788 | AI768185 | LOC389677 | 8 | | | | | | up | Similar to RIKEN cDNA 3000004N20 |
| Hs.202054 | AI796835 | | | | | down | | | | Transcribed locus |
| Hs.536522 | AI822096 | SMAD4 | 5 | | up | | | | up | SMAD, mothers against DPP homolog 4 (Drosophila) |
| Hs.97104 | AI823879 | | | | | | | | | Transcribed locus |
| Hs.94949 | AI934339 | MCEE | 2 | up | | | | | | Methylmalonyl CoA epimerase |
| Hs.142869 | AI935586 | | 4 | | up | | | | | Transcribed locus |
| Hs.459255 | AI935701 | NTRK3 | 15 | up | | | | | | Neurotrophic tyrosine kinase, receptor, type 3 |
| Hs.114033 | AJ420492 | SSR1 | 6 | | | down | | | down | Signal sequence receptor, alpha (translocon-associated protein alpha) |
| Hs.445098 | AK000490 | DEPDC1 | 1 | | up | | | | | DEP domain containing 1 |
| Hs.517134 | AK000586 | C20orf43 | 20 | up | | | | | | Chromosome 20 open reading frame 43 |
| Hs.288995 | AK000820 | ZNF587 | 19 | | | | | down | down | Zinc finger protein 587 |
| Hs.471221 | AK000969 | KLF7 | 2 | | | up | | | | Kruppel-like factor 7 (ubiquitous) |
| Hs.301943 | AK001249 | KIAA0467 | 1 | | down | | | | | KIAA0467 protein |
| Hs.144055 | AK001563 | SBNO1 | 12 | | up | | | | up | Sno, strawberry notch homolog 1 (Drosophila) |
| Hs.27021 | AK001697 | RIOK2 | 5 | | down | | | | down | RIO kinase 2 (yeast) |
| Hs.443260 | AK001776 | C20orf20 | 20 | | down | down | | | down | Chromosome 20 open reading frame 20 |
| Hs.516311 | AK001856 | | 2 | | | | | down | | Homo sapiens, clone IMAGE:4826696, mRNA |
| Hs.92308 | AK002085 | LOC144438 | 12 | | | up | | | | Hypothetical protein LOC144438 |
| Hs.477693 | AK021677 | NCK1 | 3 | down | | | | | | NCK adaptor protein 1 |

| Annotation | | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.481819 | AK021922 | PDZK3 | 5 | | | | | | down | PDZ domain containing 3 |
| Hs.476982 | AK022155 | CPOX | 3 | | up | | | | | Coproporphyrinogen oxidase |
| Hs.492445 | AK022204 | EDD | 8 | | | | | down | | E3 identified by differential display |
| Hs.31431 | AK022233 | FN3KRP | 17,20 ,9 | up | | | | | | Fructosamine-3-kinase-related protein |
| Hs.285782 | AK022630 | LRRTM4 | 2 | | | up | | | | Leucine rich repeat transmembrane neuronal 4 |
| Hs.132794 | AK022741 | PCYT1B | X | | | up | up | | | Phosphate cytidylyltransferase 1, choline, beta isoform |
| Hs.321653 | AK022832 | FLJ12770 | 1 | up | | | | | | Hypothetical protein FLJ12770 |
| Hs.167165 | AK023037 | FLJ12975 | 12 | | | | | down | | Hypothetical protein FLJ12975 |
| Hs.440833 | AK023692 | PKN2 | 1 | | | | | down | | Protein kinase N2 |
| Hs.274422 | AK024220 | C20orf27 | 20 | up | | | | | | Chromosome 20 open reading frame 27 |
| Hs.473374 | AK025196 | PTPRK | 6 | | | down | | | | Protein tyrosine phosphatase, receptor type, K |
| Hs.431081 | AK025233 | USP53 | 4 | | down | | | | | Ubiquitin specific protease 53 |
| Hs.499483 | AK025626 | LOC83693 | 16 | up | | | | | | Steroid dehydrogenase-like |
| Hs.465295 | AK025773 | LMAN1 | 18 | | | up | | | | Lectin, mannose-binding, 1 |
| Hs.289092 | AK026033 | COTL1 | 16;11 | | | | | up | | Coactosin-like 1 (Dictyostelium) |
| Hs.537428 | AK026035 | | | | | | | down | | CDNA FLJ34018 fis, clone FCBBF2002801 |
| Hs.426324 | AK026149 | TUSC3 | 8 | | up | | | | | Tumor suppressor candidate 3 |
| Hs.2772759 | AK026156 | PITPNM2 | | up | | | | | | Phosphatidylinositol transfer protein, membrane-associated 2 |
| Hs.535771 | AK026466 | CYFIP2 | 5 | down | | | | | | Cytoplasmic FMR1 interacting protein 2 |
| Hs.524341 | AK026495 | SLC2A13 | 12 | | up | | | | | Solute carrier family 2 (facilitated glucose transporter), member 13 |
| Hs.79881 | AK026659 | | 3 | | down | | | | | CDNA: FLJ23006 fis, clone LNG00414 |
| Hs.91521 | AK026748 | DKFZP761 M1511 | 5 | up | | | | | up | Hypothetical protein DKFZP761M1511 |
| Hs.301296 | AK026784 | | 13 | | down | | | | | CDNA: FLJ23131 fis, clone LNG08502 |
| Hs.415842 | AK026870 | RBM18 | 9 | | | up | | | | RNA binding motif protein 18 |
| Hs.292575 | AK026980 | ZNF37B | 10;7; 1 | down | | | | | | Zinc finger protein 37b (KOX 21) |
| Hs.111286 | AK027059 | MRPS11 | 15 | | up | | | | | Mitochondrial ribosomal protein S11 |
| Hs.130692 | AK027273 | MGC10946 | 12 | | down | | | up | | Hypothetical protein MGC10946 |
| Hs.452398 | AK055302 | | 2 | down | | | | | | MRNA; cDNA DKFZp564E143 (from clone DKFZp564E143) |
| Hs.532786 | AK055378 | LOC339287 | 17 | up | | | | | | Hypothetical protein LOC339287 |

| Annotation | | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.148105 | AK055479 | PRICKLE2 | 3 | up | | | | | | Prickle-like 2 (Drosophila) |
| Hs.536251 | AK056079 | JAM2 | 21 | | | | | down | | Junctional adhesion molecule 2 |
| Hs.47918 | AK056549 | CNKSR2 | X | | | | up | | | Connector enhancer of kinase suppressor of Ras 2 |
| Hs.193115 | AK057990 | KIAA1764 | 8 | down | | | | | | KIAA1764 protein |
| Hs.251399 | AK074730 | HRH3 | 20 | up | | | | | | Histamine receptor H3 |
| Hs.254414 | AK090803 | SRrp35 | 6 | up | | | | | | Serine-arginine repressor protein (35 kDa) |
| Hs.242947 | AK091081 | DGKI | 7 | | | up | | | | Diacylglycerol kinase, iota |
| Hs.443731 | AK091775 | USP8 | 15 | | up | | | | | Ubiquitin specific protease 8 |
| Hs.494804 | AK091948 | LTB4DH | 9 | | | up | | | | Leukotriene B4 12-hydroxydehydrogenase |
| Hs.179153 | AK092145 | | 9 | | up | | | | | CDNA FLJ34826 fis, clone NT2NE2008803 |
| Hs.177275 | AK092235 | ANKRD6 | 6 | up | | | | | | Ankyrin repeat domain 6 |
| Hs.433956 | AK092711 | | 2 | | up | | | | | Hypothetical LOC400944 |
| Hs.144447 | AK092984 | WDR11 | 10 | | | | | down | | WD repeat domain 11 |
| Hs.293077 | AK093067 | CHPT1 | 12 | | | up | | | | Choline phosphotransferase 1 |
| Hs.523467 | AK093229 | NRIP3 | 11 | | | | | | up | Nuclear receptor interacting protein 3 |
| Hs.465462 | AK093588 | | 18 | | | | | | up | CDNA FLJ36269 fis, clone THYMU2003012 |
| Hs.12248 | AK093871 | CXXC4 | 4 | | up | | | | up | CXXC finger 4 |
| Hs.451846 | AK093939 | RGPR | 1 | down | | | | | | Regucalcin gene promotor region related protein |
| Hs.331667 | AK094282 | MGC3200 | 1 | | | down | | | | Hypothetical protein LOC284615 |
| Hs.22654 | AK094487 | SCN1A | 2 | | | | up | | | Sodium channel, voltage-gated, type I, alpha |
| Hs.26479 | AK094535 | | 3 | | | up | | down | | CDNA FLJ37216 fis, clone BRALZ2008696 |
| Hs.438695 | AK094876 | FKBP11 | 12 | down | | | | | | FK506 binding protein 11, 19 kDa |
| Hs.380250 | AK094968 | IFI16 | 1 | | | | down | | | Interferon, gamma-inducible protein 16 |
| Hs.466987 | AK095884 | PRKD2 | 19 | | | down | | | | Protein kinase D2 |
| Hs.128686 | AK097398 | NUCB2 | 11 | | | up | | | | Nucleobindin 2 |
| Hs.169378 | AK098775 | MPDZ | 9 | | | | down | down | | Multiple PDZ domain protein |
| Hs.494312 | AK123824 | NTRK2 | 9 | | up | | | | | Neurotrophic tyrosine kinase, receptor, type 2 |
| Hs.525589 | AK123878 | MEG3 | 14 | | | | | up | | Maternally expressed 3 |
| Hs.164649 | AK124629 | IXL | 19 | | | | | down | | Intersex-like (Drosophila) |
| Hs.476782 | AK126999 | EIF4E3 | 3 | | | up | | | up | Eukaryotic translation initiation factor 4E member 3 |
| Hs.297044 | AK127019 | RUFY2 | 10 | | | down | | | | RUN and FYVE domain containing 2 |
| Hs.256801 | AK127476 | ZNF493 | | up | | | | | | Zinc finger protein 493 |
| Hs.520804 | AK128034 | | 7 | | | | | | down | Similar to cell division cycle 10 homolog |
| Hs.435767 | AK129838 | PCYT1A | 3 | | down | | | | | Phosphate cytidylyltransferase 1, choline, alpha isoform |
| Hs.126914 | AK130263 | KIAA1430 | 4 | up | | | | | | KIAA1430 |

| | Annotation | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | Name |
| Hs.512181 | AK130506 | CXorf33 | 4 | down | | | | | | Chromosome X open reading frame 33 |
| Hs.480825 | AK130520 | RNF150 | 11 | | | up | | | | Ring finger protein 150 |
| Hs.184216 | AL049980 | DKFZP564 C152 | 11 | | | | | | down | DKFZP564C152 protein |
| Hs.155090 | AL117471 | GNB5 | 15 | | | | up | | | Guanine nucleotide binding protein (G protein), beta 5 |
| Hs.421907 | AL122063 | GLTSCR2 | 19 | | | down | | | | Glioma tumor suppressor candidate region gene 2 |
| Hs.158688 | AL133563 | EIF5B | 2 | down | | | | | | Eukaryotic translation initiation factor 5B |
| Hs.435700 | AL137537 | ATP8B2 | 1 | | up | | | | | ATPase, Class I, type 8B, member 2 |
| Hs.478125 | AL137692 | INADL | 1 | | | | | | up | InaD-like protein |
| Hs.26815 | AL360202 | THAP10 | 15 | | | up | | | | THAP domain containing 10 |
| Hs.475103 | AL389951 | NUP50 | 22 | | | | | | up | Nucleoporin 50kDa |
| Hs.536940 | AL512705 | APEG1 | 2 | | | down | | | | Aortic preferentially expressed protein 1 |
| Hs.292549 | AL831922 | DLG1 | 3 | | | | down | | | Discs, large homolog 1 (Drosophila) |
| Hs.268675 | AL831995 | MEF2A | 15 | up | up | up | | | | MADS box transcription enhancer factor 2, polypeptide A (myocyte enhancer factor 2A) |
| Hs.518099 | AL832398 | MGC26717 | 3 | | down | up | | | | Hypothetical protein MGC26717 |
| Hs.30141 | AL832603 | FLJ20313 | 15 | | down | | | | | Hypothetical protein FLJ20313 |
| Hs.175343 | AL832699 | PIK3C2A | 11 | | | | | down | | Phosphoinositide-3-kinase, class 2, alpha polypeptide |
| Hs.490790 | AL833137 | THAP5 | 7 | | | | | | | THAP domain containing 5 |
| Hs.430300 | AL833360 | | 11 | | down | | | | | MRNA; cDNA DKFZp667E0114 (from clone DKFZp667E0114) |
| Hs.477921 | AL833852 | WWTR1 | 3 | | down | | | | | WW domain containing transcription regulator 1 |
| Hs.282855 | AL834302 | FLJ12994 | 15 | | up | | | | | Hypothetical protein FLJ12994 |
| Hs.32468 | AV718518 | | 5 | | | up | | | | Transcribed locus |
| Hs.163924 | AW080999 | NR3C2 | 4 | | | | | down | | Nuclear receptor subfamily 3, group C, member 2 |
| Hs.418198 | AW086065 | PAPD4 | 5 | | | | | down | down | PAP associated domain containing 4 |
| Hs.446340 | AW291402 | | | | | up | | | | Transcribed locus |
| Hs.293379 | AW302422 | | 19 | | up | | | | | Transcribed locus |
| Hs.429 | AW438709 | ATP5G3 | 2 | | | down | | | | ATP synthase, H+ transporting, mitochondrial F0 complex, subunit c (subunit 9) isoform 3 |
| Hs.408427 | AW451792 | COMMD7 | 20 | up | | | | | | COMM domain containing 7 |
| Hs.436556 | AW571739 | | 7 | down | | | | | | Transcribed locus |
| Hs.257786 | AW964241 | | 2 | | | | | up | | Transcribed locus |
| Hs.306423 | BC000825 | LOC339524 | 1 | | | | | | down | Hypothetical protein LOC339524 |
| Hs.434953 | BC001063 | HMGB2 | 4 | | | up | | | | High-mobility group box 2 |

| | Annotation | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.535659 | BC002458 | MCM3AP | 21 | | up | | | | | MCM3 minichromosome maintenance deficient 3 (S. cerevisiae) associated protein |
| Hs.483239 | BC002515 | ALDH7A1 | 5 | up | | | down | | | Aldehyde dehydrogenase 7 family, member A1 |
| Hs.7001 | BC002867 | C14orf9 | | up | | | | | | Chromosome 14 open reading frame 9 |
| Hs.224282 | BC004887 | LANCL2 | 7 | | | up | | | | LanC lantibiotic synthetase component C-like 2 (bacterial) |
| Hs.471582 | BC004921 | LOC93349 | 2 | | | down | | | | Hypothetical protein BC004921 |
| Hs.516859 | BC005095 | PANK2 | 20 | | down | | | | | Pantothenate kinase 2 (Hallervorden-Spatz syndrome) |
| Hs.153546 | BC005258 | CDC23 | 5 | | | up | | | | CDC23 (cell division cycle 23, yeast, homolog) |
| Hs.18788 | BC006283 | DHRS10 | 19 | | | | | down | | Dehydrogenase/reductase (SDR family) member 10 |
| Hs.443673 | BC008143 | KIAA1002 | 12;1 | | | down | | | | KIAA1002 protein |
| Hs.529630 | BC008625 | | 3 | | | | | | down | Homo sapiens, clone IMAGE:4183899, mRNA |
| Hs.534483 | BC008630 | MGC2941 | 17 | up | | | | | | Hypothetical protein MGC2941 |
| Hs.516859 | BC008667 | PANK2 | 20 | | down | | | | | Pantothenate kinase 2 (Hallervorden-Spatz syndrome) |
| Hs.11923 | BC009674 | DJ167A19.1 | 1;2 | up | | | up | | | Hypothetical protein DJ167A19.1 |
| Hs.447579 | BC010538 | LOC339290 | 18 | | | | | up | | Hypothetical protein LOC339290 |
| Hs.103555 | BC011054 | FLJ14775 | 17 | | | down | | | | Hypothetical protein FLJ14775 |
| Hs.194408 | BC014227 | KIAA1244 | 6 | up | | | | | | KIAA1244 |
| Hs.50823 | BC014604 | PDCD6 | 5 | down | | | | | | Programmed cell death 6 |
| Hs.129837 | BC015067 | ZBTB8 | 1 | up | | | | down | | Zinc finger and BTB domain containing 8 |
| Hs.445113 | BC015910 | MARCH-JI | 19 | up | | up | | | | Membrane-associated RING-CH protein II |
| Hs.487325 | BC016285 | PRKACB | 1 | | up | | | | down | Protein kinase, cAMP-dependent, catalytic, beta |
| Hs.536470 | BC016735 | LOC63929 | 22 | | up | | | | down | Hypothetical protein LOC63929 |
| Hs.279908 | BC017788 | TFB1M | 6 | | | | | down | | Transcription factor B1, mitochondrial |
| Hs.517792 | BC019303 | C3orf10 | 3 | up | | | | up | | Chromosome 3 open reading frame 10 |
| Hs.499145 | BC019602 | YME1L1 | 10 | down | | | | | | YME1-like 1 (S. cerevisiae) |
| Hs.350268 | BC020516 | IRF2BP2 | 1 | | | up | | | | Interferon regulatory factor 2 binding protein 2 |
| Hs.197922 | BC020630 | CaMKIINalpha | 1 | | | | up | | | Calcium/calmodulin-dependent protein kinase II |
| Hs.208961 | BC021961 | NSD1 | 5 | | | | | down | | Nuclear receptor binding SET domain protein 1 |
| Hs.525588 | BC023543 | MEG3 | 14 | | | | | | up | Maternally expressed 3 |
| Hs.436568 | BC024272 | CD74 | 5 | | down | | down | | | CD74 antigen (invariant polypeptide of major histocompatibility complex, class II antigen-associated) |
| Hs.180933 | BC029922 | CXXC1 | 18 | | | | | up | | CXXC finger 1 (PHD domain) |
| Hs.535810 | BC030122 | | 5 | up | | | | | | CDNA clone IMAGE:4814828, partial cds |
| Hs.74655 | BC033998 | LOC124512 | 17 | up | | | | | | Hypothetical protein LOC124512 |
| Hs.479099 | BC035257 | SORCS2 | 4 | up | | | | | | Sortilin-related VPS10 domain containing receptor 2 |

| UniGene ID | Annotation | | | Direction of Change in SZ relative to Controls | | | | | | Name |
|---|---|---|---|---|---|---|---|---|---|---|
| | Acc | Symbol | Chr. | AnCg | CB | DLPFC | Nacc | PC | STG | |
| Hs.459070 | BC036099 | ARNT2 | 15 | | down | | | | | Aryl-hydrocarbon receptor nuclear translocator 2 |
| Hs.302631 | BC036622 | | 7 | | | | | down | | CDNA clone IMAGE:5286843, partial cds |
| Hs.98132 | BC036875 | LCN6 | 9 | down | | | | | | Lipocalin 10 |
| Hs.127951 | BC037165 | FLJ14503 | | down | | | | | | Hypothetical protein FLJ14503 |
| Hs.90242 | BC037800 | | 1 | | up | | | | | Homo sapiens, clone IMAGE:4796172, mRNA |
| Hs.212151 | BC039075 | CLSTN3 | 12 | | | down | | | | Calsyntenin 3 |
| Hs.461074 | BC040486 | ZFP90 | 16 | | | up | | | | Zinc finger protein 90 homolog (mouse) |
| Hs.516853 | BC041916 | C20orf194 | 20 | up | | up | | | | Chromosome 20 open reading frame 194 |
| Hs.506309 | BC041930 | EEA1 | 12 | | | | | down | | Early endosome antigen 1, 162kD |
| Hs.536567 | BC042073 | | | | | | | | up | Data not found |
| Hs.205865 | BC042754 | LOC143458 | | | | | | | down | Hypothetical protein LOC143458 |
| Hs.434418 | BC042833 | MYT1L | 2 | | | | up | | | Myelin transcription factor 1-like |
| Hs.122110 | BC043568 | FLJ33718 | 4 | | up | | | | | Hypothetical protein FLJ33718 |
| Hs.413416 | BC047331 | JMJD1C | 10 | | | | | down | | Jumonji domain containing 1C |
| Hs.136888 | BC047477 | LOC338758 | 12 | | up | | | | | Hypothetical protein LOC338758 |
| Hs.443258 | BC051799 | SREBF2 | 22 | up | | | | | | Sterol regulatory element binding transcription factor 2 |
| Hs.169182 | BC052964 | KIF21B | 1;19;16 | | | | | | up | Kinesin family member 21B |
| Hs.509314 | BC059410 | LOC285148 | 2 | | | down | | down | | Hypothetical protein LOC285148 |
| Hs.180714 | BC064523 | 15E1.2 | 12 | down | | | | | | Hypothetical protein 15E1.2 |
| Hs.519904 | BC065748 | RBM24 | 6 | | | | | down | | RNA binding motif protein 24 |
| Hs.459590 | BC066358 | CCL27 | 9 | | | down | | | | Chemokine (C-C motif) ligand 27 |
| Hs.433150 | BC067884 | | 1 | | | | | | up | CDNA clone IMAGE:4480427, partial cds |
| Hs.506458 | BC068451 | EB-1 | 12 | | up | | | | | E2a-Pbx1-associated protein |
| Hs.86508 | BC079833 | | 5 | | down | | | | | CDNA clone IMAGE:4841343, partial cds |
| Hs.12862 | BC080181 | RFNG | 17 | up | | | | | | Radical fringe homolog (Drosophila) |
| Hs.115284 | BC080572 | ZNF213 | 16 | | | | | | up | Zinc finger protein 213 |
| Hs.143587 | BE467201 | | | | | | | down | | Transcribed locus |
| Hs.102471 | BE538923 | PHACTR2 | 6 | down | | | | | | Phosphatase and actin regulator 2 |
| Hs.127486 | BE551624 | | 2 | | | | | down | | Transcribed locus |
| Hs.21691 | BE671266 | GPR75 | 2 | down | | | | | | G protein-coupled receptor 75 |
| Hs.188594 | BE889301 | | 9 | | up | | | | | Transcribed locus |
| Hs.118526 | BF056604 | | | down | | | | | | Transcribed locus |
| Hs.225598 | BF059209 | | 6 | | | | | | up | Transcribed locus |
| Hs.144022 | BF109731 | FDFT1 | 8 | | up | | | | | Farnesyl-diphosphate farnesyltransferase 1 |

| Annotation | | | Direction of Change in SZ relative to Controls | | | | | | |
|---|---|---|---|---|---|---|---|---|---|
| UniGene ID | Acc | Symbol | Chr. | AnCg | CB | DLPFC | Nacc | PC | STG | Name |
| Hs.464848 | BF378154 | B4GALT6 | 18 | | up | | | | | UDP-Gal:betaGlcNAc beta 1,4- galactosyltransferase, polypeptide 6 |
| Hs.432792 | BF439526 | CBLL1 | 7 | | | up | | | | Cas-Br-M (murine) ecotropic retroviral transforming sequence-like 1 |
| Hs.478465 | BG707584 | FLJ12748 | 3 | | up | | | | | Hypothetical protein FLJ12748 |
| Hs.434375 | BI820698 | PTPRB | 12 | | | | | down | down | Protein tyrosine phosphatase, receptor type, B |
| Hs.414028 | BM455428 | C9orf16 | 9;3 | up | | | | | | Chromosome 9 open reading frame 116 |
| Hs.469967 | BM557121 | | | | | up | | | | Transcribed locus |
| Hs.445247 | BM682460 | | 5 | | | | | down | | Transcribed locus, weakly similar to NP_703324.1 Plasmodium falciparum 3D7 MAL1P3.06 gene |
| Hs.133469 | BM719738 | GOLGA1 | 9 | | | down | | | | Golgi autoantigen, golgin subfamily a, 1 |
| Hs.479766 | BP225938 | TPARL | 4 | | | | | | down | TPA regulated locus |
| Hs.470882 | BQ002778 | CALCRL | 2 | | down | | | | | Calcitonin receptor-like |
| Hs.118769 | BQ003501 | | 2 | | | | | down | | Transcribed locus |
| Hs.229304 | BQ007533 | | | | | | | | down | Transcribed locus |
| Hs.487648 | BQ285965 | SNX13 | 7 | | | up | | down | | Sorting nexin 13 |
| Hs.104980 | BQ331336 | | | | | | | | | Data not found |
| Hs.479808 | BQ477415 | IGFBP7 | 4 | | | | down | down | | Insulin-like growth factor binding protein 7 |
| Hs.179238 | BU674160 | LRRC6 | 8 | | | up | | down | | Leucine rich repeat containing 6 |
| Hs.31903 | BU685761 | | 3 | | | | | down | | Transcribed locus |
| Hs.28199 | BX091447 | | 7 | | | down | | down | | Transcribed locus |
| Hs.445015 | BX093081 | GRIN2D | | | up | | | | up | Glutamate receptor, ionotropic, N-methyl D-aspartate 2D |
| Hs.7413 | BX097190 | | 3 | | | | | up | | Transcribed locus |
| Hs.452398 | BX099722 | | 2 | down | | | | | | MRNA; cDNA DKFZp564E143 (from clone DKFZp564E143) |
| Hs.4817 | BX537377 | OPCML | 11 | | | | up | | | Opioid binding protein/cell adhesion molecule-like |
| Hs.482363 | BX537394 | SLC30A5 | 5 | | down | | | | | Solute carrier family 30 (zinc transporter), member 5 |
| Hs.343522 | BX537745 | ATP2B4 | 1;14 | | up | | | | | ATPase, Ca++ transporting, plasma membrane 4 |
| Hs.479853 | BX537946 | EPHA5 | 4 | up | up | | | | | EPH receptor A5 |
| Hs.370510 | BX538269 | IGSF4 | 11 | | up | | | | | Immunoglobulin superfamily, member 4 |
| Hs.192221 | BX538289 | ELL2 | | up | | | | | | Elongation factor, RNA polymerase II, 2 |
| Hs.494178 | BX647070 | RORB | 9 | | | up | | | | RAR-related orphan receptor B |
| Hs.433381 | BX647220 | C6orf89 | 6 | | | up | | | | Chromosome 6 open reading frame 89 |
| Hs.310545 | BX647240 | SYT1 | 12 | | | | up | | | Synaptotagmin I |
| Hs.436142 | BX647689 | PTPN13 | 4 | up | | | | | | Protein tyrosine phosphatase, non-receptor type 13 (APO- |

| | Annotation | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.369978 | BX647773 | GTDC1 | 2 | | | | | up | | 1/CD95 (Fas)-associated phosphatase) |
| Hs.146542 | BX648027 | NEGR1 | 1 | | up | | | | | Glycosyltransferase-like 1 |
| Hs.213050 | BX648050 | ELAVL4 | 1 | | up | | | | | Neuronal growth regulator 1 |
| | | | | | | | | | | ELAV (embryonic lethal, abnormal vision, Drosophila)-like 4 (Hu antigen D) |
| Hs.175343 | BX648778 | PIK3C2A | 11 | | down | | down | | | Phosphoinositide-3-kinase, class 2, alpha polypeptide |
| Hs.306423 | CA440056 | LOC339524 | 1 | | | | | up | | Hypothetical protein LOC339524 |
| Hs.327736 | CA442378 | KIF5B | 10 | | | up | | | | Kinesin family member 5B |
| Hs.537332 | CB996893 | CNOT6L | 4 | | | | | down | | CCR4-NOT transcription complex, subunit 6-like |
| Hs.105636 | CD639734 | | 1 | | down | | | | | Transcribed locus |
| Hs.443031 | CK300949 | GLB1 | 3 | | | | | | up | Galactosidase, beta 1 |
| Hs.437611 | CK820590 | | X | | | | up | | | Transcribed locus |
| Hs.29802 | CN260580 | SLIT2 | 4 | | | | | down | | Slit homolog 2 (Drosophila) |
| Hs.444818 | CR456854 | CGGBP1 | 3;12 | down | | | | | | CGG triplet repeat binding protein 1 |
| Hs.500333 | CR596764 | C10orf58 | 10 | | | | | up | | Chromosome 10 open reading frame 58 |
| Hs.301296 | CR616826 | | 13 | | down | | | | | CDNA: FLJ23131 fis, clone LNG08502 |
| Hs.120446 | CR623819 | ZCWCC1 | 22 | | | | down | | | Zinc finger, CW type with coiled-coil domain 1 |
| Hs.250072 | CR627428 | SLC4A7 | 3 | | up | | | | | Solute carrier family 4, sodium bicarbonate cotransporter, member 7 |
| Hs.477134 | CR749341 | DKFZP434F2021 | 3 | | down | | | | | DKFZP434F2021 protein |
| Hs.118351 | D13635 | UBE3C | 7 | | | | up | | | Ubiquitin protein ligase E3C |
| Hs.35804 | D25215 | HERC3 | 4;8 | | up | | | | | Hect domain and RLD 3 |
| Hs.423163 | D87969 | SLC35A1 | 6 | up | | | | | | Solute carrier family 35 (CMP sialic acid transporter), member A1 |
| Hs.536256 | F01952 | GNAZ | 22 | | | down | | up | | Guanine nucleotide binding protein (G protein), alpha z polypeptide |
| Hs.538896 | F02333 | ANKRD10 | 13 | | | | | down | | Ankyrin repeat domain 10 |
| Hs.27996 | F10010 | | 4 | | down | | | down | | Transcribed locus |
| Hs.492212 | H95037 | DECR1 | 8 | | up | | | | | 2,4-dienoyl CoA reductase 1, mitochondrial |
| Hs.131711 | J03620 | DLD | 7 | | down | | | | | Dihydrolipoamide dehydrogenase (E3 component of pyruvate dehydrogenase complex, 2-oxo-glutarate complex, branched chain keto acid dehydrogenase complex) |
| Hs.449451 | K02885 | | | down | | | | | | Isolate 971.4_G01 T cell receptor beta (TCBRV) |

| Annotation | | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.274873 | L06845 | CARS | 11 | | | | | up | | Cysteinyl-tRNA synthetase |
| Hs.220629 | L17000 | CAMK4 | 5 | | | | up | | | Calcium/calmodulin-dependent protein kinase IV |
| Hs.196983 | M61199 | SSFA2 | 2 | | | | | down | | Sperm specific antigen 2 |
| Hs.212838 | NM_000014 | A2M | 12 | | | down | | down | | Alpha-2-macroglobulin |
| Hs.232375 | NM_000019 | ACAT1 | 11 | up | | | | | | Acetyl-Coenzyme A acetyltransferase 1 (acetoacetyl Coenzyme A thiolase) |
| Hs.207776 | NM_000027 | AGA | 4 | | | | down | | down | Aspartylglucosaminidase |
| Hs.445358 | NM_000042 | APOH | 17 | down | up | | | | | Apolipoprotein H (beta-2-glycoprotein I) |
| Hs.160786 | NM_000050 | ASS | 9 | up | | | | | | Argininosuccinate synthetase |
| Hs.169348 | NM_000057 | BLM | 15 | down | | | | | | Bloom syndrome |
| Hs.476218 | NM_000094 | COL7A1 | 3 | down | | | | | | Collagen, type VII, alpha 1 (epidermolysis bullosa, dystrophic, dominant and recessive) |
| Hs.304682 | NM_000099 | CST3 | 20;11;22;12 | | down | | | | | Cystatin C (amyloid angiopathy and cerebral hemorrhage) |
| Hs.335513 | NM_000129 | F13A1 | 6 | | down | | | | | Coagulation factor XIII, A1 polypeptide |
| Hs.255230 | NM_000181 | GUSB | 7 | | | | | | down | Glucuronidase, beta |
| Hs.303154 | NM_000202 | IDS | X;12 | | | up | | | | Iduronate 2-sulfatase (Hunter syndrome) |
| Hs.224012 | NM_000214 | JAG1 | 20 | | down | down | | | | Jagged 1 (Alagille syndrome) |
| Hs.156519 | NM_000251 | MSH2 | 2 | | down | | | | | MutS homolog 2, colon cancer, nonpolyposis type 1 (E. coli) |
| Hs.21213 | NM_000259 | MYO5A | 15 | | up | | up | | | Myosin VA (heavy polypeptide 12, myoxin) |
| Hs.181272 | NM_000297 | PKD2 | 4 | | | down | down | | | Polycystic kidney disease 2 (autosomal dominant) |
| Hs.476595 | NM_000333 | ATXN7 | 3 | | down | | down | | down | Ataxin 7 |
| Hs.271771 | NM_000345 | SNCA | 4 | | | | up | | | Synuclein, alpha (non A4 component of amyloid precursor) |
| Hs.370771 | NM_000389 | CDKN1A | 6;9 | | | | down | | | Cyclin-dependent kinase inhibitor 1A (p21, Cip1) |
| Hs.2785 | NM_000422 | KRT17 | 17 | down | | | | | | Keratin 17 |
| Hs.250769 | NM_000478 | ALPL | 1 | down | | | | | | Alkaline phosphatase, liver/bone/kidney |
| Hs.24422 | NM_000538 | RFXAP | 13 | | | up | | | | Regulatory factor X-associated protein |
| Hs.529400 | NM_000629 | IFNAR1 | 21 | | | | | | up | Interferon (alpha, beta and omega) receptor 1 |
| Hs.150749 | NM_000633 | BCL2 | 18 | | | | | | up | B-cell CLL/lymphoma 2 |
| Hs.336046 | NM_000640 | IL13RA2 | X | | | | up | | | Interleukin 13 receptor, alpha 2 |
| Hs.150749 | NM_000657 | BCL2 | 18 | | | | | | up | B-cell CLL/lymphoma 2 |
| Hs.334707 | NM_000666 | ACY1 | 3;1 | down | | | | | down | Aminoacylase 1 |

| Annotation | | | Direction of Change in SZ relative to Controls | | | | | | Name |
|---|---|---|---|---|---|---|---|---|---|
| UniGene ID | Acc | Symbol | Chr. | AnCg | CB | DLPFC | Nacc | PC | STG | |
| Hs.197029 | NM_000675 | ADORA2A | 22 | | | | up | | | Adenosine A2a receptor |
| Hs.388004 | NM_000687 | AHCY | 20;16 | up | | | | up | | S-adenosylhomocysteine hydrolase |
| Hs.34114 | NM_000702 | ATP1A2 | 1 | | down | | | | | ATPase, Na+/K+ transporting, alpha 2 (+) polypeptide |
| Hs.433307 | NM_000709 | BCKDHA | 19,1 | | down | | | | | Branched chain keto acid dehydrogenase E1, alpha polypeptide (maple syrup urine disease) |
| Hs.282871 | NM_000770 | CYP2C8 | 10 | | up | | | | | Cytochrome P450, family 2, subfamily C, polypeptide 8 |
| Hs.152096 | NM_000775 | CYP2J2 | 1 | | | | | up | | Cytochrome P450, family 2, subfamily J, polypeptide 2 |
| Hs.202354 | NM_000793 | DIO2 | 14 | down | | | | | | Deiodinase, iodothyronine, type II |
| Hs.175934 | NM_000806 | GABRA1 | 5;17 | | | | up | | | Gamma-aminobutyric acid (GABA) A receptor, alpha 1 |
| Hs.473648 | NM_000819 | GART | 21 | | | | up | | | Phosphoribosylglycinamide formyltransferase, phosphoribosylglycinamide synthetase, phosphoribosylaminoimidazole synthetase |
| Hs.32945 | NM_000838 | GRM1 | 6 | | up | | | | | Glutamate receptor, metabotropic 1 |
| Hs.268573 | NM_000853 | GSTT1 | 22 | | | down | | | | Glutathione S-transferase theta 1 |
| Hs.376933 | NM_000858 | GUK1 | 1 | | | | up | | | Guanylate kinase 1 |
| Hs.46732 | NM_000898 | MAOB | X | up | | up | | | | Monoamine oxidase B |
| Hs.2820 | NM_000916 | OXTR | 3 | | | | | | up | Oxytocin receptor |
| Hs.354056 | NM_000941 | POR | 7 | | | | | up | | P450 (cytochrome) oxidoreductase |
| Hs.446429 | NM_000954 | PTGDS | 9;11,1; 7;6;14; 2;19,1 7;3;16; 22 | | down | | down | | | Prostaglandin D2 synthase 21kDa (brain) |
| Hs.374588 | NM_000985 | RPL17 | 18;1; 15;3 | up | | | | | | Ribosomal protein L17 |
| Hs.529631 | NM_000996 | RPL35A | 3 | up | | up | | | | Ribosomal protein L35a |
| Hs.134846 | NM_001001 | MGC24381 | 16 | up | | | | | | Hypothetical protein MGC24381 |
| Hs.492031 | NM_001001 410 | FLJ11011 | 8 | | | | | | up | Hypothetical protein FLJ11011 |
| Hs.188569 | NM_001001 482 | ZDHHC13 | 11 | | | | | down | | Zinc finger, DHHC domain containing 13 |
| Hs.429 | NM_001001 483 | ATP5G3 | 2 | up | | | | | | ATP synthase, H+ transporting, mitochondrial F0 complex, subunit c (subunit 9) isoform 3 |
| Hs.430439 | NM_001002 258 | HIRIP5 | 2 | | | | up | | | HIRA interacting protein 5 |
| | NM_001002 757 | | | | | | | | | |

| Annotation | | | Direction of Change in SZ relative to Controls | | | | | | |
|---|---|---|---|---|---|---|---|---|---|
| UniGene ID | Acc | Symbol | Chr. | AnCg | CB | DLPFC | Nacc | PC | STG | Name |
| Hs.92423 | NM_001002838 | PRKWNK3 | 9 | down | | | | | | Protein kinase, lysine deficient 3 |
| Hs.522418 | NM_001003722 | GLE1L | 7 | up | | | | | | GLE1 RNA export mediator-like (yeast) |
| Hs.444445 | NM_001003802 | SMARCD3 | 16 | | | | up | | | SWI/SNF related, matrix associated, actin dependent regulator of chromatin, subfamily d, member 3 |
| Hs.528826 | NM_001004300 | LOC124411 | 17 | down | | | | | | Hypothetical protein LOC124411 |
| Hs.462230 | NM_001004313 | LOC388335 | 1 | | | | | down | | Similar to RIKEN cDNA A730055C05 gene |
| Hs.405925 | NM_001005290 | DDA3 | 19;15;2 | up | | | | | | Differential display and activated by p53 |
| Hs.446623 | NM_001005335 | HNRPL | 12 | down | | | down | | | Heterogeneous nuclear ribonucleoprotein L |
| Hs.438219 | NM_001005408 | KIAA1787 | 15 | | up | | | up | | G protein pathway suppressor 2 |
| Hs.334873 | NM_001005502 | CPM | 5 | | down | | | up | | Carboxypeptidase M |
| Hs.445841 | NM_001036 | RYR3 | 3 | | down | | | | | Ryanodine receptor 3 |
| Hs.162585 | NM_001046 | SLC12A2 | 17 | down | up | | | | down | Solute carrier family 12 (sodium/potassium/chloride transporters), member 2 |
| Hs.12409 | NM_001048 | SST | 12 | | | down | | | | Somatostatin |
| Hs.159306 | NM_001092 | ABR | 22 | | | | up | | | Active BCR-related gene |
| Hs.274361 | NM_001095 | ACCN2 | 2 | | | down | | | | Amiloride-sensitive cation channel 2, neuronal |
| Hs.474982 | NM_001098 | ACO2 | 16 | | | up | up | | | Aconitase 2, mitochondrial |
| Hs.470316 | NM_001105 | ACVR1 | 4 | down | | | | | | Activin A receptor, type I |
| Hs.461253 | NM_001128 | AP1G1 | 5 | up | | | | | | Adaptor-related protein complex 1, gamma 1 subunit |
| Hs.480653 | NM_001154 | ANXA5 | 13 | | | | down | | | Annexin A5 |
| Hs.483239 | NM_001182 | ALDH7A1 | 12 | up | | | down | | | Aldehyde dehydrogenase 7 family, member A1 |
| Hs.25447 | NM_001268 | CHC1L | 14 | | | | down | | | Chromosome condensation 1-like |
| Hs.162233 | NM_001273 | CHD4 | 18 | | | up | | | | Chromodomain helicase DNA binding protein 4 |
| Hs.150793 | NM_001275 | CHGA | 4 | | | | up | | | Chromogranin A (parathyroid secretory protein 1) |
| Hs.249129 | NM_001279 | CIDEA | 12 | | | | | up | | Cell death-inducing DFFA-like effector a |
| Hs.23748 | NM_001290 | LDB2 | 12 | | | | up | | | LIM domain binding 2 |
| Hs.13313 | NM_001310 | CREBL2 | 11;16 | | down | | | | | CAMP responsive element binding protein-like 2 |
| Hs.166011 | NM_001331 | CTNND1 | | | | down | | down | | Catenin (cadherin-associated protein), delta 1 |

| Annotation | | | | Direction of Change in SZ relative to Controls | | | | | | | |
|---|---|---|---|---|---|---|---|---|---|---|---|
| UniGene ID | Acc | Symbol | Chr. | AnCg | CB | DLPFC | Nacc | PC | STG | Name | |
| Hs.336916 | NM_001350 | DAXX | 19 | | down | | | up | | Death-associated protein 6 | |
| Hs.159195 | NM_001380 | DOCK1 | 6 | | | | down | | | Dedicator of cytokinesis 1 | |
| Hs.117060 | NM_001393 | ECM2 | 10 | | down | | | | | Extracellular matrix protein 2, female organ and adipocyte specific | |
| Hs.196176 | NM_001398 | ECH1 | 19;X | up | | | | | | Enoyl Coenzyme A hydratase 1, peroxisomal | |
| Hs.132483 | NM_001410 | EGFL4 | 19 | up | | | | | | EGF-like-domain, multiple 4 | |
| Hs.299002 | NM_001436 | FBL | 19 | | | | down | | | Fibrillarin | |
| Hs.357637 | NM_001439 | EXTL2 | 1 | | | down | | | | Exostoses (multiple)-like 2 | |
| Hs.272011 | NM_001497 | B4GALT1 | 9 | | up | | | | | UDP-Gal:betaGlcNAc beta 1,4- galactosyltransferase, polypeptide 1 | |
| Hs.47338 | NM_001549 | IFIT3 | 10 | down | | | | | | Interferon-induced protein with tetratricopeptide repeats 3 | |
| Hs.469386 | NM_001566 | INPP4A | 2 | | | up | | | | Inositol polyphosphate-4-phosphatase, type I, 107kDa | |
| Hs.289795 | NM_001584 | C11orf8 | 11 | | up | | | down | | Chromosome 11 open reading frame 8 | |
| Hs.166160 | NM_001607 | ACAA1 | 3 | | | | | | down | Acetyl-Coenzyme A acyltransferase 1 (peroxisomal 3- oxoacyl-Coenzyme A thiolase) | |
| Hs.368486 | NM_001649 | APXL | X | up | up | | | | | Apical protein-like (Xenopus laevis) | |
| Hs.286221 | NM_001658 | ARF1 | 1;19 | | down | | | | | ADP-ribosylation factor 1 | |
| Hs.3109 | NM_001666 | ARHGAP4 | X | | up | | | | | Rho GTPase activating protein 4 | |
| Hs.413137 | NM_001680 | FXYD2 | 11 | | | | | up | | FXYD domain containing ion transport regulator 2 | |
| Hs.198365 | NM_001724 | BPGM | 7 | | | up | | | | 2,3-bisphosphoglycerate mutase | |
| Hs.274873 | NM_001751 | CARS | 11 | | | | | up | | Cysteinyl-tRNA synthetase | |
| Hs.445570 | NM_001780 | CD63 | 12;X | | | | down | | | CD63 antigen (melanoma 1 antigen) | |
| Hs.170129 | NM_001821 | CHML | 1 | | | | | down | | Choroideremia-like (Rab escort protein 2) | |
| Hs.129966 | NM_001842 | CNTFR | 9 | | | | down | | | Ciliary neurotrophic factor receptor | |
| Hs.421621 | NM_001864 | COX7A1 | 19 | | | | | | down | Cytochrome c oxidase subunit VIIa polypeptide 1 (muscle) | |
| Hs.2242 | NM_001891 | CSN2 | 4 | down | | | | | | Casein beta | |
| Hs.410037 | NM_001901 | CTGF | 6;16 | | down | | | | | Connective tissue growth factor | |
| Hs.465413 | NM_001914 | CYB5 | 18 | | | up | | | | Cytochrome b-5 | |
| Hs.113227 | NM_001917 | DAO | 12 | | down | | | | | D-amino-acid oxidase | |
| Hs.433839 | NM_001958 | EEF1A2 | 20;19, 17;9 | | | | up | | | Eukaryotic translation elongation factor 1 alpha 2 | |
| Hs.326035 | NM_001964 | EGR1 | 5 | down | | | | down | | Early growth response 1 | |
| Hs.306251 | NM_001982 | ERBB3 | 12 | | | | down | | | V-erb-b2 erythroblastic leukemia viral oncogene homolog | |

| UniGene ID | Annotation Acc | Symbol | Chr. | AnCg | CB | DLPFC | Nacc | PC | STG | Name |
|---|---|---|---|---|---|---|---|---|---|---|
| Hs.370666 | NM_002015 | FOXO1A | 13 | down | | | down | | | Forkhead box O1A (rhabdomyosarcoma) |
| Hs.103183 | NM_002024 | FMR1 | X | | down | | | down | | Fragile X mental retardation 1 |
| Hs.62661 | NM_002053 | GBP1 | 1 | | | down | | | | Guanylate binding protein 1, interferon-inducible, 67kDa |
| Hs.430425 | NM_002074 | GNB1 | 1 | | | | up | | | Guanine nucleotide binding protein (G protein), beta polypeptide 1 |
| Hs.309763 | NM_002092 | GRSF1 | 4;17 | up | down | | | | | G-rich RNA sequence binding factor 1 |
| Hs.445733 | NM_002093 | GSK3B | 3 | down | | | | | | Glycogen synthase kinase 3 beta |
| Hs.181244 | NM_002116 | HLA-A | 6;2;19 | | down | down | down | | | Major histocompatibility complex, class I, A |
| Hs.32309 | NM_002194 | INPP1 | 2 | | | | | | down | Inositol polyphosphate-1-phosphatase |
| Hs.374097 | NM_002199 | IRF2 | 4 | | | | down | | | Interferon regulatory factor 2 |
| Hs.25292 | NM_002229 | JUNB | 19 | | down | | | | down | Jun B proto-oncogene |
| Hs.408960 | NM_002241 | KCNJ10 | 1 | | | | | | down | Potassium inwardly-rectifying channel, subfamily J, member 10 |
| Hs.41696 | NM_002277 | KRTHA1 | 17 | | down | | | | | Keratin, hair, acidic, 1 |
| Hs.159590 | NM_002347 | LY6H | 8 | up | up | | up | | | Lymphocyte antigen 6 complex, locus H |
| Hs.388613 | NM_002499 | NEO1 | 15 | | | | | up | | Neogenin homolog 1 (chicken) |
| Hs.444934 | NM_002525 | NRD1 | 1 | up | | | up | | | Nardilysin (N-arginine dibasic convertase) |
| Hs.153952 | NM_002526 | NT5E | 6;3 | | | | | | down | 5'-nucleotidase, ecto (CD73) |
| Hs.467701 | NM_002539 | ODC1 | 2 | up | | | | | | Ornithine decarboxylase 1 |
| Hs.435714 | NM_002576 | PAK1 | 11 | | up | | | | | P21/Cdc42/Rac1-activated kinase 1 (STE20 homolog, yeast) |
| Hs.483564 | NM_002622 | PFDN1 | 5 | | | down | | | | Prefoldin 1 |
| Hs.464071 | NM_002631 | PGD | 1 | up | | | | | | Phosphogluconate dehydrogenase |
| Hs.468415 | NM_002643 | PIGF | 2 | up | | up | | | | Phosphatidylinositol glycan, class F |
| Hs.444975 | NM_002656 | PLAGL1 | 6 | | up | | | up | up | Pleiomorphic adenoma gene-like 1 |
| Hs.2868 | NM_002677 | PMP2 | 8 | | down | | | | | Peripheral myelin protein 2 |
| Hs.321234 | NM_002685 | EXOSC10 | 1 | up | | | | | | Exosome component 10 |
| Hs.331420 | NM_002703 | PPAT | 4 | | down | down | | | down | Phosphoribosyl pyrophosphate amidotransferase |
| Hs.484371 | NM_002752 | MAPK9 | 5 | down | | | | | | Mitogen-activated protein kinase 9 |
| Hs.461777 | NM_002768 | PCOLN3 | 16 | up | up | | | up | | Procollagen (type III) N-endopeptidase |
| Hs.368121 | NM_002788 | PSMA3 | 14 | | down | | | | | Proteasome (prosome, macropain) subunit, alpha type, 3 |
| Hs.446260 | NM_002791 | PSMA6 | 14 | | | | | | | Proteasome (prosome, macropain) subunit, alpha type, 6 |
| Hs.422990 | NM_002797 | PSMB5 | 14;Y;X | | | | | up | | Proteasome (prosome, macropain) subunit, beta type, 5 |

| | Annotation | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.386866 | NM_002841 | PTPRG | 3 | | | | | | down | Protein tyrosine phosphatase, receptor type, G |
| Hs.127657 | NM_002852 | PTX3 | 3 | | up | | | | | Pentaxin-related gene, rapidly induced by IL-1 beta |
| Hs.521640 | NM_002874 | RAD23B | 9 | | | | | down | | RAD23 homolog B (S. cerevisiae) |
| Hs.148178 | NM_002885 | RAP1GA1 | 1 | | up | | | | | RAP1, GTPase activating protein 1 |
| Hs.423935 | NM_002904 | RDBP | 11;6 | up | down | | | | | RD RNA binding protein |
| Hs.370620 | NM_002908 | REL | 2 | | down | | | | | V-rel reticuloendotheliosis viral oncogene homolog (avian) |
| Hs.115474 | NM_002915 | RFC3 | 13 | | up | | | | | Replication factor C (activator 1) 3, 38kDa |
| Hs.23978 | NM_002967 | SAFB | 19;Y | | down | | | | | Scaffold attachment factor B |
| Hs.135787 | NM_002968 | SALL1 | 16 | | | | down | | | Sal-like 1 (Drosophila) |
| Hs.280202 | NM_002972 | SBF1 | 22 | up | | | | | | SET binding factor 1 |
| Hs.465924 | NM_003000 | SDHB | 1 | up | | | | | | Succinate dehydrogenase complex, subunit B, iron sulfur (Ip) |
| Hs.433795 | NM_003029 | SHC1 | 1;6 | up | | | | | | SHC (Src homology 2 domain containing) transforming protein 1 |
| Hs.323878 | NM_003038 | SLC1A4 | 2 | | | | down | | | Solute carrier family 1 (glutamate/neutral amino acid transporter), member 4 |
| Hs.443874 | NM_003042 | SLC6A1 | 3 | | | | | down | | Solute carrier family 6 (neurotransmitter transporter, GABA), member 1 |
| Hs.334629 | NM_003063 | SLN | 11 | | up | | | | | Sarcolipin |
| Hs.360174 | NM_003068 | SNAI2 | 8 | | up | | | | | Snail homolog 2 (Drosophila) |
| Hs.1063 | NM_003093 | SNRPC | 6 | up | | | | | | Small nuclear ribonucleoprotein polypeptide C |
| Hs.185597 | NM_003119 | SPG7 | 16 | | down | | | | | Spastic paraplegia 7, paraplegin (pure and complicated autosomal recessive) |
| Hs.443861 | NM_003137 | SRPK1 | 6 | | | up | | | | SFRS protein kinase 1 |
| Hs.288229 | NM_003165 | STXBP1 | 9 | | | | up | | | Syntaxin binding protein 1 |
| Hs.482390 | NM_003243 | TGFBR3 | 1 | down | | | | | | Transforming growth factor, beta receptor III (betaglycan, 300kDa) |
| Hs.104839 | NM_003255 | TIMP2 | 17 | up | | | | | | Tissue inhibitor of metalloproteinase 2 |
| Hs.332173 | NM_003260 | TLE2 | 19 | up | | | | | up | Transducin-like enhancer of split 2 (E(sp1) homolog, Drosophila) |
| Hs.432424 | NM_003291 | TPP2 | 13 | | down | | | | | Tripeptidyl peptidase II |
| Hs.12084 | NM_003321 | TUFM | 16 | | | | | | | Tu translation elongation factor, mitochondrial |
| Hs.439672 | NM_003378 | VGF | 7 | | down | | | | down | VGF nerve growth factor inducible |
| Hs.388927 | NM_003403 | YY1 | 14 | | | up | | | | YY1 transcription factor |

| Annotation | | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.399810 | NM_003422 | ZNF42 | 19 | | up | | | | | Zinc finger protein 42 (myeloid-specific retinoic acid-responsive) |
| Hs.172979 | NM_003451 | ZNF177 | 19 | up | | | | | | Zinc finger protein 177 |
| Hs.144442 | NM_003561 | PLA2G10 | 16 | up | | | | | | Phospholipase A2, group X |
| Hs.36958 | NM_003567 | BCAR3 | 1 | | down | | down | | | Breast cancer anti-estrogen resistance 3 |
| Hs.371698 | NM_003610 | RAE1 | 20 | up | | | | | | RAE1 RNA export 1 homolog (S. pombe) |
| Hs.250072 | NM_003615 | SLC4A7 | 3 | | up | | | | | Solute carrier family 4, sodium bicarbonate cotransporter, member 7 |
| Hs.104925 | NM_003633 | ENC1 | 5 | | | | up | | | Ectodermal-neural cortex (with BTB-like domain) |
| Hs.104576 | NM_003654 | CHST1 | 11 | up | | | | | | Carbohydrate (keratan sulfate Gal-6) sulfotransferase 1 |
| Hs.400556 | NM_003657 | BCAS1 | 20 | | up | | | | | Breast carcinoma amplified sequence 1 |
| Hs.161181 | NM_003675 | PRPF18 | 10 | | down | down | | | | PRP18 pre-mRNA processing factor 18 homolog (yeast) |
| Hs.22393 | NM_003677 | DENR | 12 | | | | up | | | Density-regulated protein |
| Hs.213264 | NM_003680 | YARS | 1 | | | | up | | | Tyrosyl-tRNA synthetase |
| Hs.284491 | NM_003681 | PDXK | 21 | | | up | | | | Pyridoxal (pyridoxine, vitamin B6) kinase |
| Hs.470608 | NM_003705 | SLC25A12 | 2 | | | | up | | | Solute carrier family 25 (mitochondrial carrier, Aralar), member 12 |
| Hs.484222 | NM_003729 | RTCD1 | 1 | | down | | | | | RNA terminal phosphate cyclase domain 1 |
| Hs.4742 | NM_003801 | GPAA1 | 8;6 | up | | | | | | GPAA1P anchor attachment protein 1 homolog (yeast) |
| Hs.178748 | NM_003813 | ADAM21 | 14 | down | | | | | | A disintegrin and metalloproteinase domain 21 |
| Hs.169900 | NM_003819 | PABPC4 | 1;15;X | | up | | | | | Poly(A) binding protein, cytoplasmic 4 (inducible form) |
| Hs.445511 | NM_003831 | RIOK3 | 18 | | down | | | | | RIO kinase 3 (yeast) |
| Hs.430551 | NM_003870 | IQGAP1 | 15 | | | | down | | | IQ motif containing GTPase activating protein 1 |
| Hs.7165 | NM_003904 | ZNF259 | | | up | | | | | Zinc finger protein 259 |
| Hs.429180 | NM_003908 | EIF2S2 | 20;2 | up | down | | | | up | Eukaryotic translation initiation factor 2, subunit 2 beta, 38kDa |
| Hs.121592 | NM_003916 | AP1S2 | X | down | | | | | | Adaptor-related protein complex 1, sigma 2 subunit |
| Hs.371199 | NM_003919 | SGCE | 7 | | | | down | | | Sarcoglycan, epsilon |
| Hs.200770 | NM_003930 | SCAP2 | 7 | | | up | | | | Src family associated phosphoprotein 2 |
| Hs.158460 | NM_003936 | CDK5R2 | 2 | up | | down | | | | Cyclin-dependent kinase 5, regulatory subunit 2 (p39) |
| Hs.143728 | NM_003941 | WASL | 7 | | | up | | | | Wiskott-Aldrich syndrome-like |
| Hs.47357 | NM_003956 | CH25H | 10 | down | | | | | | Cholesterol 25-hydroxylase |
| Hs.463439 | NM_003971 | SPAG9 | 17 | | down | | | | | Sperm associated antigen 9 |
| Hs.315369 | NM_004028 | AQP4 | 18 | | down | | | | | Aquaporin 4 |

| Annotation | | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.412117 | NM_004033 | ANXA6 | 5;3 | | | | up | | | Annexin A6 |
| Hs.467898 | NM_004036 | ADCY3 | 2 | | | | up | | | Adenylate cyclase 3 |
| Hs.433732 | NM_004071 | CLK1 | 2 | | | | down | | | CDC-like kinase 1 |
| Hs.292549 | NM_004087 | DLG1 | 3 | up | down | | down | | | Discs, large homolog 1 (Drosophila) |
| Hs.202095 | NM_004098 | EMX2 | 10 | | | | | down | | Empty spiracles homolog 2 (Drosophila) |
| Hs.7557 | NM_004117 | FKBP5 | 6 | | | | | up | | FK506 binding protein 5 |
| Hs.172791 | NM_004182 | UXT | X | | | | | up | | Ubiquitously-expressed transcript |
| Hs.484703 | NM_004233 | CD83 | 6 | down | | | | | | CD83 antigen (activated B lymphocytes, immunoglobulin superfamily) |
| Hs.376206 | NM_004235 | KLF4 | 9 | | | | | | down | Kruppel-like factor 4 (gut) |
| Hs.465985 | NM_004317 | ASNA1 | 19 | | | | up | | | ArsA arsenite transporter, ATP-binding, homolog 1 (bacterial) |
| Hs.471401 | NM_004328 | BCS1L | 2 | up | | up | | | | BCS1-like (yeast) |
| Hs.131226 | NM_004331 | BNIP3L | 8 | | | up | | | | BCL2/adenovirus E1B 19kDa interacting protein 3-like |
| Hs.13291 | NM_004354 | CCNG2 | 4 | | | up | | | | Cyclin G2 |
| Hs.220529 | NM_004363 | CEACAM5 | 19;4 | | up | | | up | | Carcinoembryonic antigen-related cell adhesion molecule 5 |
| Hs.129452 | NM_004392 | DACH1 | 13 | | up | up | up | | | Dachshund homolog 1 (Drosophila) |
| Hs.408461 | NM_004397 | DDX6 | 11 | | | down | | | | DEAD (Asp-Glu-Ala-Asp) box polypeptide 6 |
| Hs.171695 | NM_004417 | DUSP1 | 5;16;11 | | down | | | | down | Dual specificity phosphatase 1 |
| Hs.2128 | NM_004419 | DUSP5 | 10 | | | | | | down | Dual specificity phosphatase 5 |
| Hs.371218 | NM_004438 | EPHA4 | 2 | | | | up | | | EPH receptor A4 |
| Hs.213389 | NM_004487 | GOLGB1 | 3 | up | | | | | | Golgi autoantigen, golgin subfamily b, macrogolgin (with transmembrane signal), 1 |
| Hs.248746 | NM_004499 | HNRPAB | 5 | | down | | | | | Heterogeneous nuclear ribonucleoprotein A/B |
| Hs.472185 | NM_004552 | NDUFS5 | 1 | | | | up | | | NADH dehydrogenase (ubiquinone) Fe-S protein 5, 15kDa (NADH-coenzyme Q reductase) |
| Hs.408257 | NM_004553 | NDUFS6 | 5 | up | | | | | | NADH dehydrogenase (ubiquinone) Fe-S protein 6, 13kDa (NADH-coenzyme Q reductase) |
| Hs.119316 | NM_004564 | PET112L | 4 | | | | | | | PET112-like (yeast) |
| Hs.283454 | NM_004569 | PIGH | 14 | | | up | | up | | Phosphatidylinositol glycan, class H |
| Hs.296169 | NM_004578 | RAB4A | 1 | up | | up | | | | RAB4A, member RAS oncogene family |
| Hs.129783 | NM_004588 | SCN2B | 11 | | | | | | up | Sodium channel, voltage-gated, type II, beta |
| Hs.433201 | NM_004642 | CDK2AP1 | 12;2 | | down | | | | | CDK2-associated protein 1 |

| Annotation | | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.106674 | NM_004656 | BAP1 | 3 | up | | | | | | BRCA1 associated protein-1 (ubiquitin carboxy-terminal hydrolase) |
| Hs.194695 | NM_004675 | ARH1 | 1 | | | | | | up | Ras homolog gene family, member 1 |
| Hs.106876 | NM_004691 | ATP6V0D1 | 16 | | | | up | | | ATPase, H+ transporting, lysosomal 38kDa, V0 subunit d isoform 1 |
| Hs.471779 | NM_004735 | LRRFIP1 | 2 | | up | | | | | Leucine rich repeat (in FLII) interacting protein 1 |
| Hs.2210 | NM_004773 | TRIP3 | 17 | | | | up | | | Thyroid hormone receptor interactor 3 |
| Hs.464848 | NM_004775 | B4GALT6 | 18 | | | up | | | | UDP-Gal:betaGlcNAc beta 1,4- galactosyltransferase, polypeptide 6 |
| Hs.370487 | NM_004776 | B4GALT5 | 20 | | | | up | | | UDP-Gal:betaGlcNAc beta 1,4- galactosyltransferase, polypeptide 5 |
| Hs.26703 | NM_004779 | CNOT8 | 5 | up | down | | | | | CCR4-NOT transcription complex, subunit 8 |
| Hs.29802 | NM_004787 | SLIT2 | 4 | | | | up | | | Slit homolog 2 (Drosophila) |
| Hs.483238 | NM_004815 | PARG1 | 1 | down | | | | down | | PTPL1-associated RhoGAP 1 |
| Hs.240395 | NM_004823 | KCNK6 | 19 | | | | | up | | Potassium channel, subfamily K, member 6 |
| Hs.480218 | NM_004827 | ABCG2 | 4 | down | | down | | | | ATP-binding cassette, sub-family G (WHITE), member 2 |
| Hs.431109 | NM_004853 | STX8 | 17 | up | down | | | | | Syntaxin 8 |
| Hs.408515 | NM_004883 | NRG2 | 5 | down | | | | up | | Neuregulin 2 |
| Hs.282901 | NM_004902 | RNPC2 | 20;X | up | | | | | | RNA-binding region (RNP1, RRM) containing 2 |
| Hs.446091 | NM_004906 | WTAP | 6 | | | | | down | | Wilms tumor 1 associated protein |
| Hs.164410 | NM_004913 | C16orf7 | 16,6 | up | | | | | | Chromosome 16 open reading frame 7 |
| Hs.2171 | NM_004962 | GDF10 | 10 | | down | | down | | | Growth differentiation factor 10 |
| Hs.303870 | NM_004976 | KCNC1 | 11 | down | | | | | | Potassium voltage-gated channel, Shaw-related subfamily, member 1 |
| Hs.32505 | NM_004981 | KCNJ4 | 22 | | | down | | | | Potassium inwardly-rectifying channel, subfamily J, member 4 |
| Hs.151219 | NM_004984 | KIF5A | 12 | | | | up | | | Kinesin family member 5A |
| Hs.149387 | NM_004999 | MYO6 | 6 | | down | | down | | down | Myosin VI |
| Hs.45002 | NM_005052 | RAC3 | 17 | | | | | | up | Ras-related C3 botulinum toxin substrate 3 (rho family, small GTP binding protein Rac3) |
| Hs.46440 | NM_005075 | SLCO1A2 | 12 | | | | down | | | Solute carrier organic anion transporter family, member 1A2 |
| Hs.287362 | NM_005078 | TLE3 | 15 | | | | | | up | Transducin-like enhancer of split 3 (E(sp1) homolog, Drosophila) |
| Hs.183428 | NM_005086 | SSPN | 12 | | down | | | | | Sarcospan (Kras oncogene-associated gene) |

| Annotation | | | Direction of Change in SZ relative to Controls | | | | | | Name |
|---|---|---|---|---|---|---|---|---|---|
| UniGene ID | Acc | Symbol | Chr. | AnCg | CB | DLPFC | Nacc | PC | STG | |
| Hs.356820 | NM_005108 | XYLB | 3 | | up | | | | | Xylulokinase homolog (H. influenzae) |
| Hs.37288 | NM_005126 | NR1D2 | 3 | | | up | | | | Nuclear receptor subfamily 1, group D, member 2 |
| Hs.1540 | NM_005131 | THOC1 | 18 | | | | down | | down | THO complex 1 |
| Hs.464595 | NM_005134 | PPP4R1 | 18 | | down | | | | | Protein phosphatase 4, regulatory subunit 1 |
| Hs.410944 | NM_005138 | SCO2 | 22 | | | | | up | | SCO cytochrome oxidase deficient homolog 2 (yeast) |
| Hs.502883 | NM_005146 | SART1 | 11 | up | | | | | | Squamous cell carcinoma antigen recognised by T cells 1 |
| Hs.369438 | NM_005238 | ETS1 | 11 | | | | | down | | V-ets erythroblastosis virus E26 oncogene homolog 1 (avian) |
| Hs.481371 | NM_005245 | FAT | 4 | | | | | down | | FAT tumor suppressor homolog 1 (Drosophila) |
| Hs.25647 | NM_005252 | FOS | 14,22;11 | | down | | | | down | V-fos FBJ murine osteosarcoma viral oncogene homolog |
| Hs.483305 | NM_005340 | HINT1 | 5 | up | | | | up | | Histidine triad nucleotide binding protein 1 |
| Hs.2780 | NM_005354 | JUND | 19;5 | | | | | down | | Jun D proto-oncogene |
| Hs.380742 | NM_005393 | PLXNB3 | X | | | | | | down | Plexin B3 |
| Hs.303090 | NM_005398 | PPP1R3C | 10 | | | | down | | | Protein phosphatase 1, regulatory (inhibitor) subunit 3C |
| Hs.50732 | NM_005399 | PRKAB2 | 1 | | | | | up | up | Protein kinase, AMP-activated, beta 2 non-catalytic subunit |
| Hs.129727 | NM_005431 | XRCC2 | 7 | | down | | | | | X-ray repair complementing defective repair in Chinese hamster cells 2 |
| Hs.194148 | NM_005433 | YES1 | 18,2 | | | | down | | | V-yes-1 Yamaguchi sarcoma viral oncogene homolog 1 |
| Hs.368610 | NM_005443 | PAPSS1 | 4 | up | | | | | | 3'-phosphoadenosine 5'-phosphosulfate synthase 1 |
| Hs.198612 | NM_005458 | GPR51 | 9 | | | | up | | | G protein-coupled receptor 51 |
| Hs.278500 | NM_005471 | GNPDA1 | 5;9 | | | up | | | | Glucosamine-6-phosphate deaminase 1 |
| Hs.429294 | NM_005502 | ABCA1 | 9 | | | | down | | | ATP-binding cassette, sub-family A (ABC1), member 1 |
| Hs.153299 | NM_005510 | DOM3Z | 6 | | | | | up | | Dom-3 homolog Z (C. elegans) |
| Hs.250666 | NM_005524 | HES1 | 3 | | | | | | down | Hairy and enhancer of split 1, (Drosophila) |
| Hs.471508 | NM_005544 | IRS1 | 2 | | | | up | | | Insulin receptor substrate 1 |
| Hs.2795 | NM_005566 | LDHA | 11;17;22;10;2 | | | | up | | | Lactate dehydrogenase A |
| Hs.34560 | NM_005574 | LMO2 | 11 | | | down | | down | | LIM domain only 2 (rhombotin-like 1) |
| Hs.18069 | NM_005606 | LGMN | 14 | | | up | | | | Legumain |
| Hs.484324 | NM_005649 | ZNF354A | 5 | | | | down | | | Zinc finger protein 354A |
| Hs.183671 | NM_005651 | TDO2 | 4 | | | | | up | | Tryptophan 2,3-dioxygenase |
| Hs.458917 | NM_005697 | SCAMP2 | 15 | | | | | | down | Secretory carrier membrane protein 2 |

| Annotation | | | | Direction of Change in SZ relative to Controls | | | | | | | Name |
|---|---|---|---|---|---|---|---|---|---|---|---|
| UniGene ID | Acc | Symbol | Chr. | AnCg | CB | DLPFC | Nacc | PC | STG | | |
| Hs.21577 | NM_005701 | RNUT1 | 15 | | | | | up | | | RNA, U transporter 1 |
| Hs.118118 | NM_005723 | TM4SF9 | 4 | | | up | | | | | Transmembrane 4 superfamily member 9 |
| Hs.381072 | NM_005729 | PPIF | 10 | up | down | | | | | | Peptidylprolyl isomerase F (cyclophilin F) |
| Hs.124553 | NM_005741 | ZNF263 | 16 | | down | | | | | | Zinc finger protein 263 |
| Hs.123464 | NM_005767 | P2RY5 | 13 | | down | | down | | | | Purinergic receptor P2Y, G-protein coupled, 5 |
| Hs.424126 | NM_005770 | SERF2 | 15;17;7;6 | up | | | | | | | Small EDRK-rich factor 2 |
| Hs.294603 | NM_005776 | CNIH | 14 | up | | | | | | | Cornichon homolog (Drosophila) |
| Hs.188879 | NM_005777 | RBM6 | 3;19 | | | | | | down | | RNA binding motif protein 6 |
| Hs.436922 | NM_005798 | RFP2 | 13 | down | down | | | down | | | Ret finger protein 2 |
| Hs.440168 | NM_005822 | DSCR1L1 | 6 | | | | up | | down | | Down syndrome critical region gene 1-like 1 |
| Hs.436944 | NM_005841 | SPRY1 | 4 | down | down | | | | | | Sprouty homolog 1, antagonist of FGF signaling (Drosophila) |
| Hs.18676 | NM_005842 | SPRY2 | 13;3 | down | | | | | | | Sprouty homolog 2 (Drosophila) |
| Hs.432862 | NM_005885 | MARCH-VI | 5 | | | up | | | | | Membrane-associated RING-CH protein VI |
| Hs.186486 | NM_005923 | MAP3K5 | 6 | | | | | down | | | Mitogen-activated protein kinase kinase kinase 5 |
| Hs.433391 | NM_005950 | MT1G | 16;12 | | | | down | down | | | Metallothionein 1G |
| Hs.435974 | NM_005956 | MTHFD1 | 14;2 | | down | | | | | | Methylenetetrahydrofolate dehydrogenase (NADP+ dependent), methenyltetrahydrofolate cyclohydrolase, formyltetrahydrofolate synthetase |
| Hs.107474 | NM_005966 | NAB1 | 2;4;3 | | | up | | | | | NGFI-A binding protein 1 (EGR1 binding protein 1) |
| Hs.2430 | NM_005997 | TCFL1 | 1 | | | | up | | | | Transcription factor-like 1 |
| Hs.170107 | NM_006003 | UQCRFS1 | 19 | | | | | up | | | Ubiquinol-cytochrome c reductase, Rieske iron-sulfur polypeptide 1 |
| Hs.406096 | NM_006007 | ZA20D2 | 9;19;6;17 | up | | | | | | | Zinc finger, A20 domain containing 2 |
| Hs.436446 | NM_006010 | ARMET | 3 | up | | | | up | | | Arginine-rich, mutated in early stage tumors |
| Hs.412842 | NM_006023 | C10orf7 | 10 | | down | | | | | | Chromosome 10 open reading frame 7 |
| Hs.203620 | NM_006040 | HS3ST4 | 16 | | | | | up | up | | Heparan sulfate (glucosamine) 3-O-sulfotransferase 4 |
| Hs.115830 | NM_006043 | HS3ST2 | 16 | | | | | up | | | Heparan sulfate (glucosamine) 3-O-sulfotransferase 2 |
| Hs.503692 | NM_006106 | YAP1 | 11 | | down | | | | | | Yes-associated protein 1, 65kDa |
| Hs.367854 | NM_006109 | SKB1 | 14 | up | | | | | | | SKB1 homolog (S. pombe) |
| Hs.15250 | NM_006117 | PECI | 6 | | down | | | | | | Peroxisomal D3,D2-enoyl-CoA isomerase |
| Hs.369068 | NM_006141 | DNCL2 | 16;2 | | | up | | | | | Dynein, cytoplasmic, light intermediate polypeptide 2 |
| Hs.1565 | NM_006154 | NEDD4 | 15 | down | up | | | | | | Neural precursor cell expressed, developmentally down- |

| UniGene ID | Annotation Acc | Symbol | Chr. | AnCg | CB | DLPFC | Nacc | PC | STG | Name |
|---|---|---|---|---|---|---|---|---|---|---|
| Hs.339831 | NM_006211 | PENK | 8 | | | | | | | Proenkephalin regulated 4 |
| Hs.38449 | NM_006216 | SERPINE2 | 2 | | | | up | | down | Serine (or cysteine) proteinase inhibitor, clade E (nexin, plasminogen activator inhibitor type 1), member 2 |
| Hs.334868 | NM_006246 | PPP2R5E | 14 | | | | up | | | Protein phosphatase 2, regulatory subunit B (B56), epsilon isoform |
| Hs.43322 | NM_006251 | PRKAA1 | 5 | | down | | | | down | Protein kinase, AMP-activated, alpha 1 catalytic subunit |
| Hs.375001 | NM_006289 | TLN1 | 9 | | | | down | | | Talin 1 |
| Hs.25313 | NM_006337 | MCRS1 | 12 | | | down | | | | Microspherule protein 1 |
| Hs.465784 | NM_006351 | TIMM44 | 19 | | up | | | | | Translocase of inner mitochondrial membrane 44 homolog (yeast) |
| Hs.132902 | NM_006366 | CAP2 | 6 | up | | | up | | | CAP, adenylate cyclase-associated protein, 2 (yeast) |
| Hs.376064 | NM_006392 | NOL5A | 20;6 | | down | | | | | Nucleolar protein 5A (56kDa with KKE/D repeat) |
| Hs.11417 | NM_006423 | RABAC1 | 19 | | | up | | | | Rab acceptor 1 (prenylated) |
| Hs.435342 | NM_006425 | SLU7 | 5 | | up | | | | | Step II splicing factor SLU7 |
| Hs.421509 | NM_006430 | CCT4 | 2 | up | | | | up | | Chaperonin containing TCP1, subunit 4 (delta) |
| Hs.433222 | NM_006432 | NPC2 | 14;11;3 | | | | down | | | Niemann-Pick disease, type C2 |
| Hs.109752 | NM_006443 | C6orf108 | 6;20 | up | | | | | | Chromosome 6 open reading frame 108 |
| Hs.14894 | NM_006464 | TGOLN2 | 2 | | | up | | | | Trans-golgi network protein 2 |
| Hs.439153 | NM_006502 | POLH | 6 | | up | | | | | Polymerase (DNA directed), eta |
| Hs.530045 | NM_006524 | ZNF138 | 7 | down | | | | | | Zinc finger protein 138 (clone pHZ-32) |
| Hs.444558 | NM_006558 | KHDRBS3 | 8 | | | | up | | | KH domain containing, RNA binding, signal transduction associated 3 |
| Hs.309288 | NM_006561 | CUGBP2 | 10 | | | | up | | | CUG triplet repeat, RNA binding protein 2 |
| Hs.368367 | NM_006565 | CTCF | 16 | | down | | | | | CCCTC-binding factor (zinc finger protein) |
| Hs.159525 | NM_006569 | CGREF1 | 2 | | | | up | | | Cell growth regulator with EF hand domain 1 |
| Hs.45127 | NM_006574 | CSPG5 | 3 | | | | | down | | Chondroitin sulfate proteoglycan 5 (neuroglycan C) |
| Hs.155090 | NM_006578 | GNB5 | 15 | | | | up | | | Guanine nucleotide binding protein (G protein), beta 5 |
| Hs.30696 | NM_006602 | TCFL5 | 20 | | | | down | | | Transcription factor-like 5 (basic helix-loop-helix) |
| Hs.412870 | NM_006627 | POP4 | 19;9 | | | | up | | | Processing of precursor 4, ribonuclease P/MRP subunit (S. cerevisiae) |
| Hs.415846 | NM_006657 | FTCD | 21 | down | | | | | | Formiminotransferase cyclodeaminase |
| Hs.227011 | NM_006658 | C7orf16 | 7 | up | | | | up | | Chromosome 7 open reading frame 16 |
| Hs.199743 | NM_006680 | ME3 | 11 | | | | up | | | Malic enzyme 3, NADP(+)-dependent, mitochondrial |

| UniGene ID | Annotation | | Chr. | Direction of Change in SZ relative to Controls | | | | | | Name |
|---|---|---|---|---|---|---|---|---|---|---|
| | Acc | Symbol | | AnCg | CB | DLPFC | Nacc | PC | STG | |
| Hs.2207 | NM_006685 | PROL3 | 4 | down | | | | | | Proline rich 5 (salivary) |
| Hs.6396 | NM_006694 | JTB | 1 | up | | | | | | Jumping translocation breakpoint |
| Hs.225949 | NM_006707 | BTNL3 | 5 | down | down | | | | | Butyrophilin-like 3 |
| Hs.146804 | NM_006717 | SPIN | 9 | | | | up | | | Spindlin |
| Hs.505662 | NM_006741 | PPP1R1A | 12 | | | up | | | | Protein phosphatase 1, regulatory (inhibitor) subunit 1A |
| Hs.301404 | NM_006743 | RBM3 | X | | down | | | | | RNA binding motif (RNP1, RRM) protein 3 |
| Hs.109655 | NM_006746 | SCML1 | X | | | | | | down | Sex comb on midleg-like 1 (Drosophila) |
| Hs.192686 | NM_006749 | SLC20A2 | 8 | | down | | down | | | Solute carrier family 20 (phosphate transporter), member 2 |
| Hs.337295 | NM_006819 | STIP1 | 11 | | | | | | up | Stress-induced-phosphoprotein 1 (Hsp70/Hsp90-organizing protein) |
| Hs.260903 | NM_006874 | ELF2 | 4 | up | | | | | | E74-like factor 2 (ets domain transcription factor) |
| Hs.436405 | NM_006899 | IDH3B | 20;6;1 | | down | | | | | Isocitrate dehydrogenase 3 (NAD+) beta |
| Hs.466848 | NM_006905 | PSG1 | 19 | | up | | | | | Pregnancy specific beta-1-glycoprotein 1 |
| Hs.435274 | NM_006922 | SCN3A | 2 | | | | | down | | Sodium channel, voltage-gated, type III, alpha |
| Hs.376984 | NM_006941 | SOX10 | 22 | | | | down | | | SRY (sex determining region Y)-box 10 |
| Hs.237825 | NM_006947 | SRP72 | 4,16 | | | up | | | | Signal recognition particle 72kDa |
| Hs.534115 | NM_006988 | ADAMTS1 | 21 | | down | | | | down | A disintegrin-like and metalloprotease (reprolysin type) with thrombospondin type 1 motif, 1 |
| Hs.30246 | NM_006996 | SLC19A2 | 1 | down | | | | | | Solute carrier family 19 (thiamine transporter), member 2 |
| Hs.29353 | NM_007030 | TPPP | 5;20 | | down | | | | | Brain-specific protein p25 alpha |
| Hs.125750 | NM_007035 | KERA | 12 | | up | | | | | Keratocan |
| Hs.43670 | NM_007054 | KIF3A | 5 | | | | up | | | Kinesin family member 3A |
| Hs.436896 | NM_007055 | POLR3A | 10 | | | up | | | | Polymerase (RNA) III (DNA directed) polypeptide A, 155kDa |
| Hs.474797 | NM_007061 | CDC42EP1 | 22 | | | up | | | | CDC42 effector protein (Rho GTPase binding) 1 |
| Hs.160958 | NM_007065 | CDC37 | 19 | | | | up | | | CDC37 cell division cycle 37 homolog (S. cerevisiae) |
| Hs.142245 | NM_007071 | HHLA3 | 1 | up | | | | | | HERV-H LTR-associating 3 |
| Hs.269512 | NM_007085 | FSTL1 | 3 | | down | | | | | Follistatin-like 1 |
| Hs.106857 | NM_007088 | CALB2 | 16;19;15 | | | | up | | | Calbindin 2, 29kDa (calretinin) |
| Hs.484241 | NM_007097 | CLTB | 5 | | | | | | | Clathrin, light polypeptide (Lcb) |
| Hs.119014 | NM_007147 | ZNF175 | 19 | | down | | | down | | Zinc finger protein 175 |
| Hs.158174 | NM_007149 | ZNF184 | 6 | | down | | | | | Zinc finger protein 184 (Kruppel-like) |
| Hs.434283 | NM_007167 | ZNF258 | 1 | | up | | | | | Zinc finger protein 258 |

| UniGene ID | Annotation | | Chr. | Direction of Change in SZ relative to Controls | | | | | | Name |
| | Acc | Symbol | | AnCg | CB | DLPFC | Nacc | PC | STG | |
|---|---|---|---|---|---|---|---|---|---|---|
| Hs.205163 | NM_007208 | MRPL3 | 3 | | down | | | | | Mitochondrial ribosomal protein L3 |
| Hs.388668 | NM_007246 | KLHL2 | 4 | | | | up | | | Kelch-like 2, Mayven (Drosophila) |
| Hs.377070 | NM_007325 | GRIA3 | X | | | | up | | | Glutamate receptor, ionotropic, AMPA 3 |
| Hs.189826 | NM_007345 | ZNF236 | 18 | | | | | | up | Zinc finger protein 236 |
| Hs.240770 | NM_007362 | NCBP2 | 3;1 | | down | | | | | Nuclear cap binding protein subunit 2, 20kDa |
| Hs.500104 | NM_012095 | AP3M1 | 10 | up | | | | | | Adaptor-related protein complex 3, mu 1 subunit |
| Hs.204041 | NM_012111 | AHSA1 | 14;9 | up | up | | | up | | AHA1, activator of heat shock 90kDa protein ATPase homolog 1 (yeast) |
| Hs.212395 | NM_012127 | CIZ1 | 9 | up | | | | | | CDKN1A interacting zinc finger protein 1 |
| Hs.24178 | NM_012155 | EML2 | 19 | | up | | | | | Echinoderm microtubule associated protein like 2 |
| Hs.438454 | NM_012173 | FBXO25 | 8 | | | up | | up | | F-box protein 25 |
| Hs.22867 | NM_012199 | EIF2C1 | 1 | down | | | | | | Eukaryotic translation initiation factor 2C, 1 |
| Hs.179915 | NM_012202 | GNG3 | 11 | | | | up | | | Guanine nucleotide binding protein (G protein), gamma 3 |
| Hs.155742 | NM_012203 | GRHPR | 9;17 | | down | | | | | Glyoxylate reductase/hydroxypyruvate reductase |
| Hs.494804 | NM_012212 | LTB4DH | 9 | | | up | | | | Leukotriene B4 12-hydroxydehydrogenase |
| Hs.481181 | NM_012224 | NEK1 | 4 | down | | | | | | NIMA (never in mitosis gene a)-related kinase 1 |
| Hs.369779 | NM_012238 | SIRT1 | 10 | | | | | down | | Sirtuin (silent mating type information regulation 2 homolog) 1 (S. cerevisiae) |
| Hs.309583 | NM_012254 | SLC27A5 | 19 | up | up | | | | | Solute carrier family 27 (fatty acid transporter), member 5 |
| Hs.144287 | NM_012259 | HEY2 | 6 | down | | | | | | Hairy/enhancer-of-split related with YRPW motif 2 |
| Hs.22920 | NM_012261 | C20orf103 | 20 | | | | | | down | Chromosome 20 open reading frame 103 |
| Hs.21703 | NM_012281 | KCND2 | 7 | | | | up | | | Potassium voltage-gated channel, Shal-related subfamily, member 2 |
| Hs.433057 | NM_012304 | FBXL7 | 5;6 | | up | | | | | F-box and leucine-rich repeat protein 7 |
| Hs.397918 | NM_012311 | KIN | 10 | | | | | | down | KIN, antigenic determinant of recA protein homolog (mouse) |
| Hs.370040 | NM_012333 | MYCBP | 1 | down | up | | | | | C-myc binding protein |
| Hs.470417 | NM_012392 | PEF | 1 | up | | | | | | PEF protein with a long N-terminal hydrophobic domain (peflin) |
| Hs.430742 | NM_012395 | PFTK1 | 7 | | | | | | | PFTAIRE protein kinase 1 |
| Hs.167496 | NM_012416 | RANBP6 | 9 | | | | up | | | RAN binding protein 6 |
| Hs.166313 | NM_012419 | RGS17 | 6 | | | up | | | | Regulator of G-protein signaling 17 |
| Hs.471011 | NM_012433 | SF3B1 | 2 | | | up | | | | Splicing factor 3b, subunit 1, 155kDa |
| Hs.102735 | NM_012446 | SSBP2 | 5 | down | | | | | | Single-stranded DNA binding protein 2 |
| Hs.235750 | NM_012456 | TIMM10 | 11;17 | | down | | | | | Translocase of inner mitochondrial membrane 10 homolog |

| | Annotation | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.59757 | NM_012482 | ZNF281 | 1 | | | | | down | | Zinc finger protein 281 |
| Hs.115721 | NM_013247 | PRSS25 | 2 | up | | | | | | Protease, serine, 25 |
| Hs.292156 | NM_013253 | DKK3 | 11 | | up | | | | | Dickkopf homolog 3 (Xenopus laevis) |
| Hs.476291 | NM_013286 | RBM15B | 3 | down | | | | | | RNA binding motif protein 15B |
| Hs.517436 | NM_013313 | YPEL1 | 22 | up | | up | | | | Yippee-like 1 (Drosophila) |
| Hs.433151 | NM_013343 | LOH3CR2A | 3;1 | | up | | | | | Loss of heterozygosity, 3, chromosomal region 2, gene A |
| Hs.40098 | NM_013372 | GREM1 | 15 | | up | | | | | Gremlin 1 homolog, cysteine knot superfamily (Xenopus laevis) |
| Hs.279877 | NM_013393 | FTSJ2 | 7 | | down | | | | | FtsJ homolog 2 (E. coli) |
| Hs.7765 | NM_013399 | C16orf5 | 16 | | up | | | | | Chromosome 16 open reading frame 5 |
| Hs.416049 | NM_013433 | TNPO2 | 19 | | | down | | | | Transportin 2 (importin 3, karyopherin beta 2b) |
| Hs.408515 | NM_013985 | NRG2 | 5 | down | | | | up | | Neuregulin 2 |
| Hs.15400 | NM_014015 | DEXI | 16 | | | | up | up | | Dexamethasone-induced transcript |
| Hs.13370 | NM_014044 | UNC50 | 2 | | down | | | | | Unc-50 homolog (C. elegans) |
| Hs.436500 | NM_014063 | DBNL | 7 | | | | | | up | Drebrin-like |
| Hs.368971 | NM_014071 | NCOA6 | 20 | up | | | | | | Nuclear receptor coactivator 6 |
| Hs.333823 | NM_014078 | MRPL13 | 8;18 | | down | up | up | | | Mitochondrial ribosomal protein L13 |
| Hs.272215 | NM_014079 | KLF15 | 3 | | down | down | | | | Kruppel-like factor 15 |
| Hs.11614 | NM_014157 | HSPC065 | | | down | | | | | HSPC065 protein |
| Hs.127496 | NM_014170 | HSPC135 | 3 | | | | up | | | HSPC135 protein |
| Hs.18349 | NM_014175 | MRPL15 | 8;12 | | down | | | | | Mitochondrial ribosomal protein L15 |
| Hs.445890 | NM_014184 | HSPC163 | 1 | | | up | | | | HSPC163 protein |
| Hs.233458 | NM_014223 | NFYC | 1 | up | | | | | | Nuclear transcription factor Y, gamma |
| Hs.467192 | NM_014225 | PPP2R1A | 19 | | | | up | | | Protein phosphatase 2 (formerly 2A), regulatory subunit A (PR 65), alpha isoform |
| Hs.114062 | NM_014241 | PTPLA | 10 | | up | | | | | Protein tyrosine phosphatase-like (proline instead of catalytic arginine), member a |
| Hs.437277 | NM_014275 | MGAT4B | 5;19;10 | up | | down | | | | Mannosyl (alpha-1,3-)-glycoprotein beta-1,4-N-acetylglucosaminyltransferase, isoenzyme B |
| Hs.301760 | NM_014286 | FREQ | 9 | down | | | | | | Frequenin homolog (Drosophila) |
| Hs.193842 | NM_014290 | TDRD7 | 9 | | down | | | | | Tudor domain containing 7 |
| Hs.282998 | NM_014309 | RBM9 | 22 | | | | up | | | RNA binding motif protein 9 |
| Hs.523054 | NM_014313 | SMP1 | 11 | up | | | | | | NPD014 protein |
| Hs.330384 | NM_014325 | CORO1C | 12 | up | | | | | | Coronin, actin binding protein, 1C |

| Annotation | | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.370510 | NM_014333 | IGSF4 | 11 | down | up | | | | | Immunoglobulin superfamily, member 4 |
| Hs.189810 | NM_014351 | SULT4A1 | 22 | | | | up | | | Sulfotransferase family 4A, member 1 |
| Hs.310431 | NM_014386 | PKD2L2 | 5 | down | | | | | | Polycystic kidney disease 2-like 2 |
| Hs.316890 | NM_014426 | SNX5 | 20 | | | | down | | | Sorting nexin 5 |
| Hs.443577 | NM_014452 | TNFRSF21 | 6 | | | | | up | | Tumor necrosis factor receptor superfamily, member 21 |
| Hs.232543 | NM_014456 | PDCD4 | 10 | | down | | | | | Programmed cell death 4 (neoplastic transformation inhibitor) |
| Hs.111632 | NM_014463 | LSM3 | 3 | | | up | | | | LSM3 homolog, U6 small nuclear RNA associated (S. cerevisiae) |
| Hs.438994 | NM_014480 | ZNF544 | 19 | | | | up | | | Zinc finger protein 544 |
| Hs.221436 | NM_014483 | RBMS3 | 3 | down | | | | | | RNA binding motif, single stranded interacting protein |
| Hs.143600 | NM_014498 | GOLPH4 | 3 | down | | | | | | Golgi phosphoprotein 4 |
| Hs.252682 | NM_014506 | TOR1B | 9 | up | | | | | | Torsin family 1, member B (torsin B) |
| Hs.13014 | NM_014570 | ARFGAP3 | 22 | | | up | down | | | ADP-ribosylation factor GTPase activating protein 3 |
| Hs.525339 | NM_014584 | ERO1L | 14 | | | | | | | ERO1-like (S. cerevisiae) |
| Hs.180933 | NM_014593 | CXXC1 | 18 | | | | | up | | CXXC finger 1 (PHD domain) |
| Hs.368808 | NM_014600 | EHD3 | 2;6 | | | | up | | | EH-domain containing 3 |
| Hs.26704 | NM_014608 | CYFIP1 | 15;9 | | | down | | | | Cytoplasmic FMR1 interacting protein 1 |
| Hs.413801 | NM_014614 | PSME4 | 2 | | up | | | | | Proteasome (prosome, macropain) activator subunit 4 |
| Hs.330073 | NM_014686 | KIAA0355 | 19 | up | | | | | | KIAA0355 |
| Hs.196054 | NM_014707 | HDAC9 | 7 | | | | | down | | Histone deacetylase 9 |
| Hs.410092 | NM_014741 | KIAA0652 | 11 | | | | down | | | KIAA0652 gene product |
| Hs.484349 | NM_014757 | MAML1 | 5 | | | down | | | | Mastermind-like 1 (Drosophila) |
| Hs.44024 | NM_014763 | MRPL19 | 2 | | | up | | | | Mitochondrial ribosomal protein L19 |
| Hs.370530 | NM_014788 | TRIM14 | 9 | down | | | | | | Tripartite motif-containing 14 |
| Hs.533245 | NM_014829 | DDX46 | 5 | | | | | down | | DEAD (Asp-Glu-Ala-Asp) box polypeptide 46 |
| Hs.3094 | NM_014876 | KIAA0063 | 22 | up | | | | | | KIAA0063 gene product |
| Hs.130014 | NM_014880 | DCL-1 | 2 | | | | down | | | Type 1 transmembrane C-type lectin receptor DCL-1 |
| Hs.227602 | NM_014892 | RBM16 | 6 | | down | | | | | RNA binding motif protein 16 |
| Hs.131683 | NM_014912 | CPEB3 | 10 | | | up | | | | Cytoplasmic polyadenylation element binding protein 3 |
| Hs.22109 | NM_014952 | BAHD1 | 15 | up | | | | | | Bromo adjacent homology domain containing 1 |
| Hs.124490 | NM_014977 | ACIN1 | 14 | | | | | down | | Apoptotic chromatin condensation inducer 1 |
| Hs.270499 | NM_015001 | SHARP | 1 | | | up | | | | SMART/HDAC1 associated repressor protein |
| Hs.159699 | NM_015002 | FBXO21 | 12 | | | up | | | | F-box protein 21 |
| Hs.189409 | NM_015033 | FNBP1 | 9 | | | | | | down | Formin binding protein 1 |

| UniGene ID | Annotation Acc | Symbol | Chr. | AnCg | CB | DLPFC | Nacc | PC | STG | Name |
|---|---|---|---|---|---|---|---|---|---|---|
| Hs.293593 | NM_015071 | ARHGAP26 | 5 | | up | | | | | Rho GTPase activating protein 26 |
| Hs.440414 | NM_015087 | SPG20 | 13 | | down | | | | | Spastic paraplegia 20, spartin (Troyer syndrome) |
| Hs.269775 | NM_015093 | MAP3K7IP2 | 6 | up | | | | | | Mitogen-activated protein kinase kinase kinase 7 interacting protein 2 |
| Hs.331431 | NM_015200 | SCC-112 | 4 | down | | | | | | SCC-112 protein |
| Hs.410497 | NM_015379 | BRI3 | 7 | up | | | | | | Brain protein I3 |
| Hs.105547 | NM_015392 | NPDC1 | 9 | up | | | | | | Neural proliferation, differentiation and control, 1 |
| Hs.25956 | NM_015464 | SOSTDC1 | 7 | | | | | | up | Sclerostin domain containing 1 |
| Hs.472630 | NM_015474 | SAMHD1 | 20 | | | down | | | | SAM domain and HD domain 1 |
| Hs.146100 | NM_015553 | PIP3-E | 6 | | | | up | | | Phosphoinositide-binding protein PIP3-E |
| Hs.127401 | NM_015662 | SLB | 6 | | | up | | | | Selective LIM binding factor, rat homolog |
| Hs.369144 | NM_015665 | AAAS | 12 | | up | | | | | Achalasia, adrenocortical insufficiency, alacrimia (Allgrove, triple-A) |
| Hs.391481 | NM_015693 | PDZK6 | 4 | up | | | | | | PDZ domain containing 6 |
| Hs.474914 | NM_015705 | RUTBC3 | 22 | down | | | | | | RUN and TBC1 domain containing 3 |
| Hs.512592 | NM_015713 | RRM2B | 8 | | up | | | | | Ribonucleotide reductase M2 B (TP53 inducible) |
| Hs.235368 | NM_015719 | COL5A3 | 19 | down | down | | down | | down | Collagen, type V, alpha 3 |
| Hs.250693 | NM_015852 | ZNF117 | 7;19 | down | | | | | | Krueppel-related zinc finger protein |
| Hs.128959 | NM_015885 | PCF11 | 11 | | | | down | | | Pre-mRNA cleavage complex II protein Pcf11 |
| Hs.348326 | NM_015894 | STMN3 | 20 | down | | | | | | Stathmin-like 3 |
| Hs.414952 | NM_015910 | LOC51057 | 2 | | up | | | | | Hypothetical protein LOC51057 |
| Hs.16606 | NM_015960 | CUTC | 10 | | down | | | | | CutC copper transporter homolog (E.coli) |
| Hs.435759 | NM_015963 | THAP4 | 2 | up | | | | | | THAP domain containing 4 |
| Hs.44298 | NM_015969 | MRPS17 | 7 | up | | | down | | | Mitochondrial ribosomal protein S17 |
| Hs.370703 | NM_015974 | CRYL1 | 13 | | | | | | | Crystallin, lambda 1 |
| Hs.370168 | NM_015986 | CRLF3 | 17 | | | | | down | | Cytokine receptor-like factor 3 |
| Hs.525752 | NM_015995 | KLF13 | 15 | up | | | | | | Krueppel-like factor 13 |
| Hs.271876 | NM_016010 | CGI-62 | 8 | down | | | | | | CGI-62 protein |
| Hs.183646 | NM_016011 | CGI-63 | 1 | | | down | | | | Nuclear receptor binding factor 1 |
| Hs.106529 | NM_016013 | NDUFAF1 | 15 | up | | | | | | NADH dehydrogenase (ubiquinone) 1 alpha subcomplex, assembly factor 1 |
| Hs.514216 | NM_016016 | CGI-69 | 17 | up | down | | | | | CGI-69 protein |
| Hs.145386 | NM_016033 | CGI-90 | 8 | down | | | down | | | CGI-90 protein |
| Hs.3945 | NM_016045 | C20orf45 | 20 | | | | down | | | Chromosome 20 open reading frame 45 |
| Hs.483296 | NM_016048 | CGI-111 | 5 | | | | | | up | CGI-111 protein |

| | Annotation | | | Direction of Change in SZ relative to Controls | | | | | | Name |
|---|---|---|---|---|---|---|---|---|---|---|
| UniGene ID | Acc | Symbol | Chr. | AnCg | CB | DLPFC | Nacc | PC | STG | |
| Hs.271614 | NM_016049 | C14orf122 | 14 | up | | | | | | Chromosome 14 open reading frame 122 |
| Hs.157401 | NM_016058 | CGI-121 | 2 | | up | | up | | | CGI-121 protein |
| Hs.436161 | NM_016067 | MRPS18C | 4 | | up | | | | | Mitochondrial ribosomal protein S18C |
| Hs.435952 | NM_016082 | CDK5RAP1 | 20 | | | down | | | | CDK5 regulatory subunit associated protein 1 |
| Hs.25829 | NM_016084 | RASD1 | 17 | | | | | up | | RAS, dexamethasone-induced 1 |
| Hs.108969 | NM_016145 | PTD008 | 19 | up | | | | | | PTD008 protein |
| Hs.159581 | NM_016155 | MMP17 | 12 | up | | | | | | Matrix metalloproteinase 17 (membrane-inserted) |
| Hs.446179 | NM_016200 | LSM8 | 7 | | up | | | | | LSM8 homolog, U6 small nuclear RNA associated (S. cerevisiae) |
| Hs.131133 | NM_016203 | PRKAG2 | 7 | | up | | | | up | Protein kinase, AMP-activated, gamma 2 non-catalytic subunit |
| Hs.135756 | NM_016218 | POLK | 5 | | | up | | | | Polymerase (DNA directed) kappa |
| Hs.328865 | NM_016221 | DCTN4 | 5 | | down | | | | | Dynactin 4 (p62) |
| Hs.191213 | NM_016224 | SNX9 | 6 | | | up | | | | Sorting nexin 9 |
| Hs.208759 | NM_016231 | NLK | 17 | | up | | | | | Nemo like kinase |
| Hs.148685 | NM_016235 | GPRC5B | 16 | | | | down | | | G protein-coupled receptor, family C, group 5, member B |
| Hs.334832 | NM_016243 | NQO3A2 | 1 | | | | down | | | NAD(P)H:quinone oxidoreductase type 3, polypeptide A2 |
| Hs.18788 | NM_016246 | DHRS10 | 19 | | | | down | down | | Dehydrogenase/reductase (SDR family) member 10 |
| Hs.125132 | NM_016269 | LEF1 | 4 | | up | down | | | | Lymphoid enhancer-binding factor 1 |
| Hs.278627 | NM_016297 | PCYOX1 | 2 | | | up | | | | Prenylcysteine oxidase 1 |
| Hs.470887 | NM_016315 | GULP1 | 2 | | | | | down | | GULP, engulfment adaptor PTB domain containing 1 |
| Hs.158530 | NM_016339 | RAPGEFL1 | 17 | up | | | | | | Rap guanine nucleotide exchange factor (GEF)-like 1 |
| Hs.483329 | NM_016340 | RAPGEF6 | 5 | | up | | | | | KIAA1961 protein |
| Hs.224137 | NM_016390 | C9orf14 | 9 | | down | | | | | Chromosome 9 open reading frame 114 |
| Hs.497967 | NM_016396 | HSPC129 | 15 | | | up | | | | Hypothetical protein HSPC129 |
| Hs.283322 | NM_016401 | HSPC138 | 11 | | | up | | | up | Hypothetical protein HSPC138 |
| Hs.436502 | NM_016486 | LOC51249 | 1 | down | | | | | | Hypothetical protein LOC51249 |
| Hs.408233 | NM_016492 | RANGNRF | 17 | | | | up | | | RAN guanine nucleotide release factor |
| Hs.524094 | NM_016505 | PS1D | 1 | up | | | | | | Putative S1 RNA binding domain protein |
| Hs.29549 | NM_016511 | CLEC1 | 12,X | down | | | | | | C-type lectin-like receptor-1 |
| Hs.478393 | NM_016559 | PEX5L | 3 | | | down | | up | | Peroxisomal biogenesis factor 5-like |
| Hs.475387 | NM_016565 | E2IG2 | 11 | | | | | | | E2IG2 protein |
| Hs.200063 | NM_016596 | HDAC7A | 12 | | | | | | down | Histone deacetylase 7A |
| Hs.433439 | NM_016622 | MRPL35 | | | | up | | | | Mitochondrial ribosomal protein L35 |
| Hs.478064 | NM_016625 | MGC12197 | 3 | | | | | up | | BM-011 protein |

| Annotation | | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.465144 | NM_016626 | RKHD2 | 18 | | | up | | | | Ring finger and KH domain containing 2 |
| Hs.278635 | NM_016648 | HDCMA18P | 4 | | down | | | | | HDCMA18P protein |
| Hs.369284 | NM_016649 | C20orf6 | 20 | | down | | | | | Chromosome 20 open reading frame 6 |
| Hs.171342 | NM_016652 | CRNKL1 | 20 | | | up | | up | | Crn, crooked neck-like 1 (Drosophila) |
| Hs.127792 | NM_016941 | DLL3 | 19 | | | | | | up | Delta-like 3 (Drosophila) |
| Hs.40735 | NM_017412 | FZD3 | 8 | | | | | down | | Frizzled homolog 3 (Drosophila) |
| Hs.286233 | NM_017425 | SPA17 | 11;19 | | | | | | up | Sperm autoantigenic protein 17 |
| Hs.108112 | NM_017443 | POLE3 | 9 | | down | | | | | Polymerase (DNA directed), epsilon 3 (p17 subunit) |
| Hs.437084 | NM_017544 | NKRF | X | | | | up | | | NF-kappa B repressing factor |
| Hs.458304 | NM_017578 | ROPN1 | 3 | down | | | | | | Ropporin, rhophilin associated protein 1 |
| Hs.165636 | NM_017594 | DIRAS2 | 9 | | | up | up | | | DIRAS family, GTP-binding RAS-like 2 |
| Hs.258798 | NM_017615 | C10orf86 | 10 | up | down | | down | | | Chromosome 10 open reading frame 86 |
| Hs.29700 | NM_017665 | ZCCHC10 | 5 | down | | | | | | Zinc finger, CCHC domain containing 10 |
| Hs.369932 | NM_017714 | C20orf13 | 20 | | | | | | up | Chromosome 20 open reading frame 13 |
| Hs.483993 | NM_017734 | PALMD | 1 | | | | | | down | Palmdelphin |
| Hs.440401 | NM_017750 | FLJ20296 | 2 | | down | | | | down | All-trans-13,14-dihydroretinol saturase |
| Hs.147836 | NM_017768 | FLJ20331 | 1 | | | | | down | | Hypothetical protein FLJ20331 |
| Hs.444269 | NM_017776 | FLJ20344 | X | | up | up | | | | Hypothetical protein FLJ20344 |
| Hs.150122 | NM_017784 | OSBPL10 | 3 | | | up | | | | Oxysterol binding protein-like 10 |
| Hs.368710 | NM_017785 | FLJ20364 | 5 | | down | | | | | Hypothetical protein FLJ20364 |
| Hs.408652 | NM_017794 | KIAA1797 | 9 | | | | up | up | | KIAA1797 |
| Hs.371210 | NM_017847 | C1orf27 | 1 | | up | | | | down | Chromosome 1 open reading frame 27 |
| Hs.134406 | NM_017853 | TXNL4B | 16 | up | | | | | up | Thioredoxin-like 4B |
| Hs.105606 | NM_017854 | FLJ20512 | 19 | up | | | up | down | | Hypothetical protein FLJ20512 |
| Hs.377705 | NM_017865 | FLJ20531 | 1 | | | | | | | Hypothetical protein FLJ20531 |
| Hs.525238 | NM_017924 | C14orf119 | 14 | | | up | | up | | Chromosome 14 open reading frame 119 |
| Hs.249591 | NM_017925 | C9orf55 | 9 | down | | | | | | Chromosome 9 open reading frame 55 |
| Hs.30783 | NM_017967 | FLJ20850 | 19 | up | | down | | | | Hypothetical protein FLJ20850 |
| Hs.297044 | NM_017987 | RUFY2 | 10 | | | | up | | | RUN and FYVE domain containing 2 |
| Hs.516341 | NM_017991 | FLJ10081 | 2 | | | | | | down | Hypothetical protein FLJ10081 |
| Hs.128258 | NM_017993 | FLJ10094 | 13 | | | up | up | | | Hypothetical protein FLJ10094 |
| Hs.532296 | NM_017998 | C9orf40 | 9 | | | | | up | | Chromosome 9 open reading frame 40 |
| Hs.241523 | NM_018008 | ZNF312 | 3 | | | | | up | up | Zinc finger protein 312 |
| Hs.445244 | NM_018013 | FLJ10159 | 6 | | | | up | | | Hypothetical protein FLJ10159 |
| Hs.353454 | NM_018045 | FLJ10276 | 1 | up | | | | | | Hypothetical protein FLJ10276 |

| Annotation | | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.213393 | NM_018046 | VG5Q | 5 | | | up | | | | Angiogenic factor VG5Q |
| Hs.262823 | NM_018060 | FLJ10326 | 1 | | down | | | | | Mitochondrial isoleucine tRNA synthetase |
| Hs.356096 | NM_018067 | FLJ10350 | 1 | up | | | | | | Hypothetical protein FLJ10350 |
| Hs.270107 | NM_018115 | SDAD1 | 4 | | | up | | | | SDA1 domain containing 1 |
| Hs.447458 | NM_018121 | C10orf6 | 10 | up | | | | | | Hypothetical protein LOC143286 |
| Hs.31082 | NM_018126 | TMEM33 | 4 | | | | | up | | Transmembrane protein 33 |
| Hs.26156 | NM_018216 | PANK4 | 1;2 | up | | | | | | Pantothenate kinase 4 |
| Hs.174021 | NM_018225 | SMU1 | 9 | | | | | up | | Smu-1 suppressor of mec-8 and unc-52 homolog (C. elegans) |
| Hs.260238 | NM_018238 | FLJ10842 | 7;12;2 | | | down | | | | Hypothetical protein FLJ10842 |
| Hs.502773 | NM_018269 | MTCBP-1 | 2 | up | | | | | | Membrane-type 1 matrix metalloproteinase cytoplasmic tail binding protein-1 |
| Hs.368960 | NM_018297 | NGLY1 | 3 | | | | up | | | N-glycanase 1 |
| Hs.503022 | NM_018312 | C11orf23 | 11 | | | | | down | | Chromosome 11 open reading frame 23 |
| Hs.58382 | NM_018322 | C6orf64 | 6 | | down | | | | | Chromosome 6 open reading frame 64 |
| Hs.458312 | NM_018328 | MBD5 | 2 | down | | | | | | Methyl-CpG binding domain protein 5 |
| Hs.37558 | NM_018339 | RFK | 9 | | | | up | | | Riboflavin kinase |
| Hs.176227 | NM_018342 | FLJ11155 | 4 | | down | | down | | | Hypothetical protein FLJ11155 |
| Hs.416755 | NM_018357 | FLJ11196 | 15 | | down | | | | | Acheron |
| Hs.271643 | NM_018368 | C6orf209 | 6 | | down | | | | | Chromosome 6 open reading frame 209 |
| Hs.211828 | NM_018428 | HCA66 | 17 | up | | | | | | Hepatocellular carcinoma-associated antigen 66 |
| Hs.32148 | NM_018445 | SELS | 15 | | down | | | | | Selenoprotein S |
| Hs.477325 | NM_018456 | EAF2 | 3 | | up | | | | | ELL associated factor 2 |
| Hs.370102 | NM_018464 | C10orf70 | 10 | | | | up | | | Chromosome 10 open reading frame 70 |
| Hs.479766 | NM_018475 | TPARL | 4 | | | | | | down | TPA regulated locus |
| Hs.12126 | NM_018487 | HCA112 | 7;20;12 | down | | | | down | | Hepatocellular carcinoma-associated antigen 112 |
| Hs.207433 | NM_018557 | LRP1B | 2 | | down | | | | | Low density lipoprotein-related protein 1B (deleted in tumors) |
| Hs.435991 | NM_018569 | C4orf16 | 4 | | | | | | up | Chromosome 4 open reading frame 16 |
| Hs.519346 | NM_018695 | ERBB2IP | 5 | | down | | | | | Erbb2 interacting protein |
| Hs.47572 | NM_018696 | ELAC1 | 18 | up | up | | | | | ElaC homolog 1 (E. coli) |
| Hs.104980 | NM_018706 | DHTKD1 | 10 | | | up | | | | Dehydrogenase E1 and transketolase domain containing 1 |
| Hs.184062 | NM_018840 | C20orf24 | 20;10 | up | | | | | | Chromosome 20 open reading frame 24 |
| Hs.145256 | NM_018930 | PCDHB10 | 5 | | | | | down | | Protocadherin beta 10 |

| UniGene ID | Annotation | | Chr. | Direction of Change in SZ relative to Controls | | | | | | Name |
|---|---|---|---|---|---|---|---|---|---|---|
| | Acc | Symbol | | AnCg | CB | DLPFC | Nacc | PC | STG | |
| Hs.190518 | NM_018944 | C21orf45 | 21 | | | | | up | | Chromosome 21 open reading frame 45 |
| Hs.484686 | NM_018988 | GFOD1 | 6 | up | | | | | up | Glucose-fructose oxidoreductase domain containing 1 |
| Hs.440534 | NM_019022 | FLJ20793 | 18 | | down | | | | | FLJ20793 protein |
| Hs.288224 | NM_019051 | MRPL50 | 9 | | | up | | | | Mitochondrial ribosomal protein L50 |
| Hs.481836 | NM_019061 | PIP3AP | 5 | up | | | | | | Phosphatidylinositol-3-phosphate associated protein |
| Hs.140950 | NM_019065 | EFCBP2 | 16 | | | down | | | | EF hand calcium binding protein 2 |
| Hs.173524 | NM_019081 | LKAP | 16 | | | | | | up | Limkain b1 |
| Hs.466714 | NM_019088 | PD2 | 19 | | down | down | | | | Hypothetical protein F23149_1 |
| Hs.323396 | NM_019557 | LOC56181 | 1 | up | | | | | | Hypothetical protein RP1-317E23 |
| Hs.178011 | NM_019606 | FLJ20257 | 7 | up | | | | | | Hypothetical protein FLJ20257 |
| Hs.443529 | NM_019607 | FLJ11267 | 8 | | | | | | down | Hypothetical protein FLJ11267 |
| Hs.100890 | NM_019845 | RPRM | 2 | | up | | | | up | Reprimo, TP53 dependant G2 arrest mediator candidate |
| Hs.413083 | NM_019863 | F8 | X | | | | | | | Coagulation factor VIII, procoagulant component (hemophilia A) |
| Hs.133512 | NM_020119 | ZC3HAV1 | | up | | | | | | Zinc finger CCCH type, antiviral 1 |
| Hs.193226 | NM_020121 | UGCGL2 | 13 | | | | | down | | UDP-glucose ceramide glucosyltransferase-like 2 |
| Hs.109929 | NM_020137 | GRIPAP1 | | | | down | | | | GRIP1 associated protein 1 |
| Hs.262858 | NM_020143 | LOC56902 | 2 | | | | | | up | Putative 28 kDa protein |
| Hs.460242 | NM_020145 | SH3GLB2 | 9 | | | down | | | | SH3-domain GRB2-like endophilin B2 |
| Hs.160565 | NM_020154 | C15orf24 | 15 | | down | | | | | Chromosome 15 open reading frame 24 |
| Hs.250456 | NM_020162 | DHX33 | 17 | up | | | | | | DEAH (Asp-Glu-Ala-His) box polypeptide 33 |
| Hs.47649 | NM_020166 | MCCC1 | 3 | | down | | | | | Methylcrotonoyl-Coenzyme A carboxylase 1 (alpha) |
| Hs.42785 | NM_020186 | ACN9 | 7 | | | | | | up | ACN9 homolog (S. cerevisiae) |
| Hs.202011 | NM_020198 | GK001 | 17 | | | | | | down | GK001 protein |
| Hs.6434 | NM_020215 | C14orf132 | 14 | up | up | | | | | Chromosome 14 open reading frame 132 |
| Hs.127432 | NM_020234 | MDS009 | 15 | | | up | | | | X_009 protein |
| Hs.22065 | NM_020239 | CDC42SE1 | 1 | up | | | | | | CDC42 small effector 1 |
| Hs.118241 | NM_020247 | CABC1 | 1 | up | | | | | | Chaperone, ABC1 activity of bc1 complex like (S. pombe) |
| Hs.300404 | NM_020314 | MGC16824 | 16 | | down | | | | | Esophageal cancer associated protein |
| Hs.194408 | NM_020340 | KIAA1244 | 6 | up | | | | | | KIAA1244 |
| Hs.477869 | NM_020353 | PLSCR4 | 3 | | | | | down | | Phospholipid scramblase 4 |
| Hs.322901 | NM_020368 | SAS10 | 4 | | | up | | | | Disrupter of silencing 10 |
| Hs.390623 | NM_020383 | XPNPEP1 | 10 | | | | up | | | X-prolyl aminopeptidase (aminopeptidase P) 1, soluble |
| Hs.387755 | NM_020408 | C6orf149 | 6 | | | down | | | | Chromosome 6 open reading frame 149 |
| Hs.483841 | NM_020466 | DJ122O8.2 | 6 | | up | | | | down | Hypothetical protein dJ122O8.2 |

| Annotation | | | Direction of Change in SZ relative to Controls | | | | | | | Name |
|---|---|---|---|---|---|---|---|---|---|---|
| UniGene ID | Acc | Symbol | Chr. | AnCg | CB | DLPFC | Nacc | PC | STG | |
| Hs.481545 | NM_020546 | ADCY2 | 5 | | | up | | up | up | Adenylate cyclase 2 (brain) |
| Hs.104613 | NM_020640 | RP42 | 3 | | | up | | | | RP42 homolog |
| Hs.529951 | NM_020654 | SENP7 | 3 | | | | | down | | SUMO1/sentrin specific protease 7 |
| Hs.123450 | NM_020655 | JPH3 | 16 | | down | | | | | Kelch domain containing 4 |
| Hs.287374 | NM_020657 | ZNF304 | 19 | | down | | | | | Zinc finger protein 304 |
| Hs.283816 | NM_020660 | CX36 | 15 | | | down | | | | Connexin-36 |
| Hs.47166 | NM_020685 | C3orf14 | 3;11 | | | | up | | | Chromosome 3 open reading frame 14 |
| Hs.211252 | NM_020689 | SLC24A3 | 20 | | | | up | | | Solute carrier family 24 (sodium/potassium/calcium exchanger), member 3 |
| Hs.526401 | NM_020695 | TCEB3BP1 | 19 | | | | | down | | Transcription elongation factor B polypeptide 3 binding protein 1 |
| Hs.17255 | NM_020706 | SFRS15 | 21 | | up | | | | | Splicing factor, arginine/serine-rich 15 |
| Hs.434947 | NM_020727 | ZNF295 | 21 | | | | | down | | Zinc finger protein 295 |
| Hs.211751 | NM_020836 | KIAA1446 | 14 | | | down | | | | Brain-enriched guanylate kinase-associated protein |
| Hs.515351 | NM_020895 | KIAA1533 | 19 | up | | | | | | KIAA1533 |
| Hs.443891 | NM_020925 | KIAA1573 | 1 | | down | | | | | KIAA1573 protein |
| Hs.8453 | NM_020932 | MAGEE1 | | | | down | | | | Melanoma antigen, family E, 1 |
| Hs.368525 | NM_020992 | PDLIM1 | 10 | | up | | | | | PDZ and LIM domain 1 (elfin) |
| Hs.243994 | NM_021008 | DEAF1 | 11 | | | | up | | | Deformed epidermal autoregulatory factor 1 (Drosophila) |
| Hs.198760 | NM_021076 | NEFH | 22;20 | | | | up | | | Neurofilament, heavy polypeptide 200kDa |
| Hs.192215 | NM_021116 | ADCY1 | 7 | | | | up | | up | Adenylate cyclase 1 (brain) |
| Hs.437403 | NM_021129 | PP | 10 | | | up | | | | Pyrophosphatase (inorganic) |
| Hs.147119 | NM_021135 | RPS6KA2 | 6 | up | | | | | | Ribosomal protein S6 kinase, 90kDa, polypeptide 2 |
| Hs.154029 | NM_021170 | HES4 | 1 | | | down | | | | Hairy and enhancer of split 4 (Drosophila) |
| Hs.119889 | NM_021183 | RAP2C | X | | | | | down | | RAP2C, member of RAS oncogene family |
| Hs.445489 | NM_021200 | PLEKHB1 | 11,8; 12; 15;20 | | | | down | | | Pleckstrin homology domain containing, family B (evectins) member 1 |
| Hs.435106 | NM_021205 | RHOU | 1 | | | | | | down | Ras homolog gene family, member U |
| Hs.494854 | NM_021218 | C9orf80 | 9 | | | up | | | | Chromosome 9 open reading frame 80 |
| Hs.234282 | NM_021729 | VPS11 | 11 | | | | down | | down | Vacuolar protein sorting 11 (yeast) |
| Hs.301062 | NM_021808 | GALNT9 | 12 | up | up | | | | | UDP-N-acetyl-alpha-D-galactosamine:polypeptide N-acetylgalactosaminyltransferase 9 (GalNAc-T9) |
| Hs.269764 | NM_021813 | BACH2 | 6 | | up | | | | | BTB and CNC homology 1, basic leucine zipper transcription factor 2 |

| UniGene ID | Annotation | | Chr. | Direction of Change in SZ relative to Controls | | | | | | Name |
|---|---|---|---|---|---|---|---|---|---|---|
| | Acc | Symbol | | AnCg | CB | DLPFC | Nacc | PC | STG | |
| Hs.257341 | NM_021818 | SAV1 | 14 | | | | down | | | Salvador homolog 1 (Drosophila) |
| Hs.461954 | NM_021947 | SRR | 17 | down | | | | | down | Serine racemase |
| Hs.213050 | NM_021952 | ELAVL4 | 1 | | up | | | | | ELAV (embryonic lethal, abnormal vision, Drosophila)-like 4 (Hu antigen D) |
| Hs.329978 | NM_022087 | GALNT11 | 7 | | | | up | | | UDP-N-acetyl-alpha-D-galactosamine:polypeptide N-acetylgalactosaminyltransferase 11 (GalNAc-T11) |
| Hs.128866 | NM_022089 | HSA9947 | 1 | | | | up | | | Putative ATPase |
| Hs.247324 | NM_022100 | MRPS14 | 1 | | | up | | | | Mitochondrial ribosomal protein S14 |
| Hs.198158 | NM_022129 | MAWBP | 10 | down | | | | | | MAWD binding protein |
| Hs.488591 | NM_022479 | WBSCR17 | 7 | | up | | | | | Williams-Beuren syndrome chromosome region 17 |
| Hs.480356 | NM_022553 | VPS52 | 6 | down | | up | | | | Vacuolar protein sorting 52 (yeast) |
| Hs.510265 | NM_022731 | NUCKS | 1 | down | | | | | | Nuclear ubiquitous casein kinase and cyclin-dependent kinase substrate |
| Hs.440880 | NM_022753 | FLJ12903 | 1 | | down | | | | | Hypothetical protein FLJ12903 |
| Hs.369440 | NM_022754 | SFXN1 | 5 | | | | up | | down | Sideroflexin 1 |
| Hs.284630 | NM_022771 | TBC1D15 | 12 | | | | down | | | TBC1 domain family, member 15 |
| Hs.27836 | NM_022823 | FNDC4 | 2 | down | | down | | | | Fibronectin type III domain containing 4 |
| Hs.370549 | NM_022893 | BCL11A | 2 | | | | | down | | B-cell CLL/lymphoma 11A (zinc finger protein) |
| Hs.203559 | NM_022915 | MRPL44 | 2 | | | | | | up | Mitochondrial ribosomal protein L44 |
| Hs.239154 | NM_023039 | ANKRA2 | 5;3 | | | | down | | | Ankyrin repeat, family A (RFXANK-like), 2 |
| Hs.146679 | NM_023071 | SPATS2 | 12 | | | | up | | | Spermatogenesis associated, serine-rich 2 |
| Hs.169615 | NM_023080 | FLJ20989 | 8 | up | | | | | | Hypothetical protein FLJ20989 |
| Hs.225641 | NM_023923 | PHACTR4 | 1 | | | | | | down | Phosphatase and actin regulator 4 |
| Hs.169054 | NM_023928 | AACS | 12 | | | | up | up | | Acetoacetyl-CoA synthetase |
| Hs.157160 | NM_023936 | MRPS34 | 16 | up | | up | | | | Mitochondrial ribosomal protein S34 |
| Hs.458367 | NM_024026 | MRP63 | 13;8 | up | | up | | | up | Mitochondrial ribosomal protein 63 |
| Hs.15580 | NM_024075 | LENG5 | 19 | | | up | | | | Leukocyte receptor cluster (LRC) member 5 |
| Hs.59804 | NM_024077 | SECISBP2 | 9;17 | | | | | | | SECIS binding protein 2 |
| Hs.412939 | NM_024090 | ELOVL6 | 4 | | | | | up | | ELOVL family member 6, elongation of long chain fatty acids (FEN1/Elo2, SUR4/Elo3-like, yeast) |
| Hs.441734 | NM_024091 | MGC5297 | 5 | down | | | | | | Hypothetical protein MGC5297 |
| Hs.177688 | NM_024303 | ZSCAN5 | 19 | down | | | | | | Zinc finger and SCAN domain containing 5 |
| Hs.28144 | NM_024333 | FSD1 | 19 | | | | up | | | Fibronectin type 3 and SPRY domain containing 1 |
| Hs.499205 | NM_024336 | IRX3 | 16 | | down | | | | | Iroquois homeobox protein 3 |
| Hs.118394 | NM_024345 | MGC10765 | 9 | | down | | | | | Hypothetical protein MGC10765 |

| UniGene ID | Annotation | | | Direction of Change in SZ relative to Controls | | | | | | Name |
|---|---|---|---|---|---|---|---|---|---|---|
| | Acc | Symbol | Chr. | AnCg | CB | DLPFC | Nacc | PC | STG | |
| Hs.211914 | NM_024407 | NDUFS7 | 19 | up | | | | | | NADH dehydrogenase (ubiquinone) Fe-S protein 7, 20kDa (NADH-coenzyme Q reductase) |
| Hs.485004 | NM_024493 | ZNF306 | 6 | down | | | down | | | Zinc finger protein 306 |
| Hs.250693 | NM_024498 | ZNF117 | 7;19 | down | | | | | | Krueppel-related zinc finger protein |
| Hs.460568 | NM_024516 | MGC4606 | 16 | | down | | | | | Hypothetical protein MGC4606 |
| Hs.211441 | NM_024517 | PHF2 | 9 | | | | | down | | PHD finger protein 2 |
| Hs.443789 | NM_024581 | C6orf60 | 6 | | | | | | down | Chromosome 6 open reading frame 60 |
| Hs.470679 | NM_024583 | SCRN3 | 2 | | down | | | | | Secernin 3 |
| Hs.39311 | NM_024592 | SRD5A2L | 4 | | | up | | | | Steroid 5 alpha-reductase 2-like |
| Hs.293563 | NM_024595 | FLJ12666 | 1 | | down | | | | | Hypothetical protein FLJ12666 |
| Hs.200943 | NM_024611 | NARG2 | 15 | up | | | | | | NMDA receptor regulated 2 |
| Hs.317340 | NM_024683 | FLJ22729 | 17 | up | | | | | | Hypothetical protein FLJ22729 |
| Hs.445826 | NM_024686 | FLJ23033 | 1 | up | | | | | | Hypothetical protein FLJ23033 |
| Hs.121915 | NM_024742 | ARMC5 | 16 | | | down | | | | Armadillo repeat containing 5 |
| Hs.468349 | NM_024766 | FLJ23451 | 2 | down | | | | | | Hypothetical protein FLJ23451 |
| Hs.443061 | NM_024810 | CXorf45 | X | | | | | down | | Chromosome X open reading frame 45 |
| Hs.533446 | NM_024812 | BAALC | 8 | up | | | | | | Brain and acute leukemia, cytoplasmic |
| Hs.187377 | NM_024847 | TMC7 | 16 | | up | | | | | Transmembrane channel-like 7 |
| Hs.193170 | NM_024859 | FLJ21687 | X | | up | | | | | PDZ domain containing, X chromosome |
| Hs.478465 | NM_024871 | FLJ12748 | 3 | | | | down | | down | Hypothetical protein FLJ12748 |
| Hs.456507 | NM_024874 | PKD1-like | 1 | up | | | | | | Polycystic kidney disease 1-like |
| Hs.130712 | NM_024876 | ADCK4 | 19 | | up | | | | | AarF domain containing kinase 4 |
| Hs.374147 | NM_024943 | MECT1 | 4 | | | down | | | | Hypothetical protein FLJ23235 |
| Hs.371096 | NM_025021 | MECT1 | 19 | up | | | | | | Mucoepidermoid carcinoma translocated 1 |
| Hs.260555 | NM_025057 | C14orf45 | 14 | | up | | | | | Chromosome 14 open reading frame 45 |
| Hs.24808 | NM_025073 | FLJ21168 | 1 | | up | | | | | Hypothetical protein FLJ21168 |
| Hs.302051 | NM_025109 | MYOHD1 | | | | | | | down | Myosin head domain containing 1 |
| Hs.288945 | NM_025147 | FLJ13448 | 2 | | | down | | | | Hypothetical protein FLJ13448 |
| Hs.288981 | NM_025152 | C14orf127 | 14 | | | up | | | | Chromosome 14 open reading frame 127 |
| Hs.301526 | NM_025188 | TRIM45 | 1 | | | up | | | | Tripartite motif-containing 45 |
| Hs.443723 | NM_025196 | GRPEL1 | 4 | | down | | | | | GrpE-like 1, mitochondrial (E. coli) |
| Hs.434075 | NM_025205 | MED28 | 4;1 | | | | | up | | Mediator of RNA polymerase II transcription, subunit 28 homolog (yeast) |
| Hs.329327 | NM_025235 | TNKS2 | 10 | | | | down | | | Tankyrase, TRF1-interacting ankyrin-related ADP-ribose polymerase 2 |

| | Annotation | | | Direction of Change in SZ relative to Controls | | | | | | | |
|---|---|---|---|---|---|---|---|---|---|---|---|
| UniGene ID | Acc | Symbol | Chr. | AnCg | CB | DLPFC | Nacc | PC | STG | Name |
| Hs.118354 | NM_025263 | PRR3 | 6;4 | up | | | | | | Proline rich 3 |
| Hs.189445 | NM_030583 | MATN2 | 8 | | | | | down | | Matrilin 2 |
| Hs.127126 | NM_030627 | CPEB4 | 5 | | | | | down | | Cytoplasmic polyadenylation element binding protein 4 |
| Hs.11067 | NM_030630 | C17orf28 | 17 | down | | | | | | Chromosome 17 open reading frame 28 |
| Hs.209561 | NM_030650 | KIAA1715 | 2 | | | | | down | | KIAA1715 |
| Hs.449628 | NM_030759 | NRBF2 | 10;8;1 | up | | | | | | Nuclear receptor binding factor 2 |
| Hs.177841 | NM_030762 | BHLHB3 | 12 | | | | down | | | Basic helix-loop-helix domain containing, class B, 3 |
| Hs.480519 | NM_030821 | PLA2G12A | 4 | | | | | up | | Phospholipase A2, group XIIA |
| Hs.538547 | NM_030920 | ANP32E | 1 | | down | | | | | Acidic (leucine-rich) nuclear phosphoprotein 32 family, member E |
| Hs.436996 | NM_030948 | PHACTR1 | 6 | down | | | | | | Phosphatase and actin regulator 1 |
| Hs.267120 | NM_030963 | RNF146 | 6 | | down | | | | | Ring finger protein 146 |
| Hs.300816 | NM_030981 | RAB1B | 11;9;2 | up | | | up | | | RAB1B, member RAS oncogene family |
| Hs.301048 | NM_031216 | SEH1L | 18 | | | up | | | | SEH1-like (S. cerevisiae) |
| Hs.247280 | NM_031227 | C20orf18 | 20;18 | | up | | | | | Chromosome 20 open reading frame 18 |
| Hs.109051 | NM_031286 | SH3BGRL3 | 1 | up | | | | | | SH3 domain binding glutamic acid-rich protein like 3 |
| Hs.110695 | NM_031287 | SF3B5 | 6;20;12 | up | | | | | up | Splicing factor 3b, subunit 5, 10kDa |
| Hs.270437 | NM_031361 | COL4A3BP | 5 | | | | up | | | Collagen, type IV, alpha 3 (Goodpasture antigen) binding protein |
| Hs.378808 | NM_032025 | eIF2A | 3 | down | down | | | down | | Eukaryotic translation initiation factor (eIF) 2A |
| Hs.465642 | NM_032108 | SEMA6B | 19 | up | | | | | | Sema domain, transmembrane domain (TM), and cytoplasmic domain, (semaphorin) 6B |
| Hs.501793 | NM_032127 | DKFZp566M1046 | 11 | | | down | | | | Hypothetical protein DKFZp566M1046 |
| Hs.100914 | NM_032142 | Cep192 | 18 | | | | | down | | Centrosomal protein 192 kDa |
| Hs.519326 | NM_032151 | DCOHM | 5 | | up | | | | | Dimerization cofactor of hepatocyte nuclear factor 1 (HNF1) from muscle |
| Hs.399984 | NM_032168 | FLJ12519 | | | | | | down | down | Hypothetical protein FLJ12519 |
| Hs.441378 | NM_032169 | FLJ12592 | 3 | up | | | | | | Putative acyl-CoA dehydrogenase |
| Hs.339612 | NM_032177 | PHAX | 5 | | | up | | | up | RNA U, small nuclear RNA export adaptor (phosphorylation regulated) |
| Hs.381214 | NM_032261 | C21orf56 | 21 | | | | | | up | Chromosome 21 open reading frame 56 |

| UniGene ID | Acc | Symbol | Chr. | AnCg | CB | DLPFC | Nacc | PC | STG | Name |
|---|---|---|---|---|---|---|---|---|---|---|
| Hs.19673 | NM_032272 | MAF1 | 16 | up | | | | | | Homolog of yeast MAF1 |
| Hs.124015 | NM_032304 | HAGHL | 16 | | | | | | down | Hydroxyacylglutathione hydrolase-like |
| Hs.9088 | NM_032305 | MGC3200 | 1 | | | | | | up | Hypothetical protein LOC284615 |
| Hs.513315 | NM_032349 | SDOS | 16 | up | | | | | | Hypothetical protein MGC11275 |
| Hs.239500 | NM_032366 | MGC13114 | 16 | up | | | | | | Hypothetical protein MGC13114 |
| Hs.277154 | NM_032380 | GFM2 | 5 | | | | | | | G elongation factor, mitochondrial 2 |
| Hs.438709 | NM_032446 | MEGF10 | 5 | | up | | | | up | MEGF10 protein |
| Hs.437126 | NM_032496 | ARHGAP9 | 12 | | | | | | down | Rho GTPase activating protein 9 |
| Hs.144527 | NM_032507 | PGBD1 | 6 | down | | | | | up | PiggyBac transposable element derived 1 |
| Hs.486010 | NM_032511 | C6orf168 | 6 | | | down | | | | Chromosome 6 open reading frame 168 |
| Hs.293753 | NM_032515 | BOK | 2 | | up | | | | | BCL2-related ovarian killer |
| Hs.163642 | NM_032536 | NTNG2 | 9 | | down | | | | | Netrin G2 |
| Hs.501106 | NM_032550 | KIAA1914 | 10 | down | | | | | | KIAA1914 |
| Hs.387255 | NM_032569 | N-PAC | 16 | | | up | | | | Cytokine-like nuclear factor n-pac |
| Hs.145010 | NM_032576 | CYorf15B | Y | | up | | | | | Chromosome Y open reading frame 15B |
| Hs.132868 | NM_032582 | USP32 | 17 | up | | | | | | Ubiquitin specific protease 32 |
| Hs.277101 | NM_032609 | COX4I2 | 20 | up | | | | | | Cytochrome c oxidase subunit IV isoform 2 (lung) |
| Hs.154140 | NM_032623 | OSAP | 4 | | up | | | | | Ovary-specific acidic protein |
| Hs.129634 | NM_032630 | CINP | 14;12 | | | up | | | | Cyclin-dependent kinase 2-interacting protein |
| Hs.459379 | NM_032687 | CYHR1 | 8 | up | | | | | | Cysteine and histidine rich 1 |
| Hs.436035 | NM_032704 | TUBA6 | 12 | down | | | | | | Tubulin alpha 6 |
| Hs.476972 | NM_032778 | MINA | 3 | | up | | | up | | MYC induced nuclear antigen |
| Hs.401537 | NM_032802 | SPPL2A | 15 | | | | | | down | Putative intramembrane cleaving protease |
| Hs.435948 | NM_032810 | ATAD1 | 10 | | | | | | down | ATPase family, AAA domain containing 1 |
| Hs.190983 | NM_032813 | FLJ14624 | 13 | | | | | | down | Hypothetical protein FLJ14624 |
| Hs.461113 | NM_032830 | CIRH1A | 16 | | down | | | | | Cirrhosis, autosomal recessive 1A (cirhin) |
| Hs.520287 | NM_032870 | C6orf111 | 6 | down | | | | | | Chromosome 6 open reading frame 111 |
| Hs.388645 | NM_032901 | MGC14288 | 12 | up | | | | | | Hypothetical protein MGC14288 |
| Hs.406788 | NM_032932 | RAB11FIP4 | 4 | up | | | | | | RAB11 family interacting protein 4 (class II) |
| Hs.505676 | NM_033082 | CIP29 | 12 | up | | | | | | Cytokine induced protein 29 kDa |
| Hs.292986 | NM_033115 | MGC16169 | 4 | | | up | | | | Hypothetical protein MGC16169 |
| Hs.224843 | NM_033210 | ZNF502 | 3 | | up | | | | | Zinc finger protein 502 |
| Hs.370530 | NM_033220 | TRIM14 | 9 | down | | | | | | Tripartite motif-containing 14 |
| Hs.297452 | NM_033260 | FOXQ1 | 6 | | | | | | down | Forkhead box Q1 |
| Hs.27695 | NM_033291 | MID1 | X | | up | | | | | Midline 1 (Opitz/BBB syndrome) |

| UniGene ID | Annotation | | | Direction of Change in SZ relative to Controls | | | | | | Name |
|---|---|---|---|---|---|---|---|---|---|---|
| | Acc | Symbol | Chr. | AnCg | CB | DLPFC | Nacc | PC | STG | |
| Hs.335033 | NM_033427 | CTTNBP2 | 7 | | up | | | | | Cortactin binding protein 2 |
| Hs.348390 | NM_033439 | C9orf26 | 9 | | down | | | down | | Chromosome 9 open reading frame 26 (NF-HEV) |
| Hs.348262 | NM_033495 | KLHL13 | X | | up | | | | | Kelch-like 13 (Drosophila) |
| Hs.347270 | NM_033554 | HLA-DPA1 | 6 | | down | | down | | | Major histocompatibility complex, class II, DP alpha 1 |
| Hs.200600 | NM_052837 | SCAMP3 | 1 | up | | | | | | Secretory carrier membrane protein 3 |
| Hs.440092 | NM_052839 | PANX2 | X | | | down | | | | Pannexin 2 |
| Hs.320823 | NM_052865 | C20orf72 | 20 | | | | | down | | Chromosome 20 open reading frame 72 |
| Hs.12082 | NM_053000 | TIGA1 | 20 | up | | | | | | TIGA1 |
| Hs.408427 | NM_053041 | COMMD7 | 20 | up | | | | | | COMM domain containing 7 |
| Hs.231029 | NM_053045 | MGC14327 | 9 | | down | | | | | Hypothetical protein MGC14327 |
| Hs.203717 | NM_054034 | FN1 | 2 | | | | | | down | Fibronectin 1 |
| Hs.410830 | NM_058190 | C21orf70 | 21 | up | | | | | | Chromosome 21 open reading frame 70 |
| Hs.287518 | NM_080415 | PNUTL2 | 17 | | | | down | | | Peanut-like 2 (Drosophila) |
| Hs.55940 | NM_080430 | SELM | | up | | | | | | Selenoprotein M |
| Hs.179080 | NM_080552 | SLC32A1 | 20 | | | | | up | | Solute carrier family 32 (GABA vesicular transporter), member 1 |
| Hs.156506 | NM_080656 | MGC13017 | 5 | | up | | | | | Similar to RIKEN cDNA A430101B06 gene |
| Hs.264208 | NM_080667 | MGC15407 | 2 | | down | | | | | Similar to RIKEN cDNA 4931428D14 gene |
| Hs.269577 | NM_080841 | VPS16 | 20 | | down | up | | | | Protein tyrosine phosphatase, receptor type, A |
| Hs.135805 | NM_080875 | LOC142678 | 1 | up | | | | | | Skeletrophin |
| Hs.464422 | NM_130386 | COLEC12 | 18 | | down | | | | | Collectin sub-family member 12 |
| Hs.304578 | NM_130442 | ELMO1 | 7 | | | down | | | | Engulfment and cell motility 1 (ced-12 homolog, C. elegans) |
| Hs.196482 | NM_130469 | JDP2 | 14 | | | down | | | | Jun dimerization protein 2 |
| Hs.16258 | NM_130781 | RAB24 | 5 | up | | | | | | RAB24, member RAS oncogene family |
| Hs.483259 | NM_130809 | LOC133619 | 5 | | | | | | down | Hypothetical protein MGC12103 |
| Hs.103315 | NM_133476 | ZNF384 | 12 | down | | | | | | Zinc finger protein 384 |
| Hs.156316 | NM_133503 | DCN | 12 | | down | | | | | Decorin |
| Hs.156316 | NM_133504 | DCN | 12 | | down | | | | | Decorin |
| Hs.411488 | NM_138290 | RPIB9 | 7 | | up | | | | | Rap2-binding protein 9 |
| Hs.264345 | NM_138330 | TIZ | 19 | | | | | up | | TRAF6-inhibitory zinc finger protein |
| Hs.29645 | NM_138364 | LOC90826 | 4 | | | up | | | | Hypothetical protein BC004337 |
| Hs.370055 | NM_138409 | C6orf117 | 6 | | | | | up | | Chromosome 6 open reading frame 117 |
| Hs.460487 | NM_138414 | LOC112869 | 16 | | | | | | up | Hypothetical protein BC011981 |
| Hs.348411 | NM_138467 | LOC127253 | 1 | | | up | | | | Hypothetical protein BC009514 |

| | Annotation | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.444338 | NM_138698 | LOC91431 | 4 | | | down | | | | Prematurely terminated mRNA decay factor-like |
| Hs.129159 | NM_138701 | C7orf11 | 7 | up | | | | | | Chromosome 7 open reading frame 11 |
| Hs.484371 | NM_139068 | MAPK9 | 5 | down | | down | | | | Mitogen-activated protein kinase 9 |
| Hs.356523 | NM_139124 | MAPK8IP2 | 22; 20;12 | | down | | | | | Mitogen-activated protein kinase 8 interacting protein 2 |
| Hs.21187 | NM_139169 | TRUB1 | 10 | | | up | | | | TruB pseudouridine (psi) synthase homolog 1 (E. coli) |
| Hs.33470 | NM_139278 | LGI3 | 8 | | | | | up | | Leucine-rich repeat LGI family, member 3 |
| Hs.65256 | NM_139284 | LGI4 | 19 | | down | | | | | Leucine-rich repeat LGI family, member 4 |
| Hs.173034 | NM_139316 | AMPH | 7 | | | | up | | | Amphiphysin (Stiff-Man syndrome with breast cancer 128kDa autoantigen) |
| Hs.193163 | NM_139351 | BIN1 | 2;11 | | up | | | | | Bridging integrator 1 |
| Hs.371240 | NM_144497 | AKAP12 | 6 | | | | | | up | A kinase (PRKA) anchor protein (gravin) 12 |
| Hs.469264 | NM_144563 | RPIA | 2 | | down | | | | | Ribose 5-phosphate isomerase A (ribose 5-phosphate epimerase) |
| Hs.7962 | NM_144584 | FLJ30525 | 1 | | | up | | | | Hypothetical protein FLJ30525 |
| Hs.432780 | NM_144638 | MGC29956 | 3 | up | | | | | | Hypothetical protein MGC29956 |
| Hs.55150 | NM_144647 | MGC26610 | 5 | down | | | | | | Hypothetical protein MGC26610 |
| Hs.12381 | NM_144669 | FLJ31978 | 12 | | | | | up | | Hypothetical protein FLJ31978 |
| Hs.283828 | NM_144770 | RBM11 | 21 | down | | | | | | RNA binding motif protein 11 |
| Hs.502223 | NM_144981 | FLJ25059 | 11 | up | | | | | | Hypothetical protein FLJ25059 |
| Hs.533086 | NM_144996 | ARL21L1 | 3 | up | | | | | | ADP-ribosylation factor-like 2-like 1 |
| Hs.413359 | NM_145030 | MGC22793 | 7 | | | | | down | down | Hypothetical protein MGC22793 |
| Hs.293818 | NM_145043 | NEIL2 | 8 | | | | | | up | Nei like 2 (E. coli) |
| Hs.202207 | NM_145047 | NOR1 | 1 | | | up | | | | Oxidored-nitro domain-containing protein |
| Hs.515490 | NM_145056 | MGC15476 | 19 | | down | | | | | Thymus expressed gene 3-like |
| Hs.294145 | NM_145265 | LOC133957 | | | | up | | | | Similar to RIKEN cDNA 0610011N22 |
| Hs.418495 | NM_145267 | C6orf57 | 6 | down | | | | | | Chromosome 6 open reading frame 57 |
| Hs.522992 | NM_145306 | C10orf35 | 10 | | up | | | | | Chromosome 10 open reading frame 35 |
| Hs.21938 | NM_148907 | OSBPL9 | 1 | | | | | down | | Oxysterol binding protein-like 9 |
| Hs.15783 | NM_152302 | C20orf158 | 20 | | down | | | | | Chromosome 20 open reading frame 158 |
| Hs.434914 | NM_152330 | C14orf31 | 14 | | | down | | down | | Chromosome 14 open reading frame 31 |
| Hs.374556 | NM_152339 | MGC26885 | 16 | | | down | | | | Hypothetical protein MGC26885 |
| Hs.135181 | NM_152361 | FLJ38944 | 19 | | up | | | | | Hypothetical protein FLJ38944 |
| Hs.462033 | NM_152371 | MGC26818 | 1 | | | down | | | down | Hypothetical protein MGC26818 |
| Hs.523413 | NM_152372 | MYOM3 | 1 | | | up | | | | Myomesin family, member 3 |

| UniGene ID | Annotation | | | Direction of Change in SZ relative to Controls | | | | | | Name |
|---|---|---|---|---|---|---|---|---|---|---|
| | Acc | Symbol | Chr. | AnCg | CB | DLPFC | Nacc | PC | STG | |
| Hs.434945 | NM_152379 | DKFZp547B1713 | 1 | | | | | | down | Hypothetical protein DKFZp547B1713 |
| Hs.524828 | NM_152437 | DKFZp761B128 | 12 | up | | | | | | Hypothetical protein DKFZp761B128 |
| Hs.520192 | NM_152608 | FLJ35382 | 1 | | | | | down | | Hypothetical protein FLJ35382 |
| Hs.400698 | NM_152618 | FLJ35630 | 4 | up | | | | | | Hypothetical protein FLJ35630 |
| Hs.507584 | NM_152705 | MGC9850 | 13 | | | | | | up | Polymerase (RNA) I polypeptide D, 16kDa |
| Hs.487564 | NM_152745 | NXPH1 | 7 | down | | | | | | Neurexophilin 1 |
| Hs.534591 | NM_152766 | MGC40107 | 17 | up | | | | up | | Hypothetical protein MGC40107 |
| Hs.135997 | NM_152773 | LOC116211 | 3 | | | | | | up | Hypothetical protein BC013113 |
| Hs.200100 | NM_152793 | Ells1 | 7 | up | | up | | | | Hypothetical protein Ells1 |
| Hs.12102 | NM_152827 | SNX3 | 6;7 | up | | | | | | Sorting nexin 3 |
| Hs.27788 | NM_153034 | ZNF488 | 10 | up | | | | | | Zinc finger protein 488 |
| Hs.390567 | NM_153048 | FYN | 6;20 | up | | | | | | FYN oncogene related to SRC, FGR, YES |
| Hs.504943 | NM_153207 | AEBP2 | 12 | | | | | down | | AE binding protein 2 |
| Hs.460217 | NM_153208 | MGC35048 | 16 | | down | | | | | Hypothetical protein MGC35048 |
| Hs.180257 | NM_153231 | ZNF550 | 19 | | down | | | | | Zinc finger protein 550 |
| Hs.436743 | NM_153233 | FLJ36445 | 19 | | up | | | | | Hypothetical protein FLJ36445 |
| Hs.128188 | NM_153234 | C5orf11 | 5 | | down | | | | | Chromosome 5 open reading frame 11 |
| Hs.511991 | NM_153240 | NPHP3 | 3 | | | | | | down | Nephronophthisis 3 (adolescent) |
| Hs.399779 | NM_153266 | MGC33486 | | up | | | | | | Hypothetical protein MGC33486 |
| Hs.171001 | NM_153456 | HS6ST3 | 13 | | | down | | | | Heparan sulfate 6-O-sulfotransferase 3 |
| Hs.156723 | NM_153498 | CAMK1D | 10 | down | | | | | | Calcium/calmodulin-dependent protein kinase ID |
| Hs.484195 | NM_153607 | LOC153222 | 5 | | | up | | | | Adult retina protein |
| Hs.40910 | NM_153634 | CPNE8 | 12 | | | up | | | | Copine VIII |
| Hs.435080 | NM_153690 | FAM43A | 3 | | up | | | | | Family with sequence similarity 43, member A |
| Hs.110477 | NM_153741 | DPM3 | 1 | up | | | | | | Dolichyl-phosphate mannosyltransferase polypeptide 3 |
| Hs.511774 | NM_153750 | C21orf81 | 18 | down | | | | | down | Chromosome 21 open reading frame 81 |
| Hs.463985 | NM_170741 | KCNJ16 | 17 | | | | | | down | Potassium inwardly-rectifying channel, subfamily J, member 16 |
| Hs.297343 | NM_172226 | CAMKK2 | 12 | | | | up | | | Calcium/calmodulin-dependent protein kinase kinase 2, beta |
| Hs.131686 | NM_172386 | ABCA9 | 17 | down | | | | | | ATP-binding cassette, sub-family A (ABC1), member 9 |
| Hs.132439 | NM_173054 | RELN | 7 | down | | | | down | | Reelin |
| Hs.165258 | NM_173173 | NR4A2 | 2 | down | | | | | | Nuclear receptor subfamily 4, group A, member 2 |

| UniGene ID | Annotation Acc | Symbol | Chr. | AnCg | CB | DLPFC | Nacc | PC | STG | Name |
|---|---|---|---|---|---|---|---|---|---|---|
| Hs.31422 | NM_173468 | MOBKL1A | 4 | up | | | | | | MOB1, Mps One Binder kinase activator-like 1A (yeast) |
| Hs.513424 | NM_173501 | LOC146174 | 16 | up | | | | | | Hypothetical protein LOC146174 |
| Hs.420244 | NM_173642 | MGC47816 | 1 | | | | | up | | Hypothetical protein MGC47816 |
| Hs.323482 | NM_173680 | MGC33584 | 7 | | | | | | up | Hypothetical protein MGC33584 |
| Hs.418198 | NM_173797 | PAPD4 | 5 | | | | | down | down | PAP associated domain containing 4 |
| Hs.356697 | NM_173827 | FLJ38991 | 4 | up | | | | | | Hypothetical protein FLJ38991 |
| Hs.121663 | NM_173848 | LOC138046 | 8 | | | | up | | | Hypothetical protein LOC138046 |
| Hs.436405 | NM_174855 | IDH3B | 20; 6;1 | | down | | | | | Isocitrate dehydrogenase 3 (NAD+) beta |
| Hs.4295 | NM_174871 | PSMD12 | 17 | | | down | | | | Proteasome (prosome, macropain) 26S subunit, non-ATPase, 12 |
| Hs.355606 | NM_174909 | MGC23909 | | up | | | | | | Hypothetical protein MGC23909 |
| Hs.534579 | NM_174923 | MGC31967 | 9 | | | down | | | | Hypothetical protein MGC31967 |
| Hs.321709 | NM_175567 | P2RX4 | 12;9 | | | | | | up | Purinergic receptor P2X, ligand-gated ion channel, 4 |
| Hs.406062 | NM_175614 | NDUFA11 | 19 | up | | up | | | | NADH dehydrogenase (ubiquinone) 1 alpha subcomplex, 11, 14.7kDa |
| Hs.251673 | NM_175849 | DNMT3B | 20 | | up | | | | | DNA (cytosine-5-)-methyltransferase 3 beta |
| Hs.448218 | NM_175885 | MGC33846 | 11 | | down | | | | | Hypothetical protein MGC33846 |
| Hs.203 | NM_176875 | CCKBR | 11 | | | down | | | | Cholecystokinin B receptor |
| Hs.287636 | NM_177963 | SYT12 | 11 | | | | | | down | Synaptotagmin XII |
| Hs.425383 | NM_178124 | CXorf40 | X;12 | | | | up | | | Chromosome X open reading frame 40 |
| Hs.471917 | NM_178579 | PSMF1 | 20 | | | up | | | | Proteasome (prosome, macropain) inhibitor subunit 1 (PI31) |
| Hs.63236 | NM_181465 | MRPL55 | 1 | up | | | | | | Mitochondrial ribosomal protein L55 |
| Hs.464697 | NM_181483 | C18orf1 | 18 | | up | | | | | Chromosome 18 open reading frame 1 |
| Hs.11900 | NM_181485 | ZGPAT | 20 | | down | | | | | Zinc finger, CCCH-type with G patch domain |
| Hs.433422 | NM_181716 | PRR6 | | | | up | | | up | Proline rich 6 |
| Hs.126137 | NM_181866 | BACH | 1 | | | up | | | | Brain acyl-CoA hydrolase |
| Hs.479853 | NM_182472 | EPHA5 | 4 | | up | | up | | | EPH receptor A5 |
| Hs.116567 | NM_182491 | LOC90637 | 7 | up | | | | | | Hypothetical protein LOC90637 |
| Hs.437336 | NM_182523 | MGC61571 | 3 | | | up | | | | Hypothetical protein MGC61571 |
| Hs.200668 | NM_182661 | CERK | 22 | | | | | | up | Ceramide kinase |
| Hs.529735 | NM_182662 | AADAT | 4 | down | | | | | | Aminoadipate aminotransferase |
| Hs.497579 | NM_182665 | RASSF5 | 1 | | up | | | | | Ras association (RalGDS/AF-6) domain family 5 |
| Hs.207157 | NM_182703 | LOC348094 | 15 | down | | | | | | Hypothetical protein LOC348094 |

| | Annotation | | | Direction of Change in SZ relative to Controls | | | | | | |
|---|---|---|---|---|---|---|---|---|---|---|
| UniGene ID | Acc | Symbol | Chr. | AnCg | CB | DLPFC | Nacc | PC | STG | Name |
| Hs.310537 | NM_182734 | PLCB1 | 20 | | | | up | | | Phospholipase C, beta 1 (phosphoinositide-specific) |
| Hs.472101 | NM_182797 | PLCB4 | 20 | | | up | | | | Phospholipase C, beta 4 |
| Hs.380021 | NM_182931 | MLL5 | | | | up | | | | Myeloid/lymphoid or mixed-lineage leukemia 5 (trithorax homolog, Drosophila) |
| Hs.414099 | NM_183010 | TNRC5 | 6;20 | | | down | | up | | Trinucleotide repeat containing 5 |
| Hs.446240 | NM_183048 | PRKCBP1 | 20 | | up | | up | | | Protein kinase C binding protein 1 |
| Hs.109087 | NM_183075 | CYP2U1 | 4 | down | | | | | | Cytochrome P450, family 2, subfamily U, polypeptide 1 |
| Hs.298651 | NM_183236 | RAB27A | 15 | down | | | | | | RAB27A, member RAS oncogene family |
| Hs.203634 | NM_183239 | GSTO2 | 10 | | | up | | | | Glutathione S-transferase omega 2 |
| Hs.317095 | NM_183243 | IMPDH1 | 7;10 | | | | up | | up | IMP (inosine monophosphate) dehydrogenase 1 |
| Hs.191540 | NM_184042 | COH1 | 8 | down | | | | | | Cohen syndrome 1 |
| Hs.291079 | NM_194279 | HBLD1 | 14 | up | | | | | | HESB like domain containing 1 |
| Hs.268668 | NM_194285 | FLJ39441 | 11 | | down | | | | | Hypothetical protein FLJ39441 |
| Hs.465337 | NM_194449 | PLEKHE1 | 18 | | | | | | down | Pleckstrin homology domain containing, family E (with leucine rich repeats) member 1 |
| Hs.274479 | NM_197972 | NME7 | 1 | up | up | up | | up | | Non-metastatic cells 7, protein expressed in (nucleoside-diphosphate kinase) |
| Hs.149500 | NM_198038 | NUDT9 | 4 | up | | | | | | Nudix (nucleoside diphosphate linked moiety X)-type motif 9 |
| Hs.76662 | NM_198045 | ZDHHC16 | 10 | up | | up | | | | Zinc finger, DHHC domain containing 16 |
| Hs.465838 | NM_198058 | ZNF266 | 19 | | down | | down | | | Zinc finger protein 266 |
| Hs.20521 | NM_198318 | HRMT1L2 | 19 | | | | up | | | HMT1 hnRNP methyltransferase-like 2 (S. cerevisiae) |
| Hs.494155 | NM_198394 | C9orf85 | 9 | up | | | | | | Chromosome 9 open reading frame 85 |
| Hs.446414 | NM_198793 | CD47 | 3 | | | up | | | | CD47 antigen (Rh-related antigen, integrin-associated signal transducer) |
| Hs.71941 | NM_198867 | MGC15677 | | | | | | down | | Hypothetical protein MGC15677 |
| Hs.515032 | NM_199054 | MKNK2 | 19 | | | | | | down | MAP kinase interacting serine/threonine kinase 2 |
| Hs.449009 | NM_199121 | WARP | 1 | | | | down | | | Von Willebrand factor A domain-related protein |
| Hs.528335 | NM_199138 | FLJ25477 | 13 | | | | | | down | Hypothetical protein FLJ25477 |
| Hs.274959 | NM_199167 | CLUL1 | 18 | | up | | | | | Clusterin-like 1 (retinal) |
| Hs.517155 | NM_199170 | TMEPAI | 20 | up | | | | | | Transmembrane, prostate androgen induced RNA |
| Hs.13645 | NM_199297 | THY28 | | up | | | | | | Thymocyte protein thy28 |
| Hs.13645 | NM_199298 | THY28 | 11;1 | up | down | | | | | Thymocyte protein thy28 |
| Hs.113919 | NM_199342 | LOC374969 | 1 | up | | | | | | Hypothetical protein LOC374969 |
| Hs.188746 | NM_199355 | ADAMTS18 | 16 | | up | | | | | A disintegrin-like and metalloprotease (reprolysin type) |

| Annotation | | | Direction of Change in SZ relative to Controls | | | | | | Name |
|---|---|---|---|---|---|---|---|---|---|
| UniGene ID | Acc | Symbol | Chr. | AnCg | CB | DLPFC | Nacc | PC | STG | |
| Hs.459362 | NM_199414 | PRC1 | 15 | | down | | | | | with thrombospondin type 1 motif, 18 |
| Hs.351851 | NM_199461 | NANOS1 | 10 | | | | | | up | Protein regulator of cytokinesis 1 |
| Hs.18128 | NM_199513 | C20orf44 | 20 | | | | down | | | Nanos homolog 1 (Drosophila) |
| Hs.16803 | NM_201412 | LUC7L | 16;8;5 | up | | | | | | Chromosome 20 open reading frame 44 |
| Hs.220950 | NM_201559 | FOXO3A | 6 | up | up | up | | | | LUC7-like (S. cerevisiae) |
| Hs.259750 | NM_201998 | SF1 | 11 | up | | | | | | Forkhead box O3A |
| Hs.475848 | NM_202758 | HSRTSBETA | 18 | | | | down | | | Splicing factor 1 |
| Hs.434406 | NM_203282 | ZNF539 | 19 | down | | | | | | RTS beta protein |
| Hs.64004 | NM_203406 | LOC153364 | 5 | | | | | down | | Zinc finger protein 539 |
| Hs.417029 | NM_203415 | DERP6 | 17;11 | | | | | | up | Similar to metallo-beta-lactamase superfamily protein |
| Hs.473838 | NM_203433 | DSCR2 | 21 | | down | | | | | S-phase 2 protein |
| Hs.508266 | NM_203495 | COMMD6 | 13 | up | | up | | | | Down syndrome critical region gene 2 |
| Hs.20013 | NM_207170 | P29 | 1 | | down | | | | | COMM domain containing 6 |
| Hs.369763 | NM_207311 | LOC92558 | 12 | | | down | | | | GCIP-interacting protein p29 |
| Hs.306423 | NM_207357 | LOC339524 | 1 | | | | | | down | Hypothetical protein LOC92558 |
| Hs.203717 | NM_212474 | FN1 | 2 | | | | | | down | Hypothetical protein LOC339524 |
| Hs.153752 | NM_212530 | CDC25B | 20 | up | | | | | | Fibronectin 1 |
| Hs.76122 | R05810 | | 1 | | | | | | down | Cell division cycle 25B |
| | | | | | | | | | | Transcribed locus, moderately similar to NP_055301.1 neuronal thread protein AD7c-NTP [Homo sapiens] |
| Hs.283401 | U22030 | CYP2A7 | 19 | | | | down | | | Cytochrome P450, family 2, subfamily A, polypeptide 7 |
| Hs.292156 | U32331 | DKK3 | 11 | | up | | | | | Dickkopf homolog 3 (Xenopus laevis) |
| Hs.174312 | U69193 | TLR4 | 9 | | down | | | | | Toll-like receptor 4 |
| Hs.209226 | U85992 | BMPER | 7 | | up | | | | | BMP-binding endothelial regulator precursor protein |
| Hs.465529 | XM_028067 | MIDN | 19 | | down | down | | | | Midnolin |
| Hs.534513 | XM_028217 | | 4 | | up | | | | up | Hypothetical LOC90024 |
| Hs.311363 | XM_034594 | | | down | | | | | | Data not found |
| Hs.18564 | XM_035299 | ZSWIM6 | 5 | | | | | | down | Zinc finger, SWIM domain containing 6 |
| Hs.292575 | XM_035863 | | | down | | | | | | Data not found |
| Hs.476164 | XM_038288 | ZCCHC11 | 1 | | | | | down | | Zinc finger, CCHC domain containing 11 |
| Hs.314436 | XM_038999 | | | | | | | down | | Data not found |
| Hs.471504 | XM_041126 | KIAA1486 | 2 | | up | | | | | KIAA1486 protein |
| Hs.225974 | XM_043493 | SV2C | 5 | down | | | | | | Synaptic vesicle glycoprotein 2C |
| Hs.184736 | XM_043653 | BEXL1 | X | | down | | | | | Brain expressed X-linked-like 1 |
| Hs.387336 | XM_045423 | | | | up | | | | | Data not found |

| | Annotation | | | Direction of Change in SZ relative to Controls | | | | | | | |
|---|---|---|---|---|---|---|---|---|---|---|---|
| UniGene ID | Acc | Symbol | Chr. | AnCg | CB | DLPFC | Nacc | PC | STG | Name |
| Hs.472285 | XM_046600 | KIAA1272 | 20 | | | | | down | | KIAA1272 protein |
| Hs.298382 | XM_051197 | KIAA1005 | 16 | | | up | | | | KIAA1005 protein |
| Hs.534526 | XM_057296 | LOC116064 | 3 | down | | | | | | Hypothetical protein LOC116064 |
| Hs.187636 | XM_058513 | LRRK2 | 12 | | | | | down | | Leucine-rich repeat kinase 2 |
| Hs.220594 | XM_059492 | | 3 | | | | | down | | Hypothetical LOC131076 |
| Hs.380923 | XM_085929 | MEIS3 | 19 | up | | | | | | Meis1, myeloid ecotropic viral integration site 1 homolog 3 (mouse) |
| Hs.335413 | XM_086879 | | 22 | | | | | | up | Hypothetical LOC150371 |
| Hs.169863 | XM_087089 | WDR43 | 2 | | | up | up | | | WD repeat domain 43 |
| Hs.180663 | XM_166451 | | | | | | | | | Data not found |
| Hs.423725 | XM_168302 | | | | | | down | | | Data not found |
| Hs.196647 | XM_171054 | KIAA0527 | 3 | | | | | down | | KIAA0527 protein |
| Hs.162902 | XM_173173 | AOF1 | 6 | | | up | | | | Amine oxidase (flavin containing) domain 1 |
| Hs.441783 | XM_290629 | C14orf78 | 14;12 | | | down | | | | Chromosome 14 open reading frame 78 |
| Hs.132497 | XM_290941 | PRNPIP | 1 | up | | | | | | Prion protein interacting protein |
| Hs.165762 | XM_291142 | FCHO2 | 5 | | | | | down | | FCH domain only 2 |
| Hs.29068 | XM_291277 | DKFZp761P0423 | 8 | | | | | down | | Hypothetical protein DKFZp761P0423 |
| Hs.124128 | XM_291326 | KIAA2022 | | | up | | | | | KIAA2022 protein |
| Hs.380081 | XM_370575 | FBXL15 | 10;12 | up | | | | | | F-box and leucine-rich repeat protein 15 |
| Hs.9587 | XM_370878 | KIAA2002 | 15 | | down | | | | | KIAA2002 protein |
| Hs.410889 | XM_371074 | DKFZP564D166 | 17 | | | | up | | | Putative ankyrin-repeat containing protein |
| Hs.445218 | XM_371116 | MYO5B | 18 | | | | | up | | Myosin VB |
| Hs.288164 | XM_371614 | FLJ10707 | 3 | up | | | | | | Hypothetical protein FLJ10707 |
| Hs.136235 | XM_371760 | LOC116068 | 5 | | down | | | | | Hypothetical protein LOC116068 |
| Hs.458358 | XM_371844 | TSPYL1 | 6 | | | | | down | | TSPY-like 1 |
| Hs.136398 | XM_372124 | ZCCHC6 | 9 | up | | | | | | Zinc finger, CCHC domain containing 6 |
| Hs.149940 | XM_372128 | | 9 | | up | | | | | Similar to Osteotesticular phosphatase; protein tyrosine phosphatase receptor type V; protein tyrosine phosphatase receptor type W; protein tyrosine phosphatase, receptor type, V |
| Hs.532698 | XM_373630 | LOC145842 | 15 | | down | | | | | Hypothetical protein LOC145842 |
| Hs.97540 | XM_374002 | | 2 | | up | | | | | Hypothetical gene supported by BC032913; BC048425 |
| Hs.389638 | XM_374317 | | 7 | | down | | | | | Hypothetical gene supported by AL713796 |

| | Annotation | | | Direction of Change in SZ relative to Controls | | | | | | | |
|---|---|---|---|---|---|---|---|---|---|---|---|
| UniGene ID | Acc | Symbol | Chr. | AnCg | CB | DLPFC | Nacc | PC | STG | Name | |
| Hs.447579 | XM_375527 | LOC339290 | 18 | | | | | up | | Hypothetical protein LOC339290 | |
| Hs.408708 | XM_375553 | | | down | | | | down | | Data not found | |
| Hs.35524 | XM_375604 | | | | | down | | | up | Data not found | |
| Hs.172884 | XM_375633 | SLC8A2 | 19 | | | | up | | | Solute carrier family 8 (sodium-calcium exchanger), member 2 | |
| Hs.416553 | XM_375714 | | 1 | | up | | | | | Similar to RIKEN cDNA 1700025K23 | |
| Hs.474836 | XM_376010 | LOC387593 | 22 | | | down | | | | TPTE/TPIP pseudogene | |
| Hs.502948 | XM_376043 | | | up | | | | | | Similar to RIKEN cDNA 2310016E02 | |
| Hs.301283 | XM_376193 | | | | up | | | | | Data not found | |
| Hs.113912 | XM_376350 | RAPGEF2 | 4 | down | | | | | down | Rap guanine nucleotide exchange factor (GEF) 2 | |
| Hs.148956 | XM_376436 | LOC134466 | 5 | | | down | | | | Hypothetical protein LOC134466 | |
| Hs.520638 | XM_376567 | KIAA1856 | 7 | | | | | down | | KIAA1856 protein | |
| Hs.308710 | XM_376680 | KIAA1718 | 7 | up | | | | | | KIAA1718 protein | |
| Hs.23133 | XM_378178 | MGC9913 | 19 | up | up | | | | up | Hypothetical protein MGC9913 | |
| Hs.503862 | XM_378309 | | 11 | | | | | | up | Hypothetical LOC399951 | |
| Hs.434271 | XM_378706 | | 17 | | | | | up | | Hypothetical LOC400621 | |
| Hs.477007 | XM_379203 | LOC348801 | 3 | | up | | | | | Hypothetical protein LOC348801 | |
| Hs.446474 | XM_379250 | | | | up | | | | | Hypothetical gene supported by BC038466; BC062790 | |
| Hs.432656 | XM_379438 | LOC285740 | 6 | up | | | | | | Hypothetical protein LOC285740 | |
| Hs.489988 | XM_379923 | | | | | | | down | | Data not found | |
| Hs.494204 | XM_495929 | DKFZp434 N2030 | 12 | | | up | | | | Hypothetical protein DKFZp434N2030 | |
| Hs.17250 | XM_495935 | MGC4767 | 12 | up | up | up | | | up | Hypothetical protein MGC4767 | |
| Hs.435761 | XM_496395 | FLJ34433 | 1 | | down | | | | | Hypothetical protein FLJ34433 | |
| Hs.143840 | XM_496525 | | | | | | down | | | Data not found | |
| Hs.99488 | XM_496588 | LOC130355 | 2 | up | | | | | | Hypothetical protein LOC130355 | |
| Hs.428360 | XM_496681 | KIAA1982 | 4 | up | | down | | | | KIAA1982 protein | |
| Hs.148988 | XM_496999 | KIAA1688 | 8 | | | up | | | | KIAA1688 protein | |
| Hs.112622 | XM_497679 | | 1 | | | | | | | Similar to Laminin receptor 1 | |
| Hs.528187 | XM_498917 | | 2 | | | | | down | | Hypothetical gene supported by AK096649 | |
| Hs.329512 | XM_498955 | | 3 | up | up | | | | | Hypothetical gene supported by BC034933; BC068085 | |
| Hs.171132 | XM_499008 | | 5 | | | down | | | | Hypothetical gene supported by AK124699 | |
| Hs.31917 | XM_499048 | C6orf176 | 6 | | down | | | | | Chromosome 6 open reading frame 176 | |
| Hs.308222 | XM_499514 | LOC401321 | 7 | down | | | | | | Hypothetical LOC401321 | |
| Hs.21925 | Z39995 | | 8 | down | | down | | | | Transcribed locus | |

| Annotation | | | Direction of Change in SZ relative to Controls | | | | | | |
|---|---|---|---|---|---|---|---|---|---|
| UniGene ID | Acc | Symbol | Chr. | AnCg | CB | DLPFC | Nacc | PC | STG | Name |
| Hs.22697 | ZA0025 | | 10 | down | | | | | | Transcribed locus |

GO: 0050874 organismal physiological process

| LocusLink ID | UniGene ID | Symbol |
|---|---|---|
| 10175 | Hs.294603 | CNIH |
| 10560 | Hs.30246 | SLC19A2 |
| 11255 | Hs.251399 | HRH3 |
| 2009 | Hs.12451 | EML1 |
| 28639 | Hs.449451 | TRBC1 |
| 3437 | Hs.47338 | IFIT3 |
| 4690 | Hs.477693 | NCK1 |
| 4929 | Hs.165258 | NR4A2 |
| 501 | Hs.483239 | ALDH7A1 |
| 641 | Hs.169348 | BLM |
| 9308 | Hs.484703 | CD83 |

GO: 0058550 eukaryotic translation initiation factor 2 complex

| LocusLink ID | UniGene ID | Symbol |
|---|---|---|
| 26523 | Hs.22867 | EIF2C1 |
| 83939 | Hs.378808 | eIF2A |
| 8894 | Hs.429180 | EIF2S2 |

GO: 0005739 mitochondrion

| LocusLink ID | UniGene ID | Symbol |
|---|---|---|

| | | |
|---|---|---|
| 10105 | Hs.381072 | PPIF |
| 10730 | Hs.499145 | YME1L1 |
| 126328 | Hs.406062 | NDUFA11 |
| 1891 | Hs.196176 | ECH1 |
| 26292 | Hs.370040 | MYCBP |
| 27429 | Hs.115721 | PRSS25 |
| 285521 | Hs.356697 | FLJ38991 |
| 374291 | Hs.211914 | NDUFS7 |
| 38 | Hs.232375 | ACAT1 |
| 4129 | Hs.46732 | MAOB |
| 4726 | Hs.408257 | NDUFS6 |
| 51103 | Hs.106529 | NDUFAF1 |
| 51373 | Hs.44298 | MRPS17 |
| 51629 | Hs.514216 | CGI-69 |
| 518 | Hs.429 | ATP5G3 |
| 5188 | Hs.119316 | PET112L |
| 53343 | Hs.149500 | NUDT9 |
| 56997 | Hs.118241 | CABC1 |
| 617 | Hs.471401 | BCS1L |
| 6390 | Hs.465924 | SDHB |
| 65993 | Hs.157160 | MRPS34 |
| 7284 | Hs.12084 | TUFM |
| 84134 | Hs.321653 | FLJ12770 |
| 84693 | Hs.94949 | MCEE |
| 84701 | Hs.277101 | COX4I2 |

| GO: 0005622 | intracellular | | |
|---|---|---|---|
| LocusLink ID | UniGene ID | Symbol | Description |
| 50 | Hs.474982 | ACO2 | Aconitase 2, mitochondrial |
| 518 | Hs.429 | ATP5G3 | ATP synthase, H+ transporting, mitochondrial F0 complex, subunit c (subunit 9) isoform 3 |
| 9331 | Hs.464848 | B4GALT6 | UDP-Gal:betaGlcNAc beta 1,4- galactosyltransferase, polypeptide 6 |
| 617 | Hs.471401 | BCS1L | BCS1-like (yeast) |
| 665 | Hs.131226 | BNIP3L | BCL2/adenovirus E1B 19kDa interacting protein 3-like |
| 57128 | Hs.387755 | C6orf149 | Chromosome 6 open reading frame 149 |
| 8697 | Hs.153546 | CDC23 | CDC23 (cell division cycle 23, yeast, homolog) |
| 8941 | Hs.158460 | CDK5R2 | Cyclin-dependent kinase 5, regulatory subunit 2 (p39) |
| 1108 | Hs.162233 | CHD4 | Chromodomain helicase DNA binding protein 4 |
| 51340 | Hs.171342 | CRNKL1 | Crn, crooked neck-like 1 (Drosophila) |
| 1500 | Hs.166011 | CTNND1 | Catenin (cadherin-associated protein), delta 1 |
| 1528 | Hs.465413 | CYB5 | Cytochrome b-5 |
| 1602 | Hs.129452 | DACH1 | Dachshund homolog 1 (Drosophila) |
| 1656 | Hs.408461 | DDX6 | DEAD (Asp-Glu-Ala-Asp) box polypeptide 6 |
| 9162 | Hs.242947 | DGKI | Diacylglycerol kinase, iota |
| 1783 | Hs.369068 | DNCLI2 | Dynein, cytoplasmic, light intermediate polypeptide 2 |
| 54550 | Hs.140950 | EFCBP2 | EF hand calcium binding protein 2 |
| 83939 | Hs.378808 | eIF2A | Eukaryotic translation initiation factor (eIF) 2A |
| 317649 | Hs.476782 | EIF4E3 | Eukaryotic translation initiation factor 4E member 3 |
| 9844 | Hs.304578 | ELMO1 | Engulfment and cell motility 1 (ced-12 homolog, C. elegans) |
| 30001 | Hs.525339 | ERO1L | ERO1-like (S. cerevisiae) |
| 2135 | Hs.357637 | EXTL2 | Exostoses (multiple)-like 2 |
| 23014 | Hs.159699 | FBXO21 | F-box protein 21 |
| 55634 | Hs.444269 | FLJ20344 | Hypothetical protein FLJ20344 |

| GO: 0005622 | intracellular | |
|---|---|---|
| LocusLink ID | UniGene ID | Symbol | Description |
| 29997 | Hs.421907 | GLTSCR2 | Glioma tumor suppressor candidate region gene 2 |
| 56850 | Hs.109929 | GRIPAP1 | GRIP1 associated protein 1 |
| 119391 | Hs.203634 | GSTO2 | Glutathione S-transferase omega 2 |
| 57801 | Hs.154029 | HES4 | Hairy and enhancer of split 4 (Drosophila) |
| 3148 | Hs.434953 | HMGB2 | High-mobility group box 2 |
| 3423 | Hs.303154 | IDS | Iduronate 2-sulfatase (Hunter syndrome) |
| 122953 | Hs.196482 | JDP2 | Jun dimerization protein 2 |
| 10656 | Hs.444558 | KHDRBS3 | KH domain containing, RNA binding, signal transduction associated 3 |
| 57677 | Hs.35524 | KIAA1559 | Mouse zinc finger protein 14-like |
| 3799 | Hs.327736 | KIF5B | Kinesin family member 5B |
| 8609 | Hs.471221 | KLF7 | Kruppel-like factor 7 (ubiquitous) |
| 55915 | Hs.224282 | LANCL2 | LanC lantibiotic synthetase component C-like 2 (bacterial) |
| 51176 | Hs.125132 | LEF1 | Lymphoid enhancer-binding factor 1 |
| 5641 | Hs.18069 | LGMN | Legumain |
| 3998 | Hs.465295 | LMAN1 | Lectin, mannose-binding, 1 |
| 4005 | Hs.34560 | LMO2 | LIM domain only 2 (rhombotin-like 1) |
| 6218 | Hs.294145 | LOC133957 | Similar to RIKEN cDNA 0610011N22 |
| 93349 | Hs.471582 | LOC93349 | Hypothetical protein BC004921 |
| 27258 | Hs.111632 | LSM3 | LSM3 homolog, U6 small nuclear RNA associated (S. cerevisiae) |
| 4129 | Hs.46732 | MAOB | Monoamine oxidase B |
| 51257 | Hs.445113 | MARCH-II | Membrane-associated RING-CH protein II |
| 10445 | Hs.25313 | MCRS1 | Microspherule protein 1 |
| 1072 | Hs.25313 | MCRS1 | Microspherule protein 1 |
| 4205 | Hs.268675 | MEF2A | MADS box transcription enhancer factor 2, polypeptide A (myocyte enhancer factor 2A) |

| GO: 0005622 | intracellular | | |
|---|---|---|---|
| LocusLink ID | UniGene ID | Symbol | Description |
| 28998 | Hs.333823 | MRPL13 | Mitochondrial ribosomal protein L13 |
| 9801 | Hs.44024 | MRPL19 | Mitochondrial ribosomal protein L19 |
| 63931 | Hs.247324 | MRPS14 | Mitochondrial ribosomal protein S14 |
| 4664 | Hs.107474 | NAB1 | NGFI-A binding protein 1 (EGR1 binding protein 1) |
| 126328 | Hs.406062 | NDUFA11 | NADH dehydrogenase (ubiquinone) 1 alpha subcomplex, 11, 14.7kDa |
| 57520 | Hs.314436 | NEDL2 | NEDD4-related E3 ubiquitin ligase NEDL2 |
| 84656 | Hs.387255 | N-PAC | Cytokine-like nuclear factor n-pac |
| 4925 | Hs.128686 | NUCB2 | Nucleobindin 2 |
| 51449 | Hs.278627 | PCYOX1 | Prenylcysteine oxidase 1 |
| 9468 | Hs.132794 | PCYT1B | Phosphate cytidylyltransferase 1, choline, beta isoform |
| 5281 | Hs.468415 | PIGF | Phosphatidylinositol glycan, class F |
| 5311 | Hs.181272 | PKD2 | Polycystic kidney disease 2 (autosomal dominant) |
| 11128 | Hs.436896 | POLR3A | Polymerase (RNA) III (DNA directed) polypeptide A, 155kDa |
| 5464 | Hs.437403 | PP | Pyrophosphatase (inorganic) |
| 25865 | Hs.466987 | PRKD2 | Protein kinase D2 |
| 8559 | Hs.161181 | PRPF18 | PRP18 pre-mRNA processing factor 18 homolog (yeast) |
| 201161 | Hs.433422 | PRR6 | Proline rich 6 |
| 5718 | Hs.4295 | PSMD12 | Proteasome (prosome, macropain) 26S subunit, non-ATPase, 12 |
| 9491 | Hs.471917 | PSMF1 | Proteasome (prosome, macropain) inhibitor subunit 1 (PI31) |
| 10567 | Hs.11417 | RABAC1 | Rab acceptor 1 (prenylated) |
| 5994 | Hs.24422 | RFXAP | Regulatory factor X-associated protein |
| 51320 | Hs.465144 | RKHD2 | Ring finger and KH domain containing 2 |
| 57484 | Hs.480825 | RNF150 | Ring finger protein 150 |
| 6096 | Hs.494178 | RORB | RAR-related orphan receptor B |
| 6165 | Hs.529631 | RPL35A | Ribosomal protein L35a |
| 25939 | Hs.472630 | SAMHD1 | SAM domain and HD domain 1 |
| 79048 | Hs.59804 | SECISBP2 | SECIS binding protein 2 |

GO: 0005622  intracellular

| LocusLink ID | UniGene ID | Symbol | Description |
|---|---|---|---|
| 23013 | Hs.270499 | SHARP | SMART/HDAC1 associated repressor protein |
| 6732 | Hs.443861 | SRPK1 | SFRS protein kinase 1 |
| 10618 | Hs.14894 | TGOLN2 | Trans-golgi network protein 2 |
| 30000 | Hs.416049 | TNPO2 | Transportin 2 (importin 3, karyopherin beta 2b) |
| 80263 | Hs.301526 | TRIM45 | Tripartite motif-containing 45 |
| 55109 | Hs.213393 | VG5Q | Angiogenic factor VG5Q |
| 51564 | Hs.269577 | VPS16 | Protein tyrosine phosphatase, receptor type, A |
| 64601 | Hs.269577 | VPS16 | Protein tyrosine phosphatase, receptor type, A |
| 8976 | Hs.143728 | WASL | Wiskott-Aldrich syndrome-like |
| 29799 | Hs.517436 | YPEL1 | Yippee-like 1 (Drosophila) |
| 7528 | Hs.388927 | YY1 | YY1 transcription factor |
| 146198 | Hs.461074 | ZFP90 | Zinc finger protein 90 homolog (mouse) |

| UniGene ID | Acc | Gene Symbol | Chromosomal Location | Lymphocyte Direction (Schizophrenia/ Control) | Fold change | p-value | Fold Change Agree Brain/ Lymphocyte | Fold Change Agree Brain/ Lymphocyte | Brain Direction (Schizophrenia/ Control) | Gene Name |
|---|---|---|---|---|---|---|---|---|---|---|
| Hs.232375 | NM_000019 | ACAT1 | 11q22.3-q23.1 | UP | 1.15 | 0.024 | yes | yes | UP | Acetyl-Coenzyme A acetyltransferase 1 (acetoacetyl Coenzyme A thiolase) |
| Hs.130712 | NM_024876 | ADCK4 | 19q13.2 | DOWN | -1.11 | 0.042 | No | No | UP | AarF domain containing kinase 4 |
| Hs.207776 | NM_000027 | AGA | 4q32-q33 | DOWN | -1.11 | 0.038 | yes | yes | DOWN | Aspartylglucosaminidase |
| Hs.368486 | NM_001649 | APXL | Xp22.3 | DOWN | -1.14 | 0.024 | No | No | UP | Apical protein-like (Xenopus laevis) |
| Hs.126137 | NM_181866 | BACH | 1p36.31-p36.11 | DOWN | -1.11 | 0.049 | No | No | UP | Brain acyl-CoA hydrolase |
| Hs.293753 | NM_032515 | BOK | 2q37.3 | DOWN | -1.12 | 0.020 | No | No | UP | BCL2-related ovarian killer |
| Hs.288981 | NM_025152 | C14orf127 | 14q12 | DOWN | -1.16 | 0.019 | No | No | UP | Chromosome 14 open reading frame 127 |
| Hs.443789 | NM_024581 | C6orf60 | 6q22.31 | UP | 1.46 | 0.018 | No | No | DOWN | Chromosome 6 open reading frame 60 |
| Hs.532296 | NM_017998 | C9orf40 | 9q21.31 | UP | 1.13 | 0.036 | yes | yes | UP | Chromosome 9 open reading frame 40 |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.297343 | NM_172226 | CAMKK2 | 12q24.2 | DOWN | -1.15 | 0.030 | No | No | UP | Calcium/calmodulin -dependent protein kinase 2, beta |
| Hs.297343 | NM_172226 | CAMKK2 | 12q24.2 | DOWN | -1.13 | 0.018 | No | No | UP | Calcium/calmodulin -dependent protein kinase 2, beta |
| Hs.474797 | NM_007061 | CDC42EP1 | 22q13.1 | DOWN | -1.10 | 0.008 | No | No | UP | CDC42 effector protein (Rho GTPase binding) 1 |
| Hs.249129 | NM_001279 | CIDEA | 18p11.21 | DOWN | -1.16 | 0.016 | No | No | UP | Cell death-inducing DFFA-like effector a |
| Hs.29549 | NM_016511 | CLEC1 | 12p13.31 | DOWN | -1.14 | 0.025 | yes | yes | DOWN | C-type lectin-like receptor-1 |
| Hs.270437 | NM_031361 | COL4A3BP | 5q13.3 | UP | 1.27 | 0.047 | yes | yes | UP | Collagen, type IV, alpha 3 (Goodpasture antigen) binding protein |
| Hs.464422 | NM_130386 | COLEC12 | 18pter-p11.3 | DOWN | -1.15 | 0.044 | yes | yes | DOWN | Collectin sub-family member 12 |
| Hs.330384 | NM_014325 | CORO1C | 12q24.1 | DOWN | -1.17 | 0.040 | No | No | UP | Coronin, actin binding protein, 1C |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.45127 | NM_006574 | CSPG5 | 3p21.3 | UP | 1.16 | 0.023 | No | No | DOWN | Chondroitin sulfate proteoglycan 5 (neuroglycan C) |
| Hs.304682 | NM_000099 | CST3 | 20p11.21 | UP | 1.74 | 0.026 | No | No | DOWN | Cystatin C (amyloid angiopathy and cerebral hemorrhage) |
| Hs.26704 | NM_014608 | CYFIP1 | 15q11 | DOWN | -1.42 | 0.010 | yes | yes | DOWN | Cytoplasmic FMR1 interacting protein 1 |
| Hs.283401 | U22030 | CYP2A7 | 19q13.2 | DOWN | -1.13 | 0.006 | yes | yes | DOWN | Cytochrome P450, family 2, subfamily A, polypeptide 7 |
| Hs.12451 | AF035276 | EML1 | 14q32 | DOWN | -1.11 | 0.047 | No | No | UP | Echinoderm microtubule associated protein like 1 |
| Hs.104925 | NM_003633 | ENC1 | 5q12-q13.3 | UP | 1.45 | 0.046 | yes | yes | UP | Ectodermal-neural cortex (with BTB-like domain) |
| Hs.104925 | NM_003633 | ENC1 | 5q12-q13.3 | UP | 1.42 | 0.033 | yes | yes | UP | Ectodermal-neural cortex (with BTB-like domain) |
| Hs.306251 | NM_001982 | ERBB3 | 12q13 | DOWN | -1.45 | 0.015 | yes | yes | DOWN | V-erb-b2 erythroblastic leukemia viral oncogene homolog 3 (avian) |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.438695 | AK094876 | FKBP11 | 12q13.12 | UP | 1.34 | 0.041 | No | No | DOWN | FK506 binding protein 11, 19 kDa |
| Hs.443529 | NM_019607 | FLJ11267 | 8q13.1 | DOWN | -1.13 | 0.040 | yes | yes | DOWN | Hypothetical protein FLJ11267 |
| Hs.147836 | NM_017768 | FLJ20331 | 1p31.2 | UP | 1.38 | 0.034 | No | No | DOWN | Hypothetical protein FLJ20331 |
| Hs.413137 | NM_001680 | FXYD2 | 11q23 | DOWN | -1.19 | 0.023 | No | No | UP | FXYD domain containing ion transport regulator 2 |
| Hs.473648 | NM_000819 | GART | 21q22.1 | UP | 1.32 | 0.029 | yes | yes | UP | Phosphoribosylglycinamide formyltransferase, phosphoribosylglycinamide synthetase, phosphoribosylaminoimidazole synthetase |
| Hs.522418 | NM_001003722 | GLE1L | 9q34.13 | UP | 1.28 | 0.045 | yes | yes | UP | GLE1 RNA export mediator-like (yeast) |
| Hs.522418 | NM_001003722 | GLE1L | 9q34.13 | DOWN | -1.12 | 0.015 | No | No | UP | GLE1 RNA export mediator-like (yeast) |
| Hs.430425 | NM_002074 | GNB1 | 1p36.33 | DOWN | -1.20 | 0.034 | No | No | UP | Guanine nucleotide binding protein (G protein), beta polypeptide 1 |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.155090 | AL117471 | GNB5 | 15q21.1 | DOWN | -1.13 | 0.030 | No | No | UP | Guanine nucleotide binding protein (G protein), beta 5 |
| Hs.155090 | NM_006578 | GNB5 | 15q21.1 | DOWN | -1.10 | 0.005 | No | No | UP | Guanine nucleotide binding protein (G protein), beta 5 |
| Hs.198612 | NM_005458 | GPR51 | 9q22.1-q22.3 | UP | 1.17 | 0.044 | yes | yes | UP | G protein-coupled receptor 51 |
| Hs.445066 | AI499801 | GRIN2B | 12p12 | DOWN | -1.16 | 0.034 | yes | yes | DOWN | Glutamate receptor, ionotropic, N-methyl D-aspartate 2B |
| Hs.12126 | NM_018487 | HCA112 | 7q36.1 | DOWN | -1.34 | 0.007 | yes | yes | DOWN | Hepatocellular carcinoma-associated antigen 112 |
| Hs.278635 | NM_016648 | HDCMA18P | 4q26 | DOWN | -1.40 | 0.046 | yes | yes | DOWN | HDCMA18P protein |
| Hs.35804 | D25215 | HERC3 | 4q21 | DOWN | -1.13 | 0.012 | No | No | UP | Hect domain and RLD 3 |
| Hs.380250 | AK094968 | IFI16 | 1q22 | UP | 1.19 | 0.038 | No | No | DOWN | Interferon, gamma-inducible protein 16 |
| Hs.430551 | NM_003870 | IQGAP1 | 15q26.1 | UP | 1.24 | 0.021 | No | No | DOWN | IQ motif containing GTPase activating protein 1 |
| Hs.6396 | NM_006694 | JTB | 1q21 | UP | 1.53 | 0.048 | yes | yes | UP | Jumping translocation breakpoint |
| Hs.21703 | NM_012281 | KCND2 | 7q31 | UP | 1.97 | 0.038 | yes | yes | UP | Potassium voltage-gated channel, Shal-related subfamily, member 2 |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.408960 | NM_002241 | KCNJ10 | 1q22-q23 | DOWN | -1.14 | 0.005 | yes | yes | DOWN | Potassium inwardly-rectifying channel, subfamily J, member 10 |
| Hs.32505 | NM_004981 | KCNJ4 | 22q13.1 | DOWN | -1.10 | 0.028 | yes | yes | DOWN | Potassium inwardly-rectifying channel, subfamily J, member 4 |
| Hs.2785 | NM_000422 | KRT17 | 17q12-q21 | DOWN | -1.15 | 0.035 | yes | yes | DOWN | Keratin 17 |
| Hs.23748 | NM_001290 | LDB2 | 4p16 | DOWN | -1.20 | 0.011 | No | No | UP | LIM domain binding 2 |
| Hs.352614 | AF007155 | LOC254531 | 15q13.2 | UP | 1.95 | 0.036 | No | No | DOWN | PLSC domain containing protein |
| Hs.47649 | NM_020166 | MCCC1 | 3q27 | DOWN | -1.16 | 0.022 | yes | yes | DOWN | Methylcrotonoyl-Coenzyme A carboxylase 1 (alpha) |
| Hs.535659 | BC002458 | MCM3AP | 21q22.3 | DOWN | -1.16 | 0.046 | No | No | UP | MCM3 minichromosome maintenance deficient 3 (S. cerevisiae) associated protein |
| Hs.460217 | NM_153208 | MGC35048 | 16p13.11 | DOWN | -1.18 | 0.013 | yes | yes | DOWN | Hypothetical protein MGC35048 |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.21213 | NM_000259 | MYO5A | 15q21 | DOWN | -1.14 | 0.027 | No | No | UP | Myosin VA (heavy polypeptide 12, myoxin) |
| Hs.472185 | NM_004552 | NDUFS5 | 1p34.2-p33 | UP | 1.21 | 0.035 | yes | yes | UP | NADH dehydrogenase (ubiquinone) Fe-S protein 5, 15kDa (NADH-coenzyme Q reductase) |
| Hs.211914 | NM_024407 | NDUFS7 | 19p13.3 | DOWN | -1.11 | 0.039 | No | No | UP | NADH dehydrogenase (ubiquinone) Fe-S protein 7, 20kDa (NADH-coenzyme Q reductase) |
| Hs.459255 | AI935701 | NTRK3 | 15q25 | DOWN | -1.14 | 0.040 | No | No | UP | Neurotrophic tyrosine kinase, receptor, type 3 |
| Hs.459255 | AI935701 | NTRK3 | 15q25 | DOWN | -1.12 | 0.021 | No | No | UP | Neurotrophic tyrosine kinase, receptor, type 3 |
| Hs.435714 | NM_002576 | PAK1 | 11q13-q14 | UP | 1.23 | 0.030 | yes | yes | UP | P21/Cdc42/Rac1-activated kinase 1 (STE20 homolog, yeast) |
| Hs.503584 | AI638679 | PANX1 | 11q21 | UP | 1.27 | 0.036 | yes | yes | UP | Pannexin 1 |
| Hs.278627 | NM_016297 | PCYOX1 | 2p13.3 | UP | 1.14 | 0.033 | yes | yes | UP | Prenylcysteine oxidase 1 |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.481819 | AK021922 | PDZK3 | 5p13.3 | UP | 1.24 | 0.009 | No | No | DOWN | PDZ domain containing 3 |
| Hs.468415 | NM_002643 | PIGF | 2p21-p16 | DOWN | -1.12 | 0.020 | No | No | UP | Phosphatidylinositol glycan, class F |
| Hs.466848 | NM_006905 | PSG1 | 19q13.2 | DOWN | -1.11 | 0.036 | No | No | UP | Pregnancy specific beta-1-glycoprotein 1 |
| Hs.413801 | NM_014614 | PSME4 | 2p16.3 | DOWN | -3.66 | 0.003 | No | No | UP | Proteasome (prosome, macropain) activator subunit 4 |
| Hs.446429 | NM_000954 | PTGDS | 9q34.2-q34.3 | DOWN | -2.93 | 0.016 | yes | yes | DOWN | Prostaglandin D2 synthase 21kDa (brain) |
| Hs.114062 | NM_014241 | PTPLA | 10p14-p13 | DOWN | -1.12 | 0.034 | No | No | UP | Protein tyrosine phosphatase-like (proline instead of catalytic arginine), member a |
| Hs.434375 | BI820698 | PTPRB | 12q15-q21 | UP | 1.32 | 0.019 | No | No | DOWN | Protein tyrosine phosphatase, receptor type, B |
| Hs.296169 | NM_004578 | RAB4A | 1q42-q43 | UP | 1.13 | 0.031 | yes | yes | UP | RAB4A, member RAS oncogene family |
| Hs.411488 | NM_138290 | RPIB9 | 7q21.13 | DOWN | -1.16 | 0.001 | No | No | UP | Rap2-binding protein 9 |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizophrenia/Control) | Gene Name |
|---|---|---|---|---|---|---|---|---|---|---|
| Hs.374588 | NM_000985 | RPL17 | 18q21 | DOWN | -1.17 | 0.012 | No | No | UP | Ribosomal protein L17 |
| Hs.374588 | NM_000985 | RPL17 | 18q21 | DOWN | -1.13 | 0.026 | No | No | UP | Ribosomal protein L17 |
| Hs.465924 | NM_003000 | SDHB | 1p36.1-p35 | DOWN | -1.12 | 0.038 | No | No | UP | Succinate dehydrogenase complex, subunit B, iron sulfur (Ip) |
| Hs.146804 | NM_006717 | SPIN | 9q22.1-q22.3 | DOWN | -1.32 | 0.039 | No | No | UP | Spindlin |
| Hs.237825 | NM_006947 | SRP72 | 4q11 | DOWN | -1.13 | 0.044 | No | No | UP | Signal recognition particle 72kDa |
| Hs.102735 | NM_012446 | SSBP2 | 5q14.1 | UP | 1.22 | 0.050 | No | No | DOWN | Single-stranded DNA binding protein 2 |
| Hs.12409 | NM_001048 | SST | 3q28 | DOWN | -1.15 | 0.045 | yes | yes | DOWN | Somatostatin |
| Hs.482390 | NM_003243 | TGFBR3 | 1p33-p32 | UP | 1.18 | 0.017 | No | No | DOWN | Transforming growth factor, beta receptor III (betaglycan, 300kDa) |
| Hs.14894 | NM_006464 | TGOLN2 | 2p11.2 | UP | 1.15 | 0.016 | yes | yes | UP | Trans-golgi network protein 2 |
| Hs.465784 | AF026030 | TIMM44 | 19p13.3-p13.2 | DOWN | -1.15 | 0.033 | No | No | UP | Translocase of inner mitochondrial membrane 44 homolog (yeast) |
| Hs.465784 | NM_006351 | TIMM44 | 19p13.3-p13.2 | DOWN | -1.15 | 0.033 | No | No | UP | Translocase of inner mitochondrial membrane 44 homolog (yeast) |

| UniGene ID | Acc | Gene Symbol | Chromosomal Location | Lymphocyte Direction (Schizophrenia/Control) | Fold change | p-value | Fold Change Agree Brain/Lymphocyte | Fold Change Agree Brain/Lymphocyte | Brain Direction (Schizo-phrenia/Control) | Gene Name |
|---|---|---|---|---|---|---|---|---|---|---|
| Hs.287362 | AB046767 | TLE3 | 15q22 | DOWN | -1.19 | 0.009 | No | No | UP | Transducin-like enhancer of split 3 (E(sp1) homolog, Drosophila) |
| Hs.287362 | NM_005078 | TLE3 | 15q22 | DOWN | -1.19 | 0.009 | No | No | UP | Transducin-like enhancer of split 3 (E(sp1) homolog, Drosophila) |
| Hs.499145 | BC019602 | YME1L1 | 10p14 | UP | 1.13 | 0.043 | No | No | DOWN | YME1-like 1 (S. cerevisiae) |
| Hs.172979 | NM_003451 | ZNF177 | 19p13.2 | DOWN | -1.17 | 0.021 | No | No | UP | Zinc finger protein 177 |

| Accession Number | Gene Symbol | Microarray Fold Change | Q-PCR Fold Change | Microarray (p-value t-test) | Q-PCR (p-value t-test) | Cytogenetic Band | Gene Name |
|---|---|---|---|---|---|---|---|
| NM_002110 | HCK | 2.58 | 4.71 | 0.030 | 0.02 | 20q11-q12 | hemopoietic cell kinase |
| NM_021005 | NR2F2 | 1.74 | 4.15 | 0.047 | 0.02 | 15q26.2 | nuclear receptor subfamily 2, group F, member 2 |
| NM_017423 | GALNT7 | 1.34 | 2.81 | 0.041 | 0.46 | 4q34.1 | UDP-N-acetyl-alpha-D-galactosamine:polypeptide N-acetylgalactosaminyltransferase 7 (GalNAc-T7) |
| NM_139045 | SMARCA2 | 1.75 | 2.27 | 0.028 | 0.03 | 9p22.3 | SWI/SNF related, matrix associated, actin dependent regulator of chromatin, subfamily a, member 2 |
| NM_018639 | WSB2 | 1.49 | 2.18 | 0.003 | 0.02 | 12q24.23 | WD repeat and SOCS box containing protein 2 |
| NM_203504 | G3BP2 | 1.28 | 2.04 | 0.045 | 0.07 | 4q21.21 | Ras-GTPase activating protein SH3 domain-binding protein 2 |
| NM_023927 | NS3TP2 | 1.27 | 1.75 | 0.030 | 0.08 | 5q23.3 | HCV NS3-transactivated protein 2 |
| NM_003816 | ADAM9 | 1.45 | 1.70 | 0.024 | 0.04 | 8p11.22 | a disintegrin and metalloproteinase domain 9 (meltrin gamma) |
| BQ000126 | TMOD3 | 1.21 | 1.39 | 0.031 | 0.12 | 15q21.1-q21.2 | tropomodulin 3 (ubiquitous) |
| NM_003100 | SNX2 | 1.43 | 0.95 | 0.042 | 0.45 | 5q23 | sorting nexin 2 |
| AL041379 | HERC3 | 0.89 | 0.90 | 0.023 | 0.34 | 4q21 | hect domain and RLD 3 |
| AA487462 | FLJ20637 | 0.81 | 0.68 | 0.014 | 0.08 | 4q22.1 | hect domain and RLD 6 |
| BM855607 | IGJ | 0.45 | 0.63 | 0.038 | 0.21 | 4q21 | immunoglobulin J polypeptide, linker protein for immunoglobulin alpha and mu polypeptides |
| NM_005214 | CTLA4 | 0.82 | 0.14 | 0.036 | 0.04 | 2q33 | cytotoxic T-lymphocyte-associated protein 4 |
| AV700777 | ADH1B | 0.89 | 0.10 | 0.023 | 0.02 | 4q21-q23 | alcohol dehydrogenase IB (class I), beta polypeptide |

FIG. 5

| db SNP RS ID | NCBI (Mb) | Cis < 5 | Regression (p-value) |
|---|---|---|---|
| rs1318822 | 170460379 | 8.6 | 0.0015 |
| rs1403225 | 171867785 | 7.2 | 0.0158 |
| rs1812424 | 173851484 | 5.2 | 0.0158 |
| rs2119788 | 175143279 | 3.9 | 0.0020 |
| rs723820 | 177930796 | 1.1 | 0.0020 |
| rs723819 | 177930836 | 1.1 | 0.0020 |
| rs1112286 | 178134007 | 0.9 | 0.0037 |
| rs1375749 | 178157255 | 0.9 | 0.0037 |
| rs1902018 | 179382986 | 0.3 | 0.0016 |
| rs722387 | 179808887 | 0.8 | 0.0400 |
| rs1112857 | 181655677 | 2.6 | 0.0400 |

FIG. 6

Genes dysregulated in MD, BP, and schizophrenia

| | UniGene ID | probe set | Acc | Name | Symbol | Direction of Change |
|---|---|---|---|---|---|---|
| 1 | | | | | | |
| 2 | Hs.282878 | Hs.282878_at | NM_021633 | Kelch-like 12 (Drosophila) | KLHL12 | DLPFC-BPD&MDD&SCZ-U |
| 3 | Hs.435039 | Hs.435039_at | NM_014914 | Trinucleotide repeat containing 17 | CENTG2 | DLPFC-BPD&MDD&SCZ-U |
| 4 | Hs.530712 | Hs.530712_at | NM_017917 | Chromosome 14 open reading frame 10 | C14orf10 | DLPFC-BPD&MDD&SCZ-U |
| 5 | Hs.56294 | Hs.56294_at | NM_004794 | RAB33A, member RAS oncogene family | RAB33A | DLPFC-BPD&MDD&SCZ-U |
| 6 | Hs.21577 | Hs.21577_at | NM_005701 | RNA, U transporter 1 | RNUT1 | DLPFC-BPD&SCZ-U |
| 7 | Hs.274479 | Hs.274479_at | NM_197972 | Non-metastatic cells 7, protein expressed in (nucleoside-diphosphate kinase) | NME7 | DLPFC-BPD&SCZ-U |
| 8 | Hs.368486 | Hs.368486_at | NM_001649 | Apical protein-like (Xenopus laevis) | APXL | DLPFC-BPD&SCZ-U |
| 9 | Hs.468415 | Hs.468415_at | NM_002643 | Phosphatidylinositol glycan, class F | PIGF | DLPFC-BPD&SCZ-U |
| 10 | Hs.471401 | Hs.471401_at | NM_004328 | BCS1-like (yeast) | BCS1L | DLPFC-BPD&SCZ-U |
| 11 | Hs.502145 | Hs.502145_at | NM_006157 | NEL-like 1 (chicken) | NELL1 | DLPFC-BPD&SCZ-U |
| 12 | Hs.514036 | Hs.514036_at | NM_006923 | Stromal cell-derived factor 2 | SDF2 | DLPFC-BPD&SCZ-U |
| 13 | Hs.532853 | Hs.532853+_at | NM_004146 | NADH dehydrogenase (ubiquinone) 1 beta subcomplex, 7, 18kDa | NDUFB7 | DLPFC-BPD&SCZ-U |
| 14 | Hs.111779 | Hs.111779_at | NM_003118 | Secreted protein, acidic, cysteine-rich (osteonectin) | SPARC | DLPFC-BPD&MDD&SCZ-D |
| 15 | Hs.171695 | Hs.171695_at | NM_004417 | Dual specificity phosphatase 1 | DUSP1 | DLPFC-BPD&MDD&SCZ-D |

| 16 | Hs.212838 | Hs.212838-_at | NM_000014 | Alpha-2-macroglobulin | A2M | DLPFC-BPD&MDD&SCZ-D |
| --- | --- | --- | --- | --- | --- | --- |
| 17 | Hs.34560 | Hs.34560-_at | NM_005574 | LIM domain only 2 (rhombotin-like 1) | LMO2 | DLPFC-BPD&MDD&SCZ-D |
| 18 | Hs.347270 | Hs.347270-_at | NM_033554 | Major histocompatibility complex, class II, DP alpha 1 | HLA-DPA1 | DLPFC-BPD&MDD&SCZ-D |
| 19 | Hs.436568 | Hs.436568_at | BC024272 | CD74 antigen (invariant polypeptide of major histocompatibility complex, class II antigen-associated) | CD74 | DLPFC-BPD&MDD&SCZ-D |
| 20 | Hs.491582 | Hs.491582_at | NM_000931 | Plasminogen activator, tissue | PLAT | DLPFC-BPD&MDD&SCZ-D |
| 21 | Hs.534115 | Hs.534115_at | NM_006988 | A disintegrin-like and metalloprotease (reprolysin type) with thrombospondin type 1 motif, 1 | ADAMTS1 | DLPFC-BPD&MDD&SCZ-D |
| 22 | Hs.17109 | Hs.17109_at | NM_004867 | Integral membrane protein 2A | ITM2A | DLPFC-BPD&SCZ-D |
| 23 | Hs.485130 | Hs.485130_at | K01615 | Major histocompatibility complex, class II, DP beta 1 | HLA-DPB1 | DLPFC-BPD&SCZ-D |
| 24 | Hs.504877 | Hs.504877_at | X69549 | Rho GDP dissociation inhibitor (GDI) beta | ARHGDIB | DLPFC-BPD&SCZ-D |
| 25 | Hs.520048 | Hs.520048_at | NM_019111 | Major histocompatibility complex, class II, DR alpha | HLA-DRA | DLPFC-BPD&SCZ-D |

Genes dysregulated in MD, BP, and schizophrenia

| Symbol | Name | UniGene ID | AnCg | DLPFC | CB | nAcc |
|---|---|---|---|---|---|---|
| PTGDS | Prostaglandin | Hs.446429 | | | CB-D | nAcc-D |
| PLAT | Plasminogen activator, tissue | Hs. 491582 | AnCg-D | DLPFC-D | | |
| ADAMTS1 | Disintegrin-like and metalloprotease | Hs. 534115 | | DLPFC-D | | nAcc-D |

FIG. 8

Genes Dysregulated in both SZ and BPD DLPFC

| NAME | SYMBOL | NAME | SYMBOL |
|---|---|---|---|
| Kelch-like 12 (Drosophila) | KLHL12 | LIM domain only 2 (rhombotin-like 1) | LMO2 |
| Trinucleotide repeat containing 17 | CENTG2 | | |
| Chromosome 14 open reading frame 10 | C14orf10 | Major histocompatibility complex, class II, DP alpha 1 | HLA-DPA1 |
| RAB33A, member RAS oncogene family | RAB33A | | |
| RNA, U transporter 1 | RNUT1 | CD74 antigen (invariant polypeptide of major histocompatibility complex, class II antigen-associated) | CD74 |
| Non-metastatic cells 7, protein expressed in (nucleoside-diphosphate kinase) | NME7 | Plasminogen activator, tissue | PLAT |
| Apical protein-like (Xenopus laevis) | APXL | | |
| Phosphatidylinositol glycan, class F | PIGF | A disintegrin-like and metalloprotease (reprolysin type) with thrombospondin type 1 motif, 1 | ADAMTS1 |
| BCS1-like (yeast) | BCS1L | | |
| NEL-like 1 (chicken) | NELL1 | Integral membrane protein 2A | ITM2A |
| Stromal cell-derived factor 2 | SDF2 | Major histocompatibility complex, class II, DP beta 1 | HLA-DPB1 |
| NADH dehydrogenase (ubiquinone) 1 beta subcomplex, 7, 18kDa | NDUFB7 | Rho GDP dissociation inhibitor (GDI) beta | ARHGDIB |
| Secreted protein, acidic, cysteine-rich (osteonectin) | SPARC | Major histocompatibility complex, class II, DR alpha | HLA-DRA |
| Dual specificity phosphatase 1 | DUSP1 | | |
| Alpha-2-macroglobulin | A2M | Major histocompatibility complex, class II, DR alpha | HLA-DRA |

FIG. 13

LI_UP_DOWN_candidates_AND_BPD_26 JAN 06

???
AMY
NM_002781  19q13.2         PSG5       Pregnancy specific beta-1-glycoprotein 5
NM_003998  4q24                       Nuclear factor of kappa light polypeptide gene enhance
NM_004898  4q12            CLOCK      Clock homolog (mouse)
NM_013263  16q12           BRD7       Bromodomain containing 7
AnCg
NM_001048  3q28            SST        Somatostatin
NM_002093  3q13.3                     Glycogen synthase kinase 3 beta
NM_003489  21q11.2         NRIP1      Nuclear receptor interacting protein 1

NM_003936  2q35            CDK5R2     Cyclin-dependent kinase 5, regulatory subunit 2 (p39)
NM_013444  Xp11.23-p11.1   UBQLN2     Ubiquilin 2
NM_017993  13q14.11        FLJ10094   Hypothetical protein FLJ10094
NM_020178  17q21           CA10       Carbonic anhydrase X
NM_021952  1p34            ELAVL4     ELAV (embryonic lethal, abnormal vision, Drosophila)-like 4 (Hu antigen D)

DLPFC

| NM_025098 | 11q13.5 | MOGAT2 | Monoacylglycerol O-acyltransferase 2 |

HC
None

UP
AMY

|  |  |  |  |
|---|---|---|---|
| NM_002065 | 1q31 | GLUL | Glutamate-ammonia ligase (glutamine synthetase) (not in BPD) |
| NM_000014 | 12p13.3-p12.3 | A2M | Alpha-2-macroglobulin |
| NM_001004 | 11p15.5-p15.4 | RPLP2 | Ribosomal protein, large, P2 |
| NM_001283 | 7q22.1 | AP1S1 | Adaptor-related protein complex 1, sigma 1 subunit |
| NM_004355 | 5q32 | CD74 | CD74 antigen (invariant polypeptide of major histocompatibility complex, class II antigen-associated) |
| NM_004368 | 21q11.1 | CNN2 | Calponin 2 |
| NM_005617 | 5q31-q33 | RPS14 | Ribosomal protein S14 |
| NM_006119 | 10q24 | ??? | Fibroblast growth factor 8 (androgen-induced) |
| NM_006870 | 20p12.1 | DSTN | Destrin (actin depolymerizing factor) |
| NM_080391 | 1p35 | PIP4A2 | Protein tyrosine phosphatase type IVA, member 2 |
| NM_153477 | Xp11.23-p11.22 | UXT | Ubiquitously-expressed transcript |

AnCg
None

DLPFC2

|  |  |  |  |
|---|---|---|---|
| NM_000014 | 12p13.3-p12.3 | A2M | Alpha-2-macroglobulin |
| NM_001004 | 11p15.5-p15.4 | RPLP2 | Ribosomal protein, large, P2 |
| NM_001013 | 19q13.4 | RPS9 | Ribosomal protein S9 |
| NM_001283 | 7q22.1 | AP1S1 | Adaptor-related protein complex 1, sigma 1 subunit |
| NM_002178 | 12q13 | IGFBP6 | Insulin-like growth factor binding protein 6 |
| NM_019597 | Xq22 | HNRPH2 | Heterogeneous nuclear ribonucleoprotein H2 (H') |
| NM_018584 | 1p36.12 | CaMKINalpha | Calcium/calmodulin-dependent protein kinase II inhibitor 1 (not in BPD) |

HC

|  |  |  |  |
|---|---|---|---|
| NM_053025 | 3q21 | MYLK | Myosin, light polypeptide kinase |
| NM_006693 | 2q24 | ?? | T-box, brain, 1 (not in BPD) |

COMPOSITIONS AND METHODS FOR DIAGNOSING AND TREATING NEUROPSYCHIATRIC DISORDERS

CROSS-REFERENCES TO RELATED APPLICATIONS

The present application claims priority to U.S. Ser. No. 60/667,299, filed Mar. 31, 2005, and U.S. Ser. No. 60/776,103, filed Feb. 22, 2006, herein incorporated by reference in their entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Psychotic disorders such as schizophrenia and mood disorders such as major depression and bipolar disorder are a major public health problem, affecting a significant portion of the adult population of the United States each year. While it has been hypothesized that mental disorders, including psychotic disorders such as schizophrenia as well as mood disorders such as major depression and bipolar disorder have genetic roots, little progress has been made in identifying gene sequences and gene products that play a role in causing these disorders, as is true for many diseases with a complex genetic origin (see, e.g., Burmeister, *Biol. Psychiatry* 45:522-532 (1999)). Relying on the discovery that certain genes expressed in particular brain pathways and regions are likely involved in the development of mental disorders, the present invention provides methods for diagnosis and treatment of mental disorders such as schizophrenia, as well as methods for identifying compounds effective in treating mental disorders.

BRIEF SUMMARY OF THE INVENTION

In order to further understand the neurobiology of psychotic disorders such as schizophrenia, the inventors of the present application have used DNA microarrays to study expression profiles of human post-mortem brains from patients diagnosed with schizophrenia. The work has focused on six brain regions that are pathways or circuits involved in schizophrenia: the anterior cingulate cortex (AnCg), dorsolateral prefrontal cortex (DLPFC), cerebellar cortex (CB), superior temporal gyms (STG), parietal cortex (PC), and nucleus accumbens (nAcc).

The present invention demonstrates differential expression of genes in selected regions of brains of patients suffering from schizophrenia in comparison with normal control subjects. These genes include the transcripts listed in FIG. 1; the genes listed in FIG. 2 which are differentially expressed in the AnCg using Affymetrix chips and using brains with no agonal factors; the genes listed in FIG. 3 which are differentially expressed in the DLPFC using Affymetrix chips and using brains with no agonal factors; and the genes listed in FIG. 4 which are significantly dysregulated in both lymphoblastic and brain tissues.

In addition, the present invention identifies genes which are not differentially regulated in brain tissue but which are differentially regulated in lymphocytes of schizophrenic patients (FIG. 5). Also provided is a list (FIG. 6) of single nucleotide polymorphic markers which are related to aspartylglucosaminuria (AGA), a gene which is dysregulated in both brain and lymphocytes of schizophrenic patients. FIGS. 7 and 8 show genes that are dysregulated in schizophrenia, major depression, and bipolar disorder.

The present invention also provides genes that are differentially expressed in the amygdala in patients diagnosed with major depression disorder, bipolar disorder, and/or schizophrenia (FIGS. 9-13).

The present invention also provides lithium responsive genes that are differentially expressed in the amygdale of lithium treated bipolar subjects and lithium treated non-human primates (FIG. 14).

The present invention also provides validation of a variant version of PSPHL with an insertion deletion mutation as a useful diagnostic tool to distinguish patients with bipolar disorder among patients presenting with depression, or for diagnosis of bipolar disorder.

Genes that are differentially expressed in neuropsychiatric disorders are useful in diagnosing psychotic and mood disorders, e.g., providing SNPs, biomarkers, diagnostic probe sets for PCR and chip assays, and antigens and antibodies for immunoassays such as ELISA and immunohistochemical assays. Differential expression by brain region similarly is a useful diagnostic and therapeutic tool, as psychotic and mood disorders primarily affect certain brain regions that are part of circuits or pathways involved in the disorder. Imaging brain endogenous gene expression with sequence-specific antisense radiopharmaceuticals and novel aptamer-based probes is a powerful diagnostic tool. Those probes can be detected using both fluorescent- and radio-labels that can be used in conjunction with single-photon emission computed tomography (SPECT) or positron emission tomography (PET) imaging modalities. The identification of genes, proteins, and biochemical assays involved in psychotic and mood disorders also provides the means for drug discovery for anti-psychotic therapeutics, such as small molecules, siRNA, and antibodies.

This invention thus provides methods for determining whether a subject has or is predisposed for a mental disorder. The invention also provides methods of providing a prognosis and for monitoring disease progression and treatment. Furthermore, the present invention provides nucleic acid and protein targets for assays for drugs for the treatment of mental disorders.

In one aspect, the methods comprise the steps of: (i) obtaining a biological sample from a subject; (ii) contacting the sample with a reagent that selectively associates with a polynucleotide or polypeptide encoded by a nucleic acid that hybridizes under stringent conditions to a nucleotide sequence listed in FIGS. 1-14; and (iii) detecting the level of reagent that selectively associates with the sample, thereby determining whether the subject has or is predisposed for a mental disorder.

In some embodiments, the reagent is an antibody. In some embodiments, the reagent is a nucleic acid. In some embodiments, the reagent associates with a polynucleotide. In some embodiments, the reagent associates with a polypeptide. In some embodiments, the polynucleotide comprises a nucleotide sequence listed in FIGS. 1-14. In some embodiments, the polypeptide comprises an amino acid sequence of a gene listed in FIGS. 1-14. In some embodiments, the level of reagent that associates with the sample is different (i.e., higher or lower) from a level associated with humans without a mental disorder. In some embodiments, the biological sample is obtained from lymphocytes, amniotic fluid, spinal fluid, or saliva. In some embodiments, the mental disorder is a mood disorder. In some embodiments, the mental disorder is a psychotic disorder such as schizophrenia.

The invention also provides methods of identifying a compound for treatment of a mental disorder. In some embodiments, the methods comprises the steps of: (i) contacting the compound with a polypeptide, which is encoded by a polynucleotide that hybridizes under stringent conditions to a nucleic acid comprising a nucleotide sequence of FIGS. 1-14; and (ii) determining the functional effect of the compound upon the polypeptide, thereby identifying a compound for treatment of a mental disorder, e.g., schizophrenia.

In some embodiments, the contacting step is performed in vitro. In some embodiment, the polypeptide comprises an amino acid sequence of a gene listed in FIGS. 1-14. In some embodiments, the polypeptide is expressed in a cell or biological sample, and the cell or biological sample is contacted with the compound. In some embodiments, the methods further comprise administering the compound to an animal and determining the effect on the animal, e.g., an invertebrate, a vertebrate, or a mammal. In some embodiments, the determining step comprises testing the animal's mental function.

In some embodiments, the methods comprise the steps of (i) contacting the compound to a cell, the cell comprising a polynucleotide that hybridizes under stringent conditions to a nucleotide sequence of FIGS. 1-14; and (ii) selecting a compound that modulates expression of the polynucleotide, thereby identifying a compound for treatment of a mental disorder. In some embodiments, the polynucleotide comprises a nucleotide sequence listed in FIGS. 1-14. In some embodiment, the expression of the polynucleotide is enhanced. In some embodiments, the expression of the polynucleotide is decreased. In some embodiments, the methods further comprise administering the compound to an animal and determining the effect on the animal. In some embodiments, the determining step comprises testing the animal's mental function. In some embodiments, the mental disorder is a mood disorder or a psychotic disorder. In some embodiments, the psychotic disorder is schizophrenia. In some embodiments, the mood disorder is major depression disorder or bipolar disorder.

The invention also provides methods of treating a mental disorder in a subject. In some embodiments, the methods comprise the step of administering to the subject a therapeutically effective amount of a compound identified using the methods described above. In some embodiments, the mental disorder is a mood disorder or a psychotic disorder. In some embodiments, the compound is a small organic molecule, an antibody, an antisense molecule, an aptamer, an siRNA molecule, or a peptide.

The invention also provides methods of treating mental disorder in a subject, comprising the step of administering to the subject a therapeutically effective amount of a polypeptide, which is encoded by a polynucleotide that hybridizes under stringent conditions to a nucleic acid of FIGS. 1-14. In some embodiments, the polypeptide comprises an amino acid sequence encoded by a gene sequence listed in FIGS. 1-14. In some embodiments, the mental disorder is a mood disorder or a psychotic disorder.

The invention also provides methods of treating mental disorder in a subject, comprising the step of administering to the subject a therapeutically effective amount of a polynucleotide, which hybridizes under stringent conditions to a nucleic acid of FIGS. 1-14. In some embodiments, the mental disorder is a mood disorder or a psychotic disorder. In some embodiments, the psychotic disorder is schizophrenia. In some embodiments, the mood disorder is a bipolar disorder or major depression.

BRIEF DESCRIPTION OF THE DRAWINGS

FIG. 1 lists genes that are differentially expressed in schizophrenic versus control patients in each of the 6 brain regions. For every gene (row) listed: the UniGene ID, GenBank Accession # ("Acc"), Gene Symbol, Chromosome # ("Chr"), and direction of change (up or down) in expression levels are listed in successive columns. The last column provides the name of the differentially expressed gene and related information, where available.

FIG. 2 shows gene ontology (GO) terms enriched in AnCg. Probe sets that showed GO term enrichment and met default FDR correction threshold criteria (http://brainarray.mhri.med.umich.edu/Brainarray/) are listed here. Under each enriched GO term, individual genes are listed in the rows. Information related to the LocusLink ID #, UniGene ID #, Gene Symbol and Gene Description is provided in successive columns.

FIG. 3 shows GO terms enriched in DLPFC. Probe sets that showed GO-term enrichment and met default FDR correction threshold criteria (http://brainarray.mhri.med.umich.edu/Brainarray/) are listed here. Under each enriched GO term, individual genes are listed in the rows. A LocusLink ID #, UniGene ID #, Gene Symbol and Gene Description are indicated in successive columns.

FIG. 4 lists 84 genes which are significantly dysregulated in both lymphoblastic and brain tissues.

FIG. 5 lists 16 genes which are significantly dysregulated in lymphoblasts only. These genes were significant by microarray and the amount and direction of change was confirmed using Q-PCR. Seven of these genes (bold in Accession Number column) exhibited statistically significant dysregulation when examined by Q-PCR and evaluated using the two-tailed t-test.

FIG. 6 lists 11 single nucleotide polymorphic markers correlated with aspartylglucosaminuria (AGA) gene expression which is dysregulated in both brain and lymphocytes of individuals with schizophrenia (see FIG. 4, infra). The regression p-values of genotype with lymphocyte gene expression are shown in the last column.

FIG. 7 lists genes involved in mood disorders and psychotic disorders.

FIG. 8 lists genes involved in mood disorders and psychotic disorders.

FIG. 13 lists genes differentially expressed in the dorsolateral prefrontal cortex (DLPFC) that are involved in mood disorders and psychotic disorders.

FIG. 14 lists lithium responsive genes expressed in the amygdala.

DEFINITIONS

Figure 9:
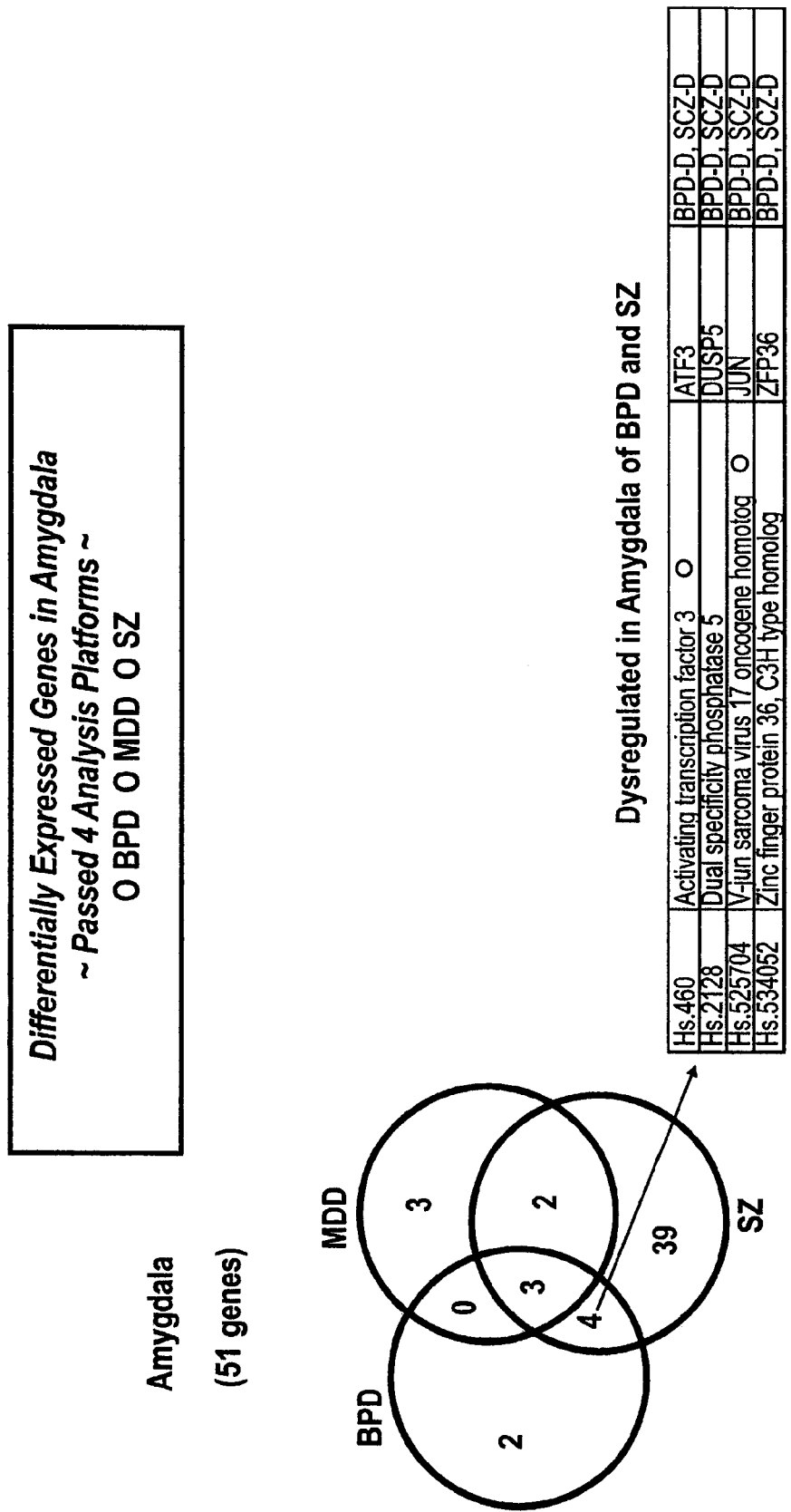
FIGS. 9-12 list genes differentially expressed in the amygdala that are involved in mood disorders and psychotic disorders.

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV). Typically, such disorders have a complex genetic and/or a biochemical component.

"A psychotic disorder" refers to a condition that affects the mind, resulting in at least some loss of contact with reality. Symptoms of a psychotic disorder include, e.g., hallucinations, changed behavior that is not based on reality, delusions and the like. See, e.g., DSM IV. Schizophrenia, schizoaffective disorder, schizophreniform disorder, delusional disorder, brief psychotic disorder, substance-induced psychotic disorder, and shared psychotic disorder are examples of psychotic disorders.

"Schizophrenia" refers to a psychotic disorder involving a withdrawal from reality by an individual. Symptoms comprise for at least a part of a month two or more of the following symptoms: delusions (only one symptom is required if a delusion is bizarre, such as being abducted in a space ship from the sun); hallucinations (only one symptom is required if hallucinations are of at least two voices talking to one another or of a voice that keeps up a running commentary on the patient's thoughts or actions); disorganized speech (e.g., frequent derailment or incoherence); grossly disorganized or catatonic behavior; or negative symptoms, i.e., affective flattening, alogia, or avolition. Schizophrenia encompasses disorders such as, e.g., schizoaffective disorders. Diagnosis of schizophrenia is described in, e.g., Diagnostic and Statistical Manual of Mental Disorders, Fourth Edition (DSM IV). Types of schizophrenia include, e.g., paranoid, disorganized, catatonic, undifferentiated, and residual.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., DSM IV.

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

Anxiety disorders, learning and memory disorders or cognitive disorders are described in DSM IV. Anxiety disorders display co-morbidity with depression, and learning and memory disorders display co-morbidity with schizophrenia.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons. An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

"Determining the functional effect" refers to assaying for a compound that increases or decreases a parameter that is indirectly or directly under the influence of a polynucleotide or polypeptide of the invention (such as a polynucleotide of FIGS. 1-6 or a polypeptide encoded by a gene of FIGS. 1-6), e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the invention or depletion of an substrate; measurement of changes in protein levels of a polypeptide of the invention; measurement of RNA stability; G-protein binding; GPCR phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, colorimetric reactions, antibody binding, inducible markers, and ligand binding assays.

Samples or assays comprising a nucleic acid or protein disclosed herein that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition is achieved when the activity value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

"Biological sample" includes sections of tissues such as biopsy and autopsy samples, and frozen sections taken for histologic purposes. Such samples include blood, serum, lymphocytes, spinal fluid, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish. Biological samples can be used to examine nucleic acids and proteins.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of the polynucleotides, polypeptides, antagonists or agonists of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, *Adv. Drug Res.* 15:29 (1986); Veber and Freidinger *TINS* p. 392 (1985); and Evans et al., *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a CCX CKR, but have one or more peptide linkages optionally replaced by a linkage selected from the group consisting of, e.g., —CH$_2$NH—, —CH$_2$—CH$_2$—, —CH=CH— (cis and trans), —COCH$_2$—, —CH(OH)CH$_2$—, and —CH$_2$SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of a polypeptide or polynucleotide of the invention or inhibiting or increasing the enzymatic activity or expression of a polypeptide or polynucleotide of the invention.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, haplotypes, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M)

(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, $M=5$, $N=-4$, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes. Nucleic acids that hybridize to the genes listed in FIGS. 1-6 are encompassed by the invention.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications* (1990).

The phrase "a nucleic acid sequence encoding" refers to a nucleic acid that contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

One who is "predisposed for a mental disorder" as used herein means a person who has an inclination or a higher likelihood of developing a mental disorder when compared to an average person in the general population.

DETAILED DESCRIPTION OF THE INVENTION

I. Introduction

To understand the complex genetic basis of mental disorders, the present invention provides studies that have been conducted to investigate the expression patterns of genes that are differentially expressed specifically in central nervous system of subjects with psychotic and mood disorders. The large spectrum of symptoms associated with mental disorders is a reflection of the complex genetic basis and complex gene expression patterns in patients with mental disorders. Different combinations of the genes disclosed herein can be responsible for one or more mental disorders. Furthermore, brain pathways or circuits as well as subcellular pathways are important for understanding the development and diagnosis of mental disorders. The selected brain regions described herein (anterior cingulate cortex (AnCg), dorsolateral prefrontal cortex (DLPFC), cerebellar cortex (CB), entorhinal cortex (ERC), superior temporal gyrus (STG), parietal cortex (PC), nucleus accumbens (nAcc), ventral thalamus (VThal), medial thalamus (MThal), amygdala (AMY) and/or the hippocampus (HC)) are implicated in the clinical symptoms of mental disorders such as psychotic and mood disorders. Brain imaging studies focusing on particular brain regions, cytoarchitectural changes in brain regions, expression of key neurotransmittors or related molecules in brain regions, and subcellular pathways in brain regions all contribute to the development of mental disorders, and thus are an important consideration in the diagnosis and therapeutic uses described herein.

Figure 10:
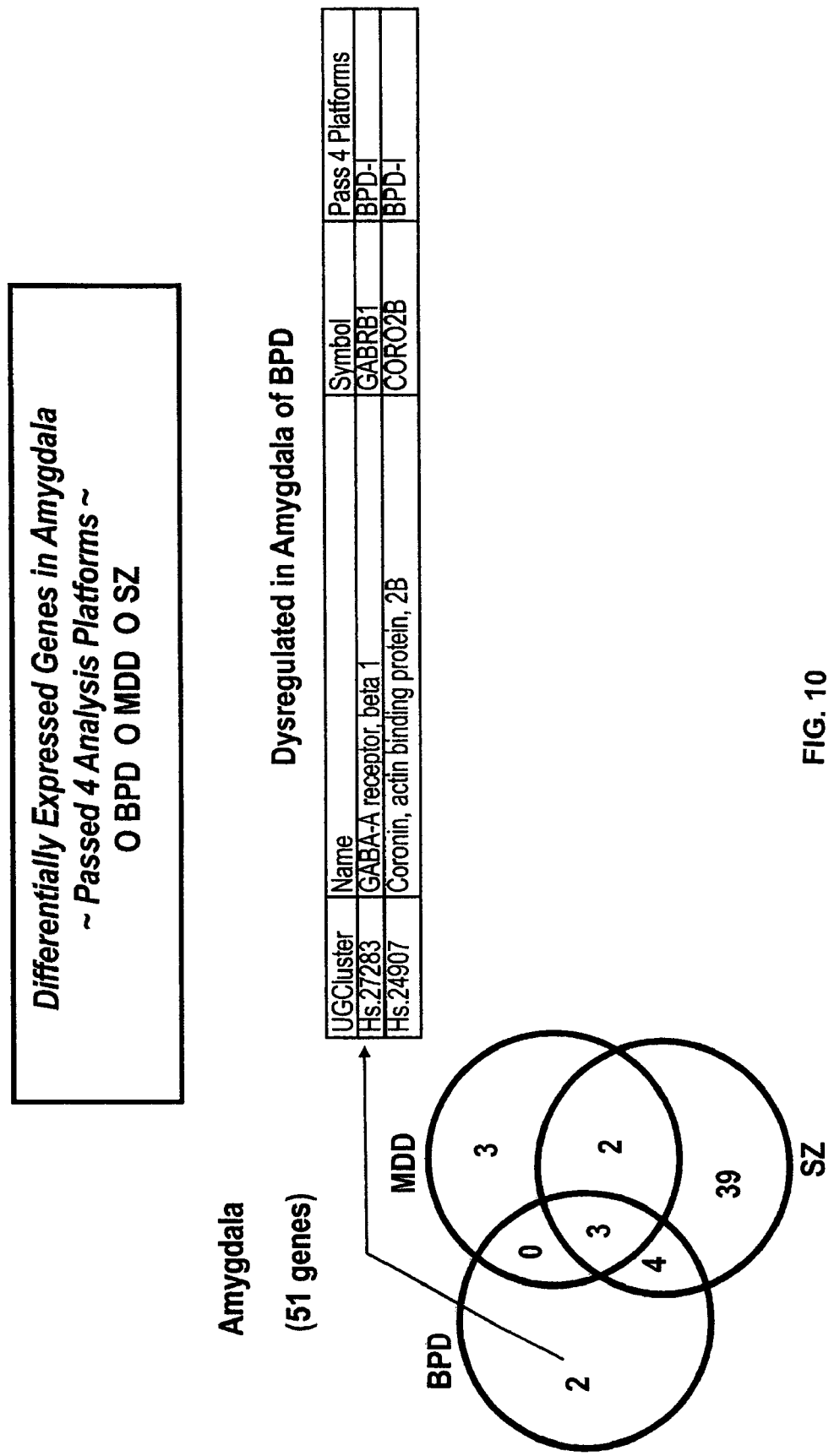
Figure 11:
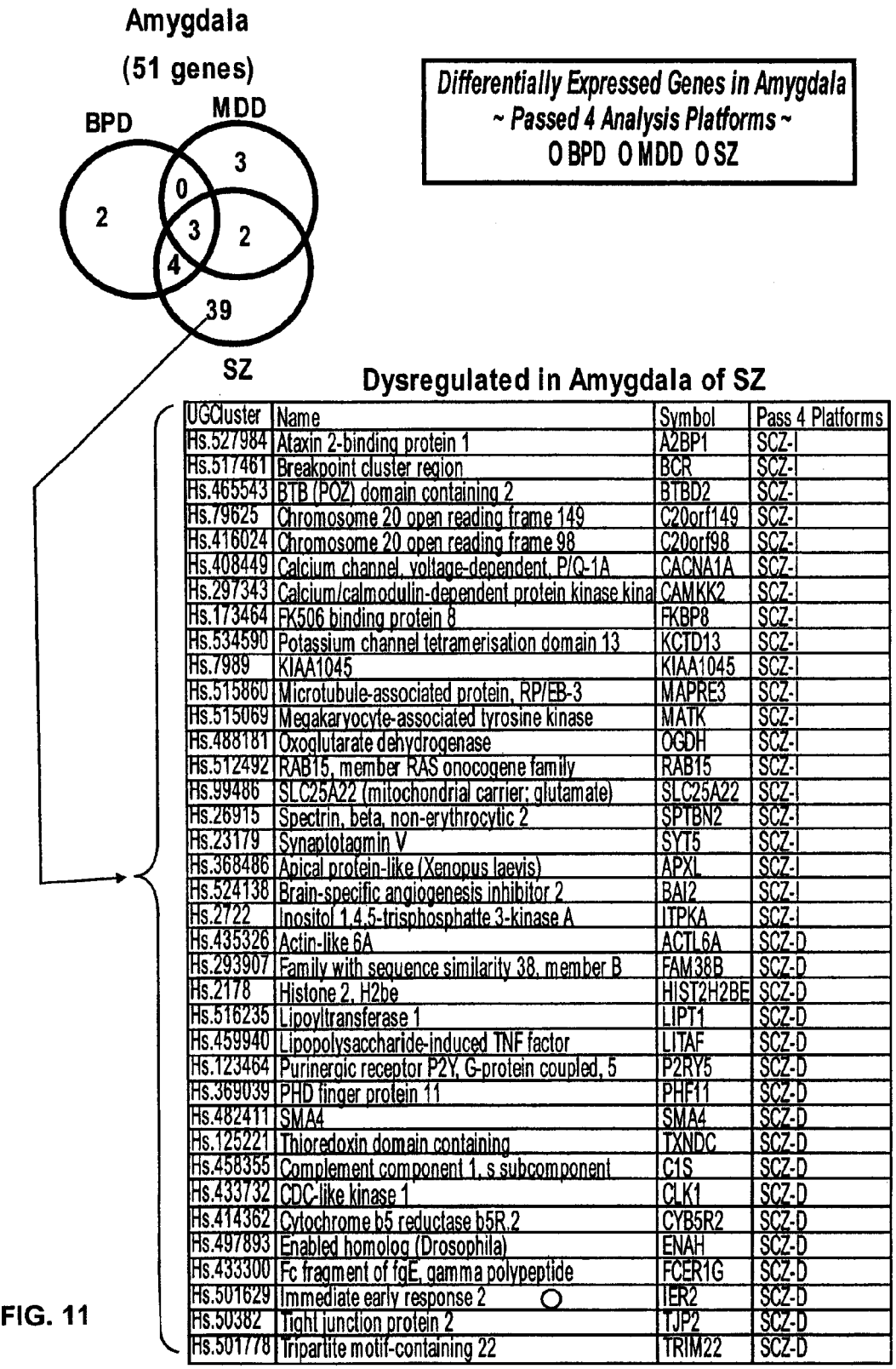
Figure 12:
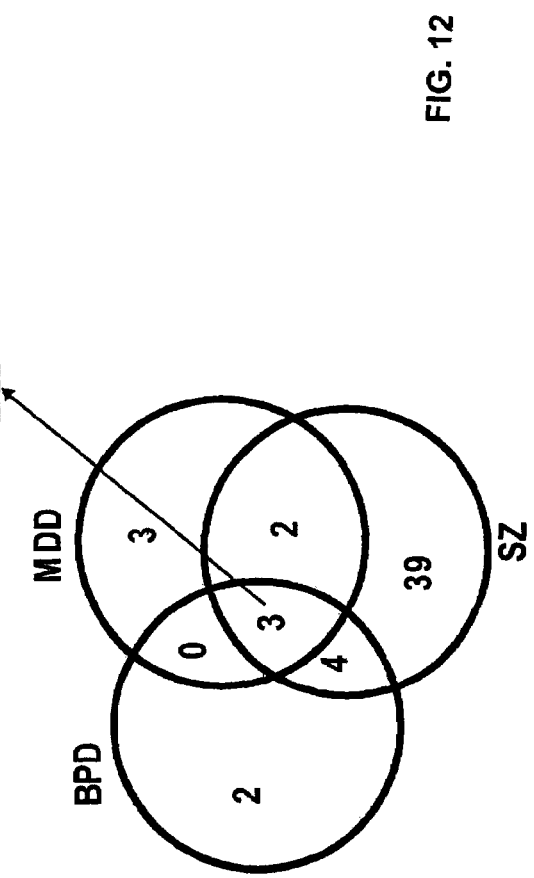
Figure 15:
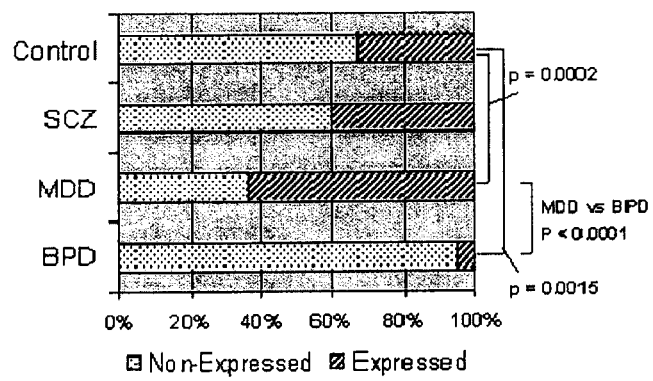
FIG. 15 shows PSPHL locus genotype and PSPHL mRNA expression in BPD, MDD, SCZ, and control subjects.

The present invention demonstrates the altered expression (either higher or lower) of the genes of FIGS. 1-14 at the mRNA or protein level in various regions of the brain (e.g., FIGS. 1-4 and 6) or lymphocytes (e.g., FIGS. 4-6) of patients with mental disorders (e.g., schizophrenia, MDD and BPD) in comparison with normal individuals. This invention thus provides methods for diagnosis of mental disorders, e.g., schizophrenia, MDD and BPD, and the like, and other mental disorders by detecting the level of a transcript or translation product of the genes listed in FIGS. 1-14 as well as their corresponding biochemical pathways. The chromosomal location of such genes can be used to discover other genes in the region that are linked to development of a particular disorder. FIG. 6 of the invention also provides single nucleotide polymorphic markers which are related (in cis or trans) to regulatory sites associated with AGA.

The invention further provides methods of identifying a compound useful for the treatment of such disorders by selecting compounds that modulates the functional effect of the translation products or the expression of the transcripts described herein. The invention also provides for methods of treating patients with such mental disorders, e.g., by administering the compounds of the invention or by gene therapy. Therapeutic compounds include antibodies, peptides, antisense molecules, siRNA, and small organic molecules.

The genes and the polypeptides that they encode, which are associated with psychotic and mood disorders, are useful for facilitating the design and development of various molecular diagnostic tools such as GeneChips™ containing probe sets specific for all or selected mental disorders, including but not limited to psychotic and mood disorders, and as an ante- and/or post-natal diagnostic tool for screening newborns in concert with genetic counseling. Other diagnostic applications include evaluation of disease susceptibility, prognosis, and monitoring of disease or treatment process, as well as providing individualized medicine via predictive drug profiling systems, e.g., by correlating specific genomic motifs with the clinical response of a patient to individual drugs. In addition, the present invention is useful for multiplex SNP or haplotype profiling, including but not limited to the identification of pharmacogenetic targets at the gene, mRNA, protein, and pathway level (see, e.g, Basile V S, Masellis M, Potkin S G, Kennedy J L. Pharmacogenomics in schizophrenia: the quest for individualized therapy. Hum Mol Genet. 2002 Oct. 1; 11(20):2517-30). Profiling of splice variants is also useful for diagnostic and therapeutic applications. Diagnostic kits are contemplated by the present invention, and include arrays, nanoparticles, and magnetic beads. Marker combinations can provide useful diagnosis. Brain expression patterns, regions, pathways, and circuits can be used for in vivo imaging and diagnosis.

The genes and the polypeptides that they encode, described herein, as also useful as drug targets for the development of therapeutic drugs for the treatment or prevention of mental disorders including, but not limited to, psychotic and mood disorders. Mental disorders have a high co-morbidity with other neurological disorders, such as Parkinson's disease or Alzheimer's. Therefore, the present invention can be used for diagnosis and treatment of patients with multiple disease states that include a mental disorder such as a psychotic disorder.

Antipsychotic medicines are in general equally effect for the treatment of schizophrenia, but act by different mechanisms. The similar effectiveness of the drugs for treatment of schizophrenia suggests that they act through a yet as unidentified common pathway. As demonstrated by the results shown herein, these drugs regulate a common gene, and/or a common group of genes as well as a unique set of genes.

The genes listed herein can be used to provide a differential diagnosis or prognosis of mood and psychotic disorders. In some cases, differentially expressed genes can be used to predict and treat particular symptoms or outcomes, such as suicide attempt. The therapeutic agents described herein can be used in combination with known therapeutics. Nucleic acid therapeutics can be delivered using adenoviral vectors, while peptides, nucleic acids, and other therapeutic molecules can be delivered using nanoparticles and translocation peptides. Orally available peptides can be made using D-amino acids or pegylation, and serum half life can be extended using albumin conjugation and the like.

II. General Recombinant Nucleic Acid Methods for Use with the Invention

In numerous embodiments of the present invention, polynucleotides of the invention will be isolated and cloned using recombinant methods. Such polynucleotides include, e.g., those listed in FIGS. 1-14, which can be used for, e.g., protein expression or during the generation of variants, derivatives, expression cassettes, to monitor gene expression, for the isolation or detection of sequences of the invention in different species, for diagnostic purposes in a patient, e.g., to detect mutations or to detect expression levels of nucleic acids or polypeptides of the invention. In some embodiments, the sequences of the invention are operably linked to a heterologous promoter. In one embodiment, the nucleic acids of the invention are from any mammal, including, in particular, e.g., a human, a mouse, a rat, a primate, etc.

A. General Recombinant Nucleic Acids Methods

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA sequence libraries that are made to encode cDNA or genomic DNA. The particular sequences can be located by hybridizing with an oligonucleotide probe, the sequence of which can be derived from the sequences of the genes and/or SNPs listed in FIGS. 1-6, which provide a reference for PCR primers and defines suitable regions for isolating specific probes. Alternatively, where the sequence is cloned into an expression library, the expressed recombinant protein can be detected immunologically with antisera or purified antibodies made against a polypeptide comprising an amino acid sequence encoded by a gene listed in FIGS. 1-14.

Methods for making and screening genomic and cDNA libraries are well known to those of skill in the art (see, e.g., Gubler and Hoffman *Gene* 25:263-269 (1983); Benton and Davis *Science,* 196:180-182 (1977); and Sambrook, supra). Brain cells are an example of suitable cells to isolate RNA and cDNA sequences of the invention.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. Suitable primers can be designed from specific sequences of the invention. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying polynucleotides of the invention from mammalian tissues can be derived from the sequences provided herein. For a general overview of PCR, see, Innis et al. *PCR Protocols: A Guide to Methods and Applications,* Academic Press, San Diego (1990).

Synthetic oligonucleotides can be used to construct genes. This is done using a series of overlapping oligonucleotides, usually 40-120 bp in length, representing both the sense and anti-sense strands of the gene. These DNA fragments are then annealed, ligated and cloned.

A gene encoding a polypeptide of the invention can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

III. Purification of Proteins of the Invention

Either naturally occurring or recombinant polypeptides of the invention can be purified for use in functional assays. Naturally occurring polypeptides, e.g., polypeptides encoded by genes listed in FIGS. 1-14, can be purified, for example, from mouse or human tissue such as brain or any other source of an ortholog. Recombinant polypeptides can be purified from any suitable expression system.

The polypeptides of the invention may be purified to substantial purity by standard techniques, including selective precipitation with such substances as ammonium sulfate; column chromatography, immunopurification methods, and others (see, e.g., Scopes, *Protein Purification Principles and Practice* (1982); U.S. Pat. No. 4,673,641; Ausubel et al., supra; and Sambrook et al., supra).

A number of procedures can be employed when recombinant polypeptides are purified. For example, proteins having established molecular adhesion properties can be reversible fused to polypeptides of the invention. With the appropriate ligand, the polypeptides can be selectively adsorbed to a purification column and then freed from the column in a relatively pure form. The fused protein is then removed by enzymatic activity. Finally the polypeptide can be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

It will be apparent to one of skill that chromatographic techniques can be performed at any scale and using equipment from many different manufacturers (e.g., Pharmacia Biotech).

IV. Detection of Gene Expression

Those of skill in the art will recognize that detection of expression of polynucleotides of the invention has many uses. For example, as discussed herein, detection of the level of polypeptides or polynucleotides of the invention in a patient is useful for diagnosing mood disorders or psychotic disorder or a predisposition for a mood disorder or psychotic disorder. Moreover, detection of gene expression is useful to identify modulators of expression of the polypeptides or polynucleotides of the invention.

A variety of methods of specific DNA and RNA measurement using nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, *"Practice and Theory of Enzyme Immunoassays," Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181:153-162; Bogulayski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1988); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected.

Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells or tissue, preferentially human cells or tissue from a selected brain region, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

V. Immunological Detection of the Polypeptides of the Invention

In addition to the detection of polynucleotide expression using nucleic acid hybridization technology, one can also use immunoassays to detect polypeptides of the invention. Immunoassays can be used to qualitatively or quantitatively analyze polypeptides. A general overview of the applicable technology can be found in Harlow & Lane, *Antibodies: A Laboratory Manual* (1988).

A. Antibodies to Target Polypeptides or Other Immunogens

Methods for producing therapeutic and diagnostic polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein *Nature*, 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their cross-reactivity against unrelated proteins or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring proteins, such as one comprising an amino acid sequence encoded by a gene listed in FIGS. 1-14, may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., supra.

Once target protein specific antibodies are available, the protein can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum that was raised to the protein (e.g., one has an amino acid sequence encoded by a gene listed in FIGS. 1-14) or a fragment thereof. This antiserum is selected to have low cross-reactivity against different proteins and any such cross-reactivity is removed by immunoabsorption prior to use in the immunoassay.

B. Immunological Binding Assays

In a preferred embodiment, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods* in *Cell Biology Volume* 37: *Antibodies in Cell Biology*, Academic Press, Inc. NY (1993); Stites, supra. Immunological binding assays (or immunoassays) typically utilize a "capture agent" to specifically bind to and often immobilize the analyte (in this case a polypeptide of the present invention or antigenic subsequences thereof). The capture agent is a moiety that specifically binds to the analyte. In a preferred embodiment, the capture agent is an antibody that specifically binds, for example, a polypeptide of the invention. The antibody may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111:1401-1406 (1973); and Akerstrom, et al. *J. Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins of interest from tissue samples may be either competitive or noncompetitive. Noncompetitive immunoassays are assays in which the amount of captured analyte (in this case the protein) is directly measured. In one preferred "sandwich" assay, for example, the capture agent (e.g., antibodies specific for a polypeptide encoded by a gene listed in FIGS. 1-14) can be bound directly to a solid substrate where it is immobilized. These immobilized antibodies then capture the polypeptide present in the test sample. The polypeptide thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of analyte (such as a polypeptide encoded by a gene listed in FIGS. 1-14) present in the sample is measured indirectly by measuring the amount of an added (exogenous) analyte displaced (or competed away) from a capture agent (e.g., an antibody specific for the analyte) by the analyte present in the sample. In one competitive assay, a known amount of, in this case, the protein of interest is added to the sample and the sample is then contacted with a capture agent, in this case an antibody that specifically binds to a polypeptide of the invention. The amount of immunogen bound to the antibody is inversely proportional to the concentration of immunogen present in the sample. In a particularly preferred embodiment, the antibody is immobilized on a solid substrate. For example, the amount of the polypeptide bound to the antibody may be determined either by measuring the amount of subject protein present in a protein/antibody complex or, alternatively, by measuring the amount of remaining uncomplexed protein. The amount of protein may be detected by providing a labeled protein molecule.

Immunoassays in the competitive binding format can be used for cross-reactivity determinations. For example, a protein of interest can be immobilized on a solid support. Proteins are added to the assay which compete with the binding of the antisera to the immobilized antigen. The ability of the above proteins to compete with the binding of the antisera to the immobilized protein is compared to that of the protein of interest. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

3. Other Assay Formats

In a particularly preferred embodiment, western blot (immunoblot) analysis is used to detect and quantify the presence of a polypeptide of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, the antibodies specifically bind to a polypeptide of interest on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

VI. Screening for Modulators of Polypeptides and Polynucleotides of the Invention Modulators of polypeptides or polynucleotides of the invention, i.e. agonists or antagonists of their activity or modulators of polypeptide or polynucleotide expression, are useful for treating a number of human diseases, including mood disorders or psychotic disorders. Administration of agonists, antagonists or other agents that modulate expression of the polynucleotides or polypeptides of the invention can be used to treat patients with mood disorders or psychotic disorders.

A. Screening Methods

A number of different screening protocols can be utilized to identify agents that modulate the level of expression or activity of polypeptides and polynucleotides of the invention in cells, particularly mammalian cells, and especially human cells. In general terms, the screening methods involve screening a plurality of agents to identify an agent that modulates the polypeptide activity by binding to a polypeptide of the invention, modulating inhibitor binding to the polypeptide or activating expression of the polypeptide or polynucleotide, for example.

1. Binding Assays

Preliminary screens can be conducted by screening for agents capable of binding to a polypeptide of the invention, as at least some of the agents so identified are likely modulators of polypeptide activity. The binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura, (1985) "Neurotransmitter, Hormone or Drug Receptor Binding Methods," in *Neurotransmitter Receptor* Binding (Yamamura, H. I., et al., eds.), pp. 61-89. The protein utilized in such assays can be naturally expressed, cloned or synthesized.

Binding assays are also useful, e.g., for identifying endogenous proteins that interact with a polypeptide of the invention. For example, antibodies, receptors or other molecules that bind a polypeptide of the invention can be identified in binding assays.

2. Expression Assays

Certain screening methods involve screening for a compound that up or down-regulates the expression of a polypeptide or polynucleotide of the invention. Such methods generally involve conducting cell-based assays in which test compounds are contacted with one or more cells expressing a polypeptide or polynucleotide of the invention and then detecting an increase or decrease in expression (either transcript, translation product, or catalytic product). Some assays are performed with peripheral cells, or other cells, that express an endogenous polypeptide or polynucleotide of the invention.

Polypeptide or polynucleotide expression can be detected in a number of different ways. As described infra, the expression level of a polynucleotide of the invention in a cell can be determined by probing the mRNA expressed in a cell with a probe that specifically hybridizes with a transcript (or complementary nucleic acid derived therefrom) of a polynucleotide of the invention. Probing can be conducted by lysing the cells and conducting Northern blots or without lysing the cells using in situ-hybridization techniques. Alternatively, a polypeptide of the invention can be detected using immunological methods in which a cell lysate is probed with antibodies that specifically bind to a polypeptide of the invention.

Other cell-based assays are reporter assays conducted with cells that do not express a polypeptide or polynucleotide of the invention. Certain of these assays are conducted with a heterologous nucleic acid construct that includes a promoter of a polynucleotide of the invention that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, chloramphenicol acetyl transferase (CAT); Alton and Vapnek (1979) *Nature* 282:864-869), luciferase, β-galactosidase, green fluorescent protein (GFP) and alkaline phosphatase (Toh, et al. (1980) *Eur. J. Biochem.* 182:231-238; and Hall et al. (1983) *J. Mol. Appl. Gen.* 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression of a polynucleotide of the invention and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of expression levels for a control population (e.g., healthy individuals not having or at risk for mood disorders or psychotic disorders). Expression levels can also be determined for cells that do not express a polynucleotide of the invention as a negative control. Such cells generally are otherwise substantially genetically the same as the test cells.

A variety of different types of cells can be utilized in the reporter assays. Cells that express an endogenous polypeptide or polynucleotide of the invention include, e.g., brain cells, including cells from the cerebellum, anterior cingulate cortex, or dorsolateral prefrontal cortex. Cells that do not endogenously express polynucleotides of the invention can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines and stem cells, e.g., neural stem cells.

Various controls can be conducted to ensure that an observed activity is authentic including running parallel reactions with cells that lack the reporter construct or by not contacting a cell harboring the reporter construct with test compound. Compounds can also be further validated as described below.

3. Catalytic Activity

Catalytic activity of polypeptides of the invention can be determined by measuring the production of enzymatic products or by measuring the consumption of substrates. Activity refers to either the rate of catalysis or the ability to the polypeptide to bind ($K_m$) the substrate or release the catalytic product ($K_d$).

Analysis of the activity of polypeptides of the invention are performed according to general biochemical analyses. Such assays include cell-based assays as well as in vitro assays involving purified or partially purified polypeptides or crude cell lysates. The assays generally involve providing a known quantity of substrate and quantifying product as a function of time.

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if expression or activity of a polynucleotide or polypeptide of the invention is in fact upregulated. The animal models utilized in validation studies generally are mammals of any kind. Specific examples of suitable animals include, but are not limited to, primates, mice, and rats.

5. Animal Models

Animal models of mental disorders also find use in screening for modulators. In one embodiment, rat models of schizophrenia or other mental disorder, such as depression, are used for screening. In one embodiment, invertebrate models such as Drosophila models can be used, screening for modulators of Drosophila orthologs of the human genes disclosed herein. In another embodiment, transgenic animal technology including gene knockout technology, for example as a result of homologous recombination with an appropriate gene targeting vector, or gene overexpression, will result in the absence, decreased or increased expression of a polynucleotide or polypeptide of the invention. The same technology can also be applied to make knockout cells. When desired, tissue-specific expression or knockout of a polynucleotide or polypeptide of the invention may be necessary. Transgenic animals generated by such methods find use as animal models of mental disorder and are useful in screening for modulators of mental disorder.

Knockout cells and transgenic mice can be made by insertion of a marker gene or other heterologous gene into an endogenous gene site in the mouse genome via homologous recombination. Such mice can also be made by substituting an endogenous polynucleotide of the invention with a mutated version of the polynucleotide, or by mutating an endogenous polynucleotide, e.g., by exposure to carcinogens.

For development of appropriate stem cells, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244: 1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators of Polypeptides or Polynucleotides of the Invention

The agents tested as modulators of the polypeptides or polynucleotides of the invention can be any small chemical compound, or a biological entity, such as a protein, sugar, nucleic acid or lipid. Alternatively, modulators can be genetically altered versions of a polypeptide or polynucleotide of the invention. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like. Modulators also include agents designed to reduce the level of mRNA of the invention (e.g. antisense molecules, ribozymes, DNAzymes and the like) or the level of translation from an mRNA.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md., etc.).

C. Solid State and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids. Such flexible linkers are known to those of skill in the art. For example, poly(ethelyne glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of the polynucleotides or polypeptides of the invention. In a preferred embodiment, the methods of the invention include such a control reaction. For each of the assay formats described, "no modulator" control reactions that do not include a modulator provide a background level of binding activity.

In some assays it will be desirable to have positive controls to ensure that the components of the assays are working properly. At least two types of positive controls are appropriate. First, a known activator of a polynucleotide or polypeptide of the invention can be incubated with one sample of the assay, and the resulting increase in signal resulting from an increased expression level or activity of polynucleotide or polypeptide determined according to the methods herein. Second, a known inhibitor of a polynucleotide or polypeptide of the invention can be added, and the resulting decrease in signal for the expression or activity can be similarly detected.

D. Computer-Based Assays

Yet another assay for compounds that modulate the activity of a polypeptide or polynucleotide of the invention involves computer assisted drug design, in which a computer system is used to generate a three-dimensional structure of the polypeptide or polynucleotide based on the structural information encoded by its amino acid or nucleotide sequence. The input sequence interacts directly and actively with a pre-established algorithm in a computer program to yield secondary, tertiary, and quaternary structural models of the molecule. Similar analyses can be performed on potential receptors or binding partners of the polypeptides or polynucleotides of the invention. The models of the protein or nucleotide structure are then examined to identify regions of the structure that have the ability to bind, e.g., a polypeptide or polynucleotide of the invention. These regions are then used to identify polypeptides that bind to a polypeptide or polynucleotide of the invention.

The three-dimensional structural model of a protein is generated by entering protein amino acid sequences of at least 10 amino acid residues or corresponding nucleic acid sequences encoding a potential receptor into the computer system. The amino acid sequences encoded by the nucleic acid sequences provided herein represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary, and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of a polypeptide or polynucleotide of the invention to identify binding sites of the polypeptide or polynucleotide of the invention. Binding affinity between the protein and ligands is determined using energy terms to determine which ligands have an enhanced probability of binding to the protein.

Computer systems are also used to screen for mutations, polymorphic variants, alleles and interspecies homologs of genes encoding a polypeptide or polynucleotide of the invention. Such mutations can be associated with disease states or genetic traits and can be used for diagnosis. As described above, GeneChip™ and related technology can also be used to screen for mutations, polymorphic variants, alleles and interspecies homologs. Once the variants are identified, diagnostic assays can be used to identify patients having such mutated genes. Identification of the mutated a polypeptide or polynucleotide of the invention involves receiving input of a first amino acid sequence of a polypeptide of the invention (or of a first nucleic acid sequence encoding a polypeptide of the invention), e.g., any amino acid sequence having at least 60%, optionally at least 70% or 85%, identity with the amino acid sequence of interest, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various polynucleotides, including SNPs and/or haplotypes, of the invention, and mutations associated with disease states and genetic traits.

VII. Compositions, Kits and Integrated Systems

The invention provides compositions, kits and integrated systems for practicing the assays described herein using polypeptides or polynucleotides of the invention, antibodies specific for polypeptides or polynucleotides of the invention, etc.

The invention provides assay compositions for use in solid phase assays; such compositions can include, for example, one or more polynucleotides or polypeptides of the invention immobilized on a solid support, and a labeling reagent. In each case, the assay compositions can also include additional reagents that are desirable for hybridization. Modulators of expression or activity of polynucleotides or polypeptides of the invention can also be included in the assay compositions.

The invention also provides kits for carrying out the therapeutic and diagnostic assays of the invention. The kits typically include a probe that comprises an antibody that specifically binds to polypeptides or polynucleotides of the invention, and a label for detecting the presence of the probe. The kits may include several polynucleotide sequences encoding polypeptides of the invention. Kits can include any of the compositions noted above, and optionally further include additional components such as instructions to practice a high-throughput method of assaying for an effect on expression of the genes encoding the polypeptides of the invention, or on activity of the polypeptides of the invention, one or more containers or compartments (e.g., to hold the probe, labels, or the like), a control modulator of the expression or activity of polypeptides of the invention, a robotic armature for mixing kit components or the like.

The invention also provides integrated systems for high-throughput screening of potential modulators for an effect on the expression or activity of the polypeptides of the invention. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous STAT binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC, MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques. Lasar based systems can also be used.

VIII. Administration and Pharmaceutical Compositions

Modulators of the polynucleotides or polypeptides of the invention (e.g., antagonists or agonists) can be administered directly to a mammalian subject for modulation of activity of those molecules in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

Diseases that can be treated include the following, which include the corresponding reference number from Morrison, *DSM-IV Made Easy,* 1995: Schizophrenia, Catatonic, Subchronic, (295.21); Schizophrenia, Catatonic, Chronic (295.22); Schizophrenia, Catatonic, Subchronic with Acute Exacerbation (295.23); Schizophrenia, Catatonic, Chronic with Acute Exacerbation (295.24); Schizophrenia, Catatonic, in Remission (295.55); Schizophrenia, Catatonic, Unspecified (295.20); Schizophrenia, Disorganized, Subchronic (295.11); Schizophrenia, Disorganized, Chronic (295.12); Schizophrenia, Disorganized, Subchronic with Acute Exacerbation (295.13); Schizophrenia, Disorganized, Chronic with Acute Exacerbation (295.14); Schizophrenia, Disorganized, in Remission (295.15); Schizophrenia, Disorganized, Unspecified (295.10); Schizophrenia, Paranoid, Subchronic (295.31); Schizophrenia, Paranoid, Chronic (295.32); Schizophrenia, Paranoid, Subchronic with Acute Exacerbation (295.33); Schizophrenia, Paranoid, Chronic with Acute Exacerbation (295.34); Schizophrenia, Paranoid, in Remission (295.35); Schizophrenia, Paranoid, Unspecified (295.30); Schizophrenia, Undifferentiated, Subchronic (295.91); Schizophrenia, Undifferentiated, Chronic (295.92); Schizophrenia, Undifferentiated, Subchronic with Acute Exacerbation (295.93); Schizophrenia, Undifferentiated, Chronic with Acute Exacerbation (295.94); Schizophrenia, Undifferentiated, in Remission (295.95); Schizophrenia, Undifferentiated, Unspecified (295.90); Schizophrenia, Residual, Subchronic (295.61); Schizophrenia, Residual, Chronic (295.62); Schizophrenia, Residual, Subchronic with Acute Exacerbation (295.63); Schizophrenia, Residual, Chronic with Acute Exacerbation (295.94); Schizophrenia, Residual, in Remission (295.65); Schizophrenia, Residual, Unspecified (295.60); Delusional (Paranoid) Disorder (297.10); Brief Reactive Psychosis (298.80); Schizophreniform Disorder (295.40); Schizoaffective Disorder (295.70); Induced Psychotic Disorder (297.30); Psychotic Disorder NOS (Atypical Psychosis) (298.90); Personality Disorders, Paranoid (301.00); Personality Disorders, Schizoid (301.20); Personality Disorders, Schizotypal (301.22); Personality Disorders, Antisocial (301.70); Personality Disorders, Borderline (301.83) and bipolar disorders, maniac, hypomaniac, dysthymic or cyclothymic disorders, substance-induced major depression, psychotic disorder, including schizophrenia (paranoid, catatonic, delusional) having schizoaffective disorder, and substance-induced psychotic disorder.

In some embodiments, modulators of polynucleotides or polypeptides of the invention can be combined with other drugs useful for treating mental disorders including psychotic disorders, e.g., schizophrenia; and mood disorders, e.g., bipolar disorders, or major depression. In some preferred embodiments, pharmaceutical compositions of the invention comprise a modulator of a polypeptide of polynucleotide of the invention combined with at least one of the compounds useful for treating schizophrenia, bipolar disorder, or major depression, e.g., such as those described in U.S. Pat. No. 6,297,262; 6,284,760; 6,284,771; 6,232,326; 6,187,752; 6,117,890; 6,239,162 or 6,166,008.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of the a polypeptide or polynucleotide of the invention, alone or in combination with other suitable components, can be made into aerosol formulations (i.e., they can be "nebulized") to be administered via inhalation or in compositions useful for injection. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to effect a beneficial response in the subject over time. The optimal dose level for any patient will depend on a variety of factors including the efficacy of the specific modulator employed, the age, body weight, physical activity, and diet of the patient, on a possible combination with other drugs, and on the severity of the mental disorder. The size of the dose also will be determined by the existence, nature, and extent of any adverse side effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side effects of the modulator at various concentrations, as applied to the mass and overall health of the subject. Administration can be accomplished via single or divided doses.

IX. Gene Therapy Applications

A variety of human diseases can be treated by therapeutic approaches that involve stably introducing a gene into a human cell such that the gene is transcribed and the gene product is produced in the cell. Diseases amenable to treatment by this approach include inherited diseases, including those in which the defect is in a single or multiple genes. Gene therapy is also useful for treatment of acquired diseases and other conditions. For discussions on the application of gene therapy towards the treatment of genetic as well as acquired diseases, see, Miller, *Nature* 357:455-460 (1992); and Mulligan, *Science* 260:926-932 (1993).

In the context of the present invention, gene therapy can be used for treating a variety of disorders and/or diseases in which the polynucleotides and polypeptides of the invention has been implicated. For example, compounds, including polynucleotides, can be identified by the methods of the present invention as effective in treating a mental disorder. Introduction by gene therapy of these polynucleotides can then be used to treat, e.g., mental disorders including mood disorders or psychotic disorders (e.g., schizophrenia).

A. Vectors for Gene Delivery

For delivery to a cell or organism, the polynucleotides of the invention can be incorporated into a vector. Examples of vectors used for such purposes include expression plasmids capable of directing the expression of the nucleic acids in the target cell. In other instances, the vector is a viral vector system wherein the nucleic acids are incorporated into a viral genome that is capable of transfecting the target cell. In a preferred embodiment, the polynucleotides can be operably linked to expression and control sequences that can direct expression of the gene in the desired target host cells. Thus, one can achieve expression of the nucleic acid under appropriate conditions in the target cell.

B. Gene Delivery Systems

Viral vector systems useful in the expression of the nucleic acids include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors are also useful for introducing the nucleic acids of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.,* 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis-acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

In some embodiments of the invention, an antisense polynucleotide is administered which hybridizes to a gene encoding a polypeptide of the invention. The antisense polypeptide can be provided as an antisense oligonucleotide (see, e.g., Murayama et al., *Antisense Nucleic Acid Drug Dev.* 7:109-114 (1997)). Genes encoding an antisense nucleic acid can also be provided; such genes can be introduced into cells by methods known to those of skill in the art. For example, one can introduce an antisense nucleotide sequence in a viral vector, such as, for example, in hepatitis B virus (see, e.g., Ji et al., *J. Viral Hepat.* 4:167-173 (1997)), in adeno-associated virus (see, e.g., Xiao et al., *Brain Res.* 756:76-83 (1997)), or in other systems including, but not limited, to an HVJ (Sendai virus)-liposome gene delivery system (see, e.g., Kaneda et al., *Ann. NY Acad. Sci.* 811:299-308 (1997)), a "peptide vector" (see, e.g., Vidal et al., *CR Acad. Sci. III* 32:279-287 (1997)), as a gene in an episomal or plasmid vector (see, e.g., Cooper et al., *Proc. Natl. Acad. Sci.* 94:6450-6455 (1997), Yew et al. *Hum Gene Ther.* 8:575-584 (1997)), as a gene in a peptide- DNA aggregate (see, e.g., Niidome et al., *J. Biol. Chem.* 272:15307-15312 (1997)), as "naked DNA" (see, e.g., U.S. Pat. Nos. 5,580,859 and 5,589,466), in lipidic vector systems (see, e.g., Lee et al., *Crit Rev Ther Drug Carrier Syst.* 14:173-206 (1997)), polymer coated liposomes (U.S. Pat. Nos. 5,213,804 and 5,013,556), cationic liposomes (Epand et al., U.S. Pat. Nos. 5,283,185; 5,578,475; 5,279,833; and 5,334,761), gas filled microspheres (U.S. Pat. No. 5,542,935), ligand-targeted encapsulated macromolecules (U.S. Pat. Nos. 5,108,921; 5,521,291; 5,554,386; and 5,166,320).

Upregulated transcripts listed in FIGS. 1-14 which are correlated with schizophrenia may be targeted with one or more short interfering RNA (siRNA) sequences that hybridize to specific sequences in the target, as described above. Targeting of certain brain transcripts with siRNA in vivo has been reported, for example, by Zhang et al., J. Gene. Med., 12:1039-45 (2003), who utilized monoclonal antibodies against the transferrin receptor to facilitate passage of liposome-encapsulated siRNA molecules through the blood brain barrier. Targeted siRNAs represent useful therapeutic compounds for attenuating the over-expressed transcripts that are associated with disease states, e.g., schizophrenia.

In another embodiment, conditional expression systems, such as those typified by the tet-regulated systems and the RU-486 system, can be used (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These systems impart small molecule control on the expression of the target gene(s) of interest.

C. Pharmaceutical Formulations

When used for pharmaceutical purposes, the vectors used for gene therapy are formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer, or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans; antioxidants, such as ascorbic acid or glutathione; chelating agents; low molecular weight proteins or other stabilizers or excipients. Other physiologically acceptable compounds include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in Remington's *Pharmaceutical Sciences*, Mack Publishing Company, Philadelphia, Pa., 17th ed. (1985).

D. Administration of Formulations

The formulations of the invention can be delivered to any tissue or organ using any delivery method known to the ordinarily skilled artisan. In some embodiments of the invention, the nucleic acids of the invention are formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

E. Methods of Treatment

The gene therapy formulations of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23 (1):46-65 (1996); Raper et al., *Annals of Surgery* 223(2):116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

X. Diagnosis of Mood and Psychotic Disorders

The present invention also provides methods of diagnosing mood disorders (such as major depression or bipolar disorder), psychotic disorders (such as schizophrenia). In one preferred embodiment, the disease state encompasses psychotic disorders. Diagnosis involves determining the level of a polypeptide or polynucleotide of the invention in a patient and then comparing the level to a baseline or range. Typically, the baseline value is representative of a polypeptide or polynucleotide of the invention in a healthy person not suffering from a mood disorder or psychotic disorder or under the effects of medication or other drugs. Variation of levels of a polypeptide or polynucleotide of the invention from the baseline range (either up or down) indicates that the patient has a mood disorder or psychotic disorder or at risk of developing at least some aspects of a mood disorder or psychotic disorder. In some embodiments, the level of a polypeptide or polynucleotide of the invention are measured by taking a blood, urine or tissue sample from a patient and measuring the amount of a polypeptide or polynucleotide of the invention in the sample using any number of detection methods, such as those discussed herein, e.g., detection of expression levels or SNPs or haplotypes associated with these genes. The genes provided herein also can be used to develop probe sets for PCR and chip assays.

Single nucleotide polymorphism (SNP) analysis is also useful for detecting differences between alleles of the polynucleotides (e.g., genes) of the invention. SNPs linked to genes encoding polypeptides of the invention are useful, for instance, for diagnosis of diseases (e.g., mood disorders such as bipolar disease, major depression, and schizophrenia disorders) whose occurrence is linked to the gene sequences of the invention. For example, if an individual carries at least one SNP linked to a disease-associated allele of the gene sequences of the invention, the individual is likely predisposed for one or more of those diseases. If the individual is homozygous for a disease-linked SNP, the individual is particularly predisposed for occurrence of that disease. In some embodiments, the SNP associated with the gene sequences of the invention is located within 300,000; 200,000; 100,000; 75,000; 50,000; or 10,000 base pairs from the gene sequence.

Various real-time PCR methods can be used to detect SNPs, including, e.g., Taqman or molecular beacon-based assays (e.g., U.S. Pat. Nos. 5,210,015; 5,487,972; Tyagi et al., *Nature Biotechnology* 14:303 (1996); and PCT WO 95/13399) are useful to monitor for the presence of absence of a SNP. Additional SNP detection methods include, e.g., DNA sequencing, sequencing by hybridization, dot blotting, oligonucleotide array (DNA Chip) hybridization analysis, or are described in, e.g., U.S. Pat. No. 6,177,249; Landegren et al., *Genome Research*, 8:769-776 (1998); Botstein et al., *Am J Human Genetics* 32:314-331 (1980); Meyers et al., Methods in Enzymology 155:501-527 (1987); Keen et al., *Trends in Genetics* 7:5 (1991); Myers et al., *Science* 230:1242-1246 (1985); and Kwok et al., *Genomics* 23:138-144 (1994).

In some embodiments, the level of the enzymatic product of a polypeptide or polynucleotide of the invention is measured and compared to a baseline value of a healthy person or persons. Modulated levels of the product compared to the baseline indicates that the patient has a mood disorder or psychotic disorder or is at risk of developing at least some aspects of a mood disorder or psychotic disorder. Patient samples, for example, can be blood, PBS, lymphocytes, saliva, CSF, urine or tissue samples.

Immunoassays using antigens and antibodies for genes differentially expressed in psychotic disorders are also useful for immunoassays such as ELISA and immunohistochemical assays. The genes described herein are also useful for making differential diagnoses for psychiatric disorders.

In some embodiments, schizophrenia in a patient may be diagnosed or otherwise evaluated by visualizing expression in situ of one or more of the gene sequences in FIGS. 1-14. Those skilled in the art of visualizing the presence or expression of molecules including nucleic acids, polypeptides and other biochemicals in the brains of living patients will appreciate that the gene expression information described herein may be utilized in the context of a variety of visualization methods. Such methods include, but are not limited to, single-photon emission-computed tomography (SPECT) and positron-emitting tomography (PET) methods. See, e.g., Vassaux and Groot-wassink, "In Vivo Noninvasive Imaging for Gene Therapy," J. Biomedicine and Biotechnology, 2: 92-101 (2003); Turner, J., Smyth, P., Fallon, J. F., Kennedy, J. L., Potkin, S. G., FIRST BIRN (2006). Imaging and genetics in schizophrenia. Neuroinformatics, in press.

PET and SPECT imaging shows the chemical functioning of organs and tissues, while other imaging techniques—such as X-ray, CT and MRI—show structure. The use of PET and SPECT imaging is useful for qualifying and monitoring the development of brain diseases, including schizophrenia and related disorders. In some instances, the use of PET or SPECT imaging allows diseases to be detected years earlier than the onset of symptoms. The use of small molecules for labeling and visualizing the presence or expression of polypeptides and nucleotides has had success, for example, in visualizing proteins in the brains of Alzheimer's patients, as described by, e.g., Herholz K et al., Mol Imaging Biol., 6(4):239-69 (2004); Nordberg A, Lancet Neurol., 3(9):519-27 (2004); Neuropsychol Rev., Zakzanis K K et al., 13(1):1-18 (2003); Kung M P et al, Brain Res., 1025(1-2):98-105 (2004); and Herholz K, Ann Nucl Med., 17(2):79-89 (2003).

The dysregulated genes disclosed in FIGS. 1-14, or their encoded peptides (if any), or fragments thereof, can be used in the context of PET and SPECT imaging applications. After modification with appropriate tracer residues for PET or SPECT applications, molecules which interact or bind with the transcripts in FIGS. 1-14 or with any polypeptides encoded by those transcripts may be used to visualize the patterns of gene expression and facilitate diagnosis of schizophrenia as described herein. Similarly, if the encoded polypeptides encode enzymes, labeled molecules which interact with the products of catalysis by the enzyme may be used for the in vivo imaging and diagnostic application described herein.

Antisense technology is particularly suitable for detecting the transcripts identified in FIGS. 1-14 herein. For example, the use of antisense peptide nucleic acid (PNA) labeled with an appropriate radionuclide, such as $^{111}$In, and conjugated to a brain drug-targeting system to enable transport across biologic membrane barriers, has been demonstrated to allow imaging of endogenous gene expression in brain cancer. See Suzuki et al., Journal of Nuclear Medicine, 10:1766-1775 (2004). Suzuki et al. utilize a delivery system comprising monoclonal antibodies that target transferring receptors at the blood-brain barrier and facilitate transport of the PNA across that barrier. Modified embodiments of this technique may be used to target upregulated genes associated with schizophrenia, such as the upregulated genes which appear in FIGS. 1-5, in methods of treating schizophrenic patients.

In other embodiments, the dysregulated genes listed in FIGS. 1-14 may be used in the context of prenatal and neonatal diagnostic methods. For example, fetal or neonatal lymphocytes can be isolated and the expression levels of appropriate transcripts (e.g., the transcripts in FIGS. 4-5) may be measured and correlated with the presence or increased likelihood of a mental disorder, e.g., schizophrenia. Similarly, the presence of one or more of the SNPs identified in FIG. 6 may be used to infer or corroborate dysregulated expression of ASG and the likelihood of schizophrenia in prenatal, neonatal, children and adult patients.

In other embodiments, the brain labeling and imaging techniques described herein or variants thereof may be used in conjunction with any of the dysregulated gene sequences in FIGS. 1-4 or 6 in a forensic analysis, i.e., to determine whether deceased individual suffered from schizophrenia. Similarly, forensic examination of lymphocyte expression of any of the genes identified in FIGS. 4-5 may be used alone or in conjunction with other methods to determine whether a deceased individual suffered from schizophrenia.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

Identification of Genes Dysregulated in Schizophrenic Patients

Post mortem mental disorder brains (i.e., from schizophrenia patients) and control brains were used in this study. Each brain pair (case and control) was matched on the basis of gender, age, and postmortem interval. The patient's particular conditions in their terminal phase (agonal factors, e.g., seizure, coma, hypoxia, dehydration, and pyrexia) and the conditions of the brain tissue after death (postmortem factors, e.g., postmortem interval, and freezer interval) are two major influences on RNA preservation in postmortem brain tissue.

Brain pH has been evaluated as an indicator for agonal status, and as an indicator of RNA preservation. Subjects with agonal factors and low pH samples, in which RNA quality was found to be compromised were eliminated from the study.

In this study, dysregulation of gene expression was studied in six brain regions: the anterior cingulate cortex (AnCg), dorsolateral prefrontal cortex (DLPFC), cerebellar cortex (CB), superior temporal gyrus (STG), parietal cortex (PC), and nucleus accumbens (nAcc). Gene expression patterns in schizophrenic patients versus healthy controls were analyzed by using Affymetrix GeneChips {(HG_U133 set (A+B)} to interrogate the transcriptome from human postmortem brains that met the strict quality control criteria referred to above, i.e., the agonal factor index of the donors was 0.0 (zero), and the pH of each individual brain was at least 6.4 (see Tomita et al., 2004; Li et al., 2004).

The probe set sequences used in data analysis are as defined in the CDF files created by the UMICH bioinformatics group (http://brainarray.mhri.med.umich.edu/Brainarray/) eliminating sequence redundancy that is inherent to UniGene definitions. The GeneChip hybridization data were processed, background-corrected, and normalized first with GCRMA using diagnosis (SZ, and control) and site {(University of California at Irvine (UCI), University of Michigan (UM) and University of California at Davis (UCD)} as factors in the analysis of sample replicates. The probe sets that showed (i) statistical significance of p<0.05; (ii) an at least 1.2-fold change (FC) in expression in cases relative to controls in either direction; and (iii) Present (P) call of at least 10% in any given brain region out of the six analyzed (listed above) were selected as differentially expressed, i.e., dysregulated genes.

A total of 1336 transcripts/genes were identified as differentially expressed in schizophrenic versus control brains in one or more of the six brain regions analyzed. Of those, 246 genes were upregulated in AnCg; 166 in CB; 156 in DLPFC; 124 in nAcc; 76 in PC; and 84 in STG. 138 genes were downregulated in AnCg; 187 in CB; 94 in DLPFC; 83 in nAcc; 125 in PC; and 105 in STG. This data is presented in FIG. 1.

Out of the six regions analyzed, only AnCg and DLPFC showed probe sets with Gene Ontology (GO) term enrichments and no significant enrichment of KEGG pathways. GO terms enriched in AnCg are listed in FIG. 2. FIG. 2 shows that 3 GO terms were enriched in AnCg, specifically: GO:0050874, organismal physiological process (with 11 probe sets); GO:0058550, eukaryotic translation factor 2 complex (with 3 probe sets); and GO:0005739, mitochondrion (with 25 probe sets).

FIG. 3 shows that a single GO term was enriched in DLPFC, specifically: GO:0005622 intracellular (with 90 probe sets).

Example 2

Peripheral Biomarker Expression of Dysregulated Genes Found in Brain

For this study, a separate cohort of individuals with schizophrenia (n=5) were matched for gender and age to unaffected (n=5) members of a pedigree. Freshly isolated lymphocytes from each individual were transformed using the Epstein-Barr Virus and grown until confluent in RPMI-1640 media supplemented with 15% fetal bovine serum (heat-inactivated), 2 mM L-glutamine and 25 mg of gentamicin. RNA was extracted from ~5×10$^7$ lymphoblastic cells using the standard TRIzol isolation protocol (Invitrogen, Carlsbad, Calif.). Affymetrix Human Genome U133A Arrays were used for gene expression according to the manufacturer's protocol. The gene expression traits were derived from the U133A chips and analyzed by robust multiarray condensation algorithm (RMA). Differential gene expression (gene expression trait for the purpose of this analysis) was defined as a gene that displayed a significant two-tailed t-test (p<0.05) in schizophrenia versus unaffected family members. There were 1344 genes that passed the t-test for dysregulation in lymphocytes in schizophrenia compared to unaffecteds. This list was compared to genes in FIG. 1 (showing brain dysregulated genes in schizophrenia). The genes that were dysregulated in both brain and lymphocytes are shown in FIG. 4.

The list of 84 dysregulated genes in FIG. 4 may be grouped into those genes that agree in direction between brain and lymphoblasts, and those genes that disagree in direction between brain and lymphoblasts. Both dysregulated gene sets are biomarkers. The lymphoblasts do not have agonal factors, pH, or medication effects such as commonly seen in brain tissue. Thus, the gene transcripts in FIG. 4 may be used for monitoring lymphoblasts during treatment or for diagnostic purposes.

The subset of the 1344 genes identified by microarray analysis as significantly dysregulated in lymphoblasts only (i.e., not brains) is shown in FIG. 5. The microarray data was validated using Q-PCR to determine the fold change and direction of gene expression in the lymphocyte samples. Eight of these genes meet statistical significance in Q-PCR by t-test (two-tailed).

Aspartylglucosaminuria (AGA) gene expression is dysregulated in both the brain and lymphocytes of individuals with schizophrenia (FIG. 4). Eleven single nucleotide polymorphic markers were identified which correlate with AGA gene expression are shown in FIG. 6. FIG. 6 also shows the regression p-values of genotype with lymphocyte gene expression. Of the 11 markers, 8 are associated with a cis-regulatory site (i.e., the Cis value is less then 5 Mb) and 3 are related to a trans-regulatory site (the Cis value is greater than 5 Mb). Detecting these SNPs can facilitate the prediction of AGA gene expression in lymphoblasts. Similarly, detecting SNPs correlated with the expression of other dysregulated genes can facilitate the prediction of expression levels of those genes. The SNPs in FIG. 6 also represent targets for controlling expression of AGA, for diagnosing and treating schizophrenia, or for diagnosing and treating other disorders associated with altered AGA expression. For SNPs rs723820, rs723819, rs1112286, rs1375749, FIG. 6 shows that the minor alleles are associated with the decreased AGA expression in schizophrenia.

Example 3

Validation of PSPHL Insertion Deletion Mutation

The present invention extended the previous findings regarding the insertion-deletion polymorphism of phosphoserine phosphatase-like gene, and the association between deletion allele of PSPHL and susceptibility to bipolar disorder (BPD).

We previously determined 1) PSPHL gene consists of 4 exons. Exons 1, 2, 3 and 4 are 213 bp, 114 bp, 122 bp and 501 bp, in length, respectively, and span introns 1, 2 and 3 (3221 bp, 829 bp and 11939 bp, in length, respectively). 2) PSPHL and PSPH are highly homologous, which locate 200 kb apart from each other on chromosome 7p11.2 region. 3) PSPHL gene has two alternative transcripts, one of which utilizes the exons 1-4 (PSPHL-A), while another utilizes the exons 1, 2 and 4 (PSPHL-B). Predicted proteins of PSPHL-A and PSPHL-B share N-terminal 57 common amino acids, transcribed from exons 1 and 2. PSPH and the predicted PSPHL-A&B have 31 amino acids in common. 4) There locates an insertion/deletion polymorphism at the PSPHL locus. The deleted genomic region spans more than 30 kb, including the promoter region and the exons 1, 2 and 3 of PSPHL gene. 5)

PSPHL shows a dichotomous (present or absent) pattern of expression among human population, which may due to the insertion/deletion polymorphism at the PSPHL locus. 6) Number of individuals who expresses PSPHL was significantly smaller in BPD patient group compared to control group. 7) Since PSPH is the rate limiting enzyme for serine synthesis, PSPHL may be involved in serine amino acid metabolic pathway, but might be involved in other pathways.

In the present invention, we further determined the followings:

1) We verified involvement of the insertion-deletion polymorphism at the PSPHL locus on the expression pattern of the gene.

Among the 125 human postmortem brain tissues (19 BPD, 22 MDD, 20 SCZ patients and 64 controls) analyzed regarding the PSPHL genotype and PSPHL mRNA expression, 81 subjects (18 BPD, 8 MDD, 12 SCZ, and 43 Controls) showed homozygous pattern of the deletion allele (Del/Del) for the PSPHL locus, and all of the 81 Del/Del individuals lacked PSPHL mRNA expression. On the other hand, 40 subjects (1 BPD, 13 MDD, 8 SCZ, and 18 Controls) showed heterozygous pattern of the insertion and deletion alleles (Ins/Del) for the PSPHL locus, and 4 subjects (1 MDD and 3 Controls) showed homozygous pattern of the insertion allele (Ins/Ins). All of the 44 subjects (40 Ins/Del and 4 Ins/Ins), which have at least one insertion allele, showed PSPHL mRNA expression. This findings support that the presence/absence of PSPHL mRNA expression is due to the insertion/deletion polymorphism at the PSPHL locus. Our observations on the 64 control subjects exactly matched Hardy Weinberg expectations. Allele frequencies for the insertion and deletion alleles for the PSPHL locus were estimated 0.18 and 0.82, respectively.

2) We verified that number of individuals who expresses PSPHL was significantly smaller in BPD patient group compared to control group, and significantly larger in MDD patient group compared to the control group.

Based on hypergeometric distribution, the cumulative p value for observing 1 or less PSPHL non-expressed individuals in the 19 BPD patients is 0.0015. Also, the cumulative p value for observing 14 or more PSPHL-expressed individuals in the 22 MDD patients is 0.0002. There is no significant difference in the distribution between SCZ patients and controls. It is noteworthy that PSPHL non-expressed individuals are predominant in the BPD subjects, whereas PSPHL-expressed individuals are predominant in the MDD subjects. The probability of the observed difference in the distribution between BPD and MDD is 0.000098 based on the Fisher's exact test. These findings could be applicable for genetic testing to predict potential BPD patients among depressed patients who come to see physicians in their early stage of the chronic illnesses.

3) We characterized that PSPHL-B mRNA expression level was also about 10 times higher than PSPHL-A in human postmortem brain tissue and cell lines derived from human brain.

PSPHL has at least two alternative transcripts; PSPHL-A (consists of the exons 1, 2, 3 and 4) and PSPHL-B (consists of the exons 1, 2 and 4). Based on quantitative RT-PCR evaluation with primer sets and TaqMan probes specific to PSPHL-A and PSPHL-B, both PSPHL-A and PSPHL-B were expressed in human postmortem brain cortices, including anterior cingulate and cerebellar cortices, from subjects which have at least one PSPHL insertion allele. PSPHL-B mRNA expression level was about 10 times higher than PSPHL-A in the brain tissues analyzed. Also, both PSPHL-A and PSPHL-B were expressed in cell lines derived from human brain, including human neuroblastoma cell lines, SK-N-SH, human glioma cell line, Hs 683, and human oligodendrocyte-derived cell line, OL, which have at least one PSPHL insertion allele. PSPHL-B mRNA expression level was also about 10 times higher than PSPHL-A in these cell lines. The glioblastoma cell line, U87-MG, which has homozygous PSPHL deletion allele, lack the expression of PSPHL-A and PSPHL-B.

4) We verified promoter activity of 5' region of the PSPHL gene. The 5'-region of PSPHL (1015 bp fragment) was cloned into pGL-basic vector show sufficient promoter activity at least in the Hela cells and human oligodendrocyte cell line, OL. The vector contains the same region in opposite direction (negative control) did not show promoter activity.

The above examples are provided to illustrate the invention but not to limit its scope. Other variants of the invention will be readily apparent to one of ordinary skill in the art and are encompassed by the appended claims. All publications, databases, Genbank sequences, GO terms, patents, and patent applications cited herein are hereby incorporated by reference.

What is claimed is:

1. A method for facilitating the diagnosis of bipolar disorder in a human subject, the method comprising the steps of:
   (i) obtaining a dorsolateral prefrontal cortex (DLPFC), anterior cingulate cortex (AnCg), or lymphocyte sample from said subject;
   (ii) measuring the level of major histocompatibility complex, class II, DP alpha 1 (HLA-DPA1) mRNA transcription in said sample using nucleic acid probes complementary to HLA-DPA1 mRNA;
   (iii) comparing the level of measured HLA-DPA1 mRNA transcription in said sample to the level of HLA-DPA1 mRNA transcription in a control population that does not have bipolar disorder, wherein a decreased level of HLA-DPA1 mRNA relative to the control population indicates an increased likelihood of bipolar disorder in said subject; and
   (iv) recording or reporting a diagnosis of an increased likelihood of bipolar disorder in said subject based on said comparing.

2. The method of claim 1, wherein the decreased level of HLA-DPA1 mRNA corresponds to an at least 1.2-fold decrease in the level of HLA-DPA1 mRNA relative to the control population at a statistical significance of $p<0.05$.

3. The method of claim 1, wherein the level of HLA-DPA1 mRNA transcription in said sample is measured using a nucleic acid hybridization technique.

4. The method of claim 1, wherein the level of HLA-DPA1 mRNA transcription in said sample is measured using a nucleic acid amplification system.

5. The method of claim 4, wherein said nucleic acid amplification system is the polymerase chain reaction (PCR).

6. The method of claim 1, wherein said nucleic acid probes comprise a label.

7. The method of claim 6, wherein said label is selected from the group consisting of isotopes, chromophores, lumiphores, chromogens, and biotin.

8. The method of claim 6, wherein said label is selected from the group consisting of ligands, fluorophores, chemiluminescent agents, enzymes, and antibodies.

9. The method of claim 6, wherein said label is detected using a detector.

* * * * *